US008722671B2

(12) United States Patent
Plettenburg et al.

(10) Patent No.: US 8,722,671 B2
(45) Date of Patent: May 13, 2014

(54) ISOQUINOLINE DERIVATIVES

(75) Inventors: Oliver Plettenburg, Kelkheim (DE);
Armin Hofmeister, Dexheim (DE);
Dieter Kadereit, Offenbach (DE);
Stefan Peukert, Arlington, MA (US);
Sven Ruf, Mainz (DE); Kurt Ritter,
Frankfurt (DE); Matthias Loehn,
Kelkheim (DE); Yuri Ivashchenko,
Hattersheim (DE); Peter Monecke,
Darmstadt (DE); Matthias Dreyer,
Frankfurt (DE); Aimo Kannt, Frankfurt
am Main (DE)

(73) Assignee: Sanofi, Paris (FR)

( * ) Notice: Subject to any disclaimer, the term of this patent is extended or adjusted under 35 U.S.C. 154(b) by 43 days.

(21) Appl. No.: 13/160,983

(22) Filed: Jun. 15, 2011

(65) Prior Publication Data

US 2011/0245248 A1  Oct. 6, 2011

Related U.S. Application Data

(60) Division of application No. 11/961,193, filed on Dec. 20, 2007, now Pat. No. 8,501,736, which is a continuation of application No. PCT/EP2006/005648, filed on Jun. 13, 2006.

(30) Foreign Application Priority Data

Jun. 28, 2005 (EP) .................... 05013868

(51) Int. Cl.
*A61K 31/535* (2006.01)
*C07D 217/00* (2006.01)

(52) U.S. Cl.
USPC ....................... 514/235.2; 546/139

(58) Field of Classification Search
None
See application file for complete search history.

(56) References Cited

U.S. PATENT DOCUMENTS

| | | | |
|---|---|---|---|
| 5,480,883 | A | 1/1996 | Spada et al. |
| 6,903,107 | B1 | 6/2005 | Timmers et al. |
| 7,217,722 | B2 | 5/2007 | Takami et al. |
| 7,618,985 | B2 | 11/2009 | Ray et al. |
| 2003/0125344 | A1 | 7/2003 | Nagarathnam et al. |
| 2003/0220368 | A1 | 11/2003 | Ozaki et al. |
| 2004/0138286 | A1 | 7/2004 | Imazaki et al. |
| 2006/0079556 | A1 | 4/2006 | Sher et al. |
| 2007/0060595 | A1 | 3/2007 | Yoshizawa et al. |
| 2008/0045566 | A1 | 2/2008 | Ray et al. |

FOREIGN PATENT DOCUMENTS

| | | |
|---|---|---|
| EP | 1403255 | 3/2004 |
| EP | 1541559 A1 | 6/2005 |
| EP | 1550660 | 7/2005 |
| FR | 2485537 | 6/1980 |
| JP | 10087629 | 4/1998 |
| WO | 9202476 | 2/1992 |
| WO | 9706802 | 2/1997 |
| WO | 9723214 | 7/1997 |
| WO | 9806433 | 2/1998 |
| WO | 9911642 | 3/1999 |
| WO | 0024718 | 5/2000 |
| WO | 0073299 | 12/2000 |
| WO | 0139726 | 6/2001 |
| WO | 0153288 | 7/2001 |
| WO | 0156988 | 8/2001 |
| WO | 0164238 | 9/2001 |
| WO | 0164656 | 9/2001 |
| WO | 0177101 | 10/2001 |
| WO | 0192227 | 12/2001 |
| WO | 0234712 | 5/2002 |
| WO | 02055496 | 7/2002 |
| WO | 02076457 | 10/2002 |
| WO | 02088101 | 11/2002 |
| WO | 03018556 | 3/2003 |
| WO | 03024450 | 3/2003 |
| WO | 03053330 | 7/2003 |
| WO | 2004106325 | 12/2004 |
| WO | 2004113297 | 12/2004 |
| WO | 2005035933 | 2/2005 |
| WO | 2005030130 | 4/2005 |
| WO | 2005030791 | 4/2005 |
| WO | 2005035516 | 4/2005 |
| WO | 2005054202 | 6/2005 |
| WO | 2005074535 | 8/2005 |
| WO | 2005087226 | 9/2005 |
| WO | 2005095362 | 10/2005 |
| WO | 2007012421 | 2/2007 |
| WO | 2007012422 | 2/2007 |
| WO | 2007039563 | 4/2007 |
| WO | 2007063916 | 6/2007 |
| WO | 2008020081 | 2/2008 |
| WO | 2008077555 | 7/2008 |
| WO | 2008077556 | 7/2008 |

OTHER PUBLICATIONS

Daviglus, M et al Ann Intern. Med 2010 vol. 153 pp. 176-181.*
Zhou, Yan et al., "Nonsteroidal Anti-Inflammatory Drugs Can Lower Amyloidogenic Aβ42 by Inhibiting Rho," Science (2003), vol. 302, pp. 1215-1217.

(Continued)

*Primary Examiner* — Heidi Reese
(74) *Attorney, Agent, or Firm* — Scully, Scott, Murphy & Presser, P.C.

(57) ABSTRACT

The invention relates to 6-piperidinyl-substituted isoquinoline derivatives of the formula (I)

(I)

useful for the treatment and/or prevention of diseases associated with Rho-kinase and/or Rho-kinase mediated phosphorylation of myosin light chain phosphatase, and compositions containing such compounds.

25 Claims, No Drawings

(56) References Cited

OTHER PUBLICATIONS

Okada, Hiroshi et al., "Synthesis and Antitumor Activities of Prodrugs of Benzoylphenylureas," Chemical and Pharmaceutical Bulletin (1994), vol. 42, pp. 57-61.
Negoro, Nobuyuki et al., "The Kinase Inhibitor Fasudil (HA-1077) Reduces Intimal Hyperplasia through Inhibiting Migration and Enhancing Cell Loss of Vascular Smooth Muscle Cells," Biochemical and Biophysical Research Communications (1999), vol. 262, pp. 211-215.
Somlyo, Avril V. et al., "Rho-Kinase Inhibitor Retards Migration and in Vivo Dissemination of Human Prostate Cancer Cells," Biochemical and Biophysical Research Communications (2000), vol. 269, pp. 652-659.
Uchida, Shigeki et al., "The Suppression of Small GTPase Rho Signal Transduction Pathway Inhibits Angiogenesis in Vitro and in Vivo," Biochemical and Biophysical Research Communications (2000), vol. 269, pp. 633-640.
Wakino, Shu et al., "Rho/Rho Kinase as a Potential Target for the Treatment of Renal Disease," Drug News and Perspectives (2005), vol. 18, pp. 639-643.
J. Bonjoch, et al., Tetrahedron Letter., 2003, 44, 8387.
Iwakubo, M., et al., Design and Synthesis of Rho Kinase Inhibitors (III), Bioorganic & Medicinal Chemistry, vol. 15, (2007), pp. 1022-1033.
Iwakubo, M, et al. Design and Synthesis of Rho Kinase Inhibitors (II), Bioorganic & Medicinal Chemistry, vol. 15, (2007), pp. 350-364.
Curran, T.T., et al., The preparation of Optically Active 2-Cyclopenten-1-4-Diol Derivatives from Furfuryl Alcohol, Tetrahedron, vol. 53, No. 6, p. 1983-2004.
Tamura, M., al. Development of Specific Rho-Kinase Inhibitors and Their Clinical Application, Biochimica et Biophysica Acta. (2005), vol. 1754, pp. 245-252.
Becker, Daniel P., et al., "A Short Synthesis of 1-Azaadamantan-4-one and the 4r and 4s Isomers of 4-Amino-1-azadamantane", Synthesis (1992) vol. 11, pp. 1080-1082.
Degraffenreid, Michael R., et al., "An Efficient and Scalable One-Pot Double Michael Addition-Diectramann Condensation for the Synthesis of 4,4-Disubstituted Cyclohexane B-ketosis", Journal of Organic Chemistry (2007), vol. 72, pp. 7455-7458.
Lednicer, Daniel, et al., "4-amino-4-aryl cyclohexanones and their derivatives, A Novel Class of Analgesics-1 Modification of the Aryl Ring". Journal of Medicinal Chemistry (1980), vol. 23, pp. 424-430.
Caron, Stephane, et al., "The Synthesis of a Selective PDE/TnFa Inhibitor", Organic Process Research and Development (2001), vol. 5, pp. 587-592.
U.S. Appl. No. 12/970,376 to Plettenburg, et al., filed Dec. 16, 2010.
U.S. Appl. No. 13/000,754 to Plettenburg, et al., filed Apr. 20, 2011.
U.S. Appl. No. 13/000,202 to Plettenburg, et al., filed Dec. 20, 2010.
U.S. Appl. No. 11/961,197 to Plettenburg, et al, filed Dec. 20, 2007.
U.S. Appl. No. 12/019,866 to Plettenburg, et al., filed Jan. 25, 2008.
U.S. Appl. No. 12/069,799 to Plettenburg, et. al., filed Jan. 25, 2008.
U.S. Appl. No. 12/487,479 to Plettenburg, et al., filed Jun. 18, 2009.
U.S. Appl. No. 12/467,455 to Plettenburg, et al., filed Jun. 18, 2009.
U.S. Appl. No. 12/487,403 to Plettenburg, et al., filed Jun. 18, 2009.
U.S. Appl. No. 12/487,409 to Plettenburg, et al., filed Jun. 18, 2009.
U.S. Appl. No. 12/467,386 to Plettenburg, et al., filed Jun. 18, 2009.
U.S. Appl. No. 12/487,503 to Plettenburg, et al., filed Jun. 18, 2009.
U.S. Appl. No. 12/487,525 to Plettenburg, et al., filed Jun. 18, 2009.
Alvarez, M. et al., "Product Class 5: Isoquinolines," Science of Synthesis (2005), vol. 15, pp. 661-838.
Alvarez, M. et al., "Product Class 6: Isoquinolines," Science of Synthesis (2005), vol. 15, pp. 839-906.
Al, Shingo et al., "Rho-Rho kinase is involved in smooth muscle cell migration through myosin light chain phosphorylation-dependent and independent pathways," Atherosclerosis (2001), vol. 155, pp. 321-327.
Bauer, Markus et al., "Dichotomous Regulation of Myosin Phosphorylation and Shape Change by Rho-Kinase and Calcium in Intact Human Platelets," Blood (1999), vol. 94, pp. 1665-1672.
Chellaiah, Meenakshi et al., "Rho-dependent Rho Kinase Activation Increases CD44 Surface Expression and Bone Resorption in Osteoclasts," The Journal of Biological Chemistry (2003), vol. 278, pp. 29086-29097.
Chitaley, Kanchan et al., "Antagonism of Rho-kinase stimulates rat penile erection via a nitric oxide-independent pathway," Nature Medicine (2001), vol. 7, pp. 119-122.
Maruoka, Shuichiro et al., "Elastase Anti-elastase imbalance in the Pathogens of COPD," Nippon Rinsho (1999), vol. 57, pp. 1982-1987.
Demiryürek, Ş eniz et al., "Effects of fasudil, a Rho-kinase inhibitor, on myocardial preconditioning in anesthetized rats," European Journal of Pharmacology (2005), vol. 527, pp. 129-140.
Retzer, Michaela et al., "Mildly oxidised low density lipoprotein induces platelet shape change via Rho-kinase-dependent phosphorylation of myosin light chain and moesin," FEBS Letters (2000), vol. 466, pp. 70-74.
Kimura, Kazushi et al., "Regulation of the Association of Adducin with Actin Filaments by Rho-associated Kinase (Rho-kinase) and Myosin Phosphatase," The Journal of Biological Chemistry (1998), vol. 273, pp. 5542-5548.
Fukumoto, Y. et al., "Acute vasodilator effects of a Rho-kinase inhibitor, fasudil, in patients with severe pulmonary hypertension," Heart (2005), vol. 91, pp. 391-392.
Gingras, Denis et al., "Tyrosine phosphorylation of the vascular endothelial-growth-factor receptor-2 (VEGFR-2) is modulated by Rho proteins," Biochemical Journal (2000), vol. 348, pp. 273-280.
Gokina, Natalia I. et al., "Effects of Rho kinase inhibition on cerebral artery myogenic tone and reactivity," Journal of Applied Physiology (2005), vol. 98, pp. 1940-1948.
Yoshida, Yoshiki et al., "Studies on Anti-*Helicobacter pylori* Agents. Part 1: Benzyloxyisoquinoline Derivatives," Bioorganic and Medicinal Chemistry (1999), vol. 7, pp. 2647-2666.
Hara, Masahito et al., "Protein kinase inhibition by fasudil hydrochloride promotes neurological recovery after spinal cord injury in rats," Journal of Neurosurgery: Spine 1 (2000), vol. 93, pp. 94-101.
Hattori, Tsuyoshi et al., "Long-Term Inhibition of Rho-Kinase Suppresses Left Ventricular Remodeling After Myocardial Infarction in Mice," Circulation (2004), vol. 109, pp. 2234-2239.
Hitomi, Asako et al., "Hemorheological abnormalities in experimental cerebral ischemia and effects of protein kinase inhibitor on blood fluidity," Life Sciences (2000), vol. 67, pp. 1929-1939.
Honjo, Megumi et al., "Effects of Rho-Associated Protein Kinase Inhibitor Y-27632 on Intraocular Pressure and Outflow Facility," Investigative Ophthalmology and Visual Science (2001), vol. 42, pp. 137-144.
Inoue, Makoto et al., "Initiation of neuropathic pain requires lysophosphatidic acid receptor signaling," Nature Medicine (2004), vol. 10, pp. 712-718.
Itoh, Kazuyuki et al., "An essential part for Rho-associated kinase in the transcellular invasion of tumor cells," Nature Medicine (1999), vol. 5, pp. 221-225.
Kawaguchi, Atsuhiro et al., "The effect of a Rho kinase inhibitor Y-27632 on superoxide production, aggregation and adhesion in human polymorphonuclear leukocytes," European Journal of Pharmacology (2000), vol. 403, pp. 203-208.
Kim, Inkyeom et al., "Thin and Thick Filament Regulation of Contractility in Experimental Cerebral Vasospasm," Neurosurgery (2000), vol. 46, pp. 440-447.
Amano, Mutsuki et al., "Formation of Actin Stress Fibers and Focal Adhesions Enhanced by Rho-Kinase," Science (1997), vol. 275, pp. 1308-1311.
Kishi, Takuya et al., "Rho-Kinase Inhibitor Improves Increased Vascular Resistance and Impaired Vasodilation of the Forearm in Patients with Heart Failure," Circulation (2005), vol. 111, pp. 2741-2747.
Klages, Birgit et al., "Activation of G12/G13 Results in Shape Change and Rho/Rho-Kinase-mediated Myosin Light Chain Phosphorylation in Mouse Platelets," The Journal of Cell Biology (1999), vol. 144, pp. 745-754.

(56) References Cited

OTHER PUBLICATIONS

Noma, Kensuke et al., "Physiological role of ROCKs in the cardiovascular systems," American Journal of Physiology: Cell Physiology (2006), vol. 290, pp. C661-C668.

Lin, Tong et al., "Rho-ROCK-LIMK-Cofilin Pathway Regulates Shear Stress Activation of Sterol Regulatory Element Binding Proteins," Circulation Research (2003), vol. 92, pp. 1296-1304.

Furukawa, Noboru et al., "Role of Rho-kinase in regulation of insulin action and glucose homeostasis," Cell Metabolism (2005), vol. 2, pp. 119-129.

Masumoto, Akihiro et al., "Suppression of Coronary Artery Spasm by the Rho-Kinase Inhibitor Fasudil in Patients With Vasospastic Angina," Circulation (2002), vol. 105, pp. 1545-1547.

Nakahara, Tsutomu et al., "Y-27632 potentiates relaxant effects of β2-adrenoceptor agonists in bovine tracheal smooth muscle," European Journal of Pharmacology (2000), vol. 389, pp. 103-106.

Pacaud, P. et al., "Rho proteins and vascular diseases," Archives des Maladies du Coeur et des Vaisseaux (2005), vol. 98, pp. 249-254.

Pommereau, Antje et al., "Two Simple and Generic Antibody-Independent Kinase Assays: Comparison of a Bioluminescent and a Microfluidic Assay Format," Journal of Biomedical Screening (2004), vol. 9, pp. 409-416.

Remington's Pharmaceutical Sciences 17th Edition (1985), p. 1418.

Retzer, Michaela et al., "Lysophosphatidic acid-induced platelet shape change proceeds via Rho/Rho kinase-mediated myosin light-chain and moesin phosphorylation," Cellular Signalling (2000), vol. 12, pp. 645-648.

Vicente-Manzanares, Miguel et al., "A Role for the Rho-p160 Rho Coiled-Coil Kinase Axis in the Chemokine Stromal Cell-Derived Factor-1α-Induced Lymphocyte Actomyosin and Microtubular Organization and Chemotaxis," The Journal of Immunology (2002), vol. 168, pp. 400-410.

Vicente-Manzanares, Miguel et al., "The RhoA Effector mDia is Induced During T Cell Activation and Regulates Actin Polymerization and Cell Migration in T Lymphocytes," The Journal of Immunology (2003), vol. 171, pp. 1023-1034.

Sandu, Oana A. et al., "Diabetes in the Goto-Kakizaki Rat is Accompanied by Impaired Insulin-Mediated Myosin-Bound Phosphatase Activation and Vascular Smooth Muscle Cell Relaxation," Diabetes (2000), vol. 49, pp. 2178-2189.

Sato, Motohiko et al., "Involvement of Rho-Kinase-Mediated Phosphorylation of Myosin Light Chain in Enhancement of Cerebral Vasospasm," Circulation Research (2000), vol. 87, pp. 195-200.

Satoh, Shin-Ichi et al., "Pharmacological profile of hydroxy fasudil as a selective rho kinase inhibitor on ischemic brain damage," Life Sciences (2001), vol. 69, pp. 1441-1453.

Setoguchi, Hidekazu et al., "Leukotriene C4 enhances the contraction of porcine tracheal smooth muscle through the activation of Y-27632, a rho kinase inhibitor, sensitive pathway," British Journal of Pharmacology (2001), vol. 132, pp. 111-118.

Shimokawa, Hiroaki et al., "Anti-anginal Effect of Fasudil, a Rho-Kinase Inhibitor, in Patients With Stable Effort Angina: A Multicenter Study," Journal of Cardiovascular Pharmacology (2002), vol. 40, pp. 751-761.

Steioff, Kerstin et al., "Long term Rho-kinase inhibition ameliorates endothelial dysfunction in LDL-Receptor deficient mice," European Journal of Pharmacology (2005), vol. 512, pp. 247-249.

Seasholtz, Tammy M. et al., "Rho and Rho Kinase Mediate Thrombin-Stimulated Vascular Smooth Muscle Cell DNA Synthesis and Migration," Circulation Research (1999), vol. 84, pp. 1186-1193.

Tatsumi, S. et al., "Involvement of Rho-Kinase in Inflammatory and Neuropathic Pain Through Phosphorylation of Myristoylated Alanine-Rich C-Kinase Substrate (Marcks)," Neuroscience (2005), vol. 131, pp. 491-498.

Forzato, Cristina et al., "Baker's yeast reduction of 4-hetero-2-(2-nitroethyl)cyclohexanones," Tetrahedron: Asymmetry (1997), vol. 8, pp. 1811-1820.

Uehata, Masayoshi et al., "Calcium sensitization of smooth muscle mediated by a Rho-associated protein kinase in hypertension," Nature (1997), vol. 389, pp. 990-994.

Yamakawa, Tadashi et al., "Involvement of Rho-Kinase in Angiotensin II-Induced Hypertrophy of Rat Vascular Smooth Muscle Cells," Hypertension (2000), vol. 35, pp. 313-318.

Yamamoto, Yasuhiro et al., "The Protein Kinase Inhibitor Fasudil Protects Against Ischemic Myocardial Injury Induced by Endothelin-1 in the Rabbit," Journal of Cardiovascular Pharmacology (2000), vol. 35, pp. 203-211.

Totsukawa, Go et al., "Distinct Roles of ROCK (Rho-kinase) and MLCK in Spatial Regulation of MLC Phosphorylation for Assembly of Stress Fibers and Focal Adhesions in 3T3 Fibroblasts," The Journal of Cell Biology (2000), vol. 150, pp. 797-806.

Yoshii, Akihiro et al., "Relaxation of Contracted Rabbit Tracheal and Human Bronchial Smooth Muscle by Y-27632 through Inhibition of Ca2+ Sensitization," American Journal of Respiratory Cell and Molecular Biology (1999), vol. 20, pp. 1190-1200.

Takami A. et al., "Design and Synthesis of Rho Kinase Inhibitors (I)", Bioorganic & Medicinal Chemistry 12:2115-2137 (2004).

International Search Report dated Oct. 4, 2006 received from the European Patent Office from related Application No. PCT/EP2006/005648.

* cited by examiner

ISOQUINOLINE DERIVATIVES

This application is a Divisional of U.S. patent application Ser. No. 11/961,193 filed Dec. 20, 2007, which is a Continuation of International Application No. PCT/EP2006/005648, filed Jun. 13, 2006, both of which are incorporated herein by reference in their entirety.

The present invention relates to novel isoquinoline derivatives, their preparation and their use in the treatment and/or prevention of diseases related to the inhibition of Rho-kinase and/or of Rho-kinase mediated phosphorylation of myosin light chain phosphatase.

Activation of a small GTPase RhoA upon agonist stimulation results in conversion of RhoA from the inactive GDP-bound form to the active GTP-bound form with a subsequent binding to and activation of Rho-kinase. Two isoforms, Rho-kinase 1 and Rho-kinase 2, are known. Rho-kinase 2 is expressed in vascular smooth muscle cells and endothelial cells. Activation of Rho-kinase 2 by the active GTP-bound RhoA leads to calcium sensitization of smooth muscle cells through phosphorylation-mediated inhibition of the myosin light chain phosphatase activity and thereby up-regulation of the activity of myosin regulatory light chain (Uehata et al., Nature 1997, 389, 990-994).

It is known that Rho-kinase is involved in vasoconstriction, including the development of myogenic tone (J. Appl. Physiol. 2005, 1940-8, 98), bronchial smooth muscle contraction (Am. J. Resp. Cell Mol. Biol. 20, 1190-1200), hypertension, i.e. pulmonary hypertension (Heart, 91, 391-2, 2005) and ocular hypertension (Invest. Ophthalmol. Visual Sci. 2001, 42, 137-144), endothelial dysfunction (Eur. J. Pharmacol. 2005, 512, 247-249), artherosclerosis, restenosis (Arch. Mal. Coeur 2005, 98, 249-254), glucose utilization, cardiac hypertrophy (Hypertension 2000, 35, 313-318), erectile dysfunction (Nature Medicine 2001, 7, 119-122), retinopathy, inflammation, immune diseases, AIDS, osteoporosis, brain functional disorder, infection of digestive tracts with bacteria (WO 98/06433), cancer development, vascular smooth muscle proliferation and motility (Circ. Res. 1999, 84, 1186-1193; Atherosclerosis 2001, 155, 321-327), endothelial proliferation and motility (Biochem. Biophys. Res. Commun. 2000, 269, 633-640), stress fiber formation (Science 1997, 275, 1308-1311; J. Cell Biol. 2000, 150, 797-806), platelet aggregation (FEBS Lett. 2000, 466, 70-74; Blood 1999, 94, 1665-1672), Na/H exchange transport system activation (EMBO J. 1998, 17, 4712-4722), Alzheimer's disease (Science 2003, 302, 1215-1217), adducin activation (J. Biol. Chem., 273, 5542-5548, 1998), and in SREB (Sterol response binding element) signalling and its effects on lipid metabolism (Circ. Res., 92, 1296-304, 2003).

Therefore, a compound having inhibitory effect on Rho-kinase and/or on Rho-kinase mediated phosphorylation of myosin light chain phosphatase is useful for the treatment and/or prevention of diseases involving Rho-kinase as the primary disease cause, e.g. hypertension, i.e., pulmonary hypertension and ocular hypertension, peripheral circulatory disorder, angina pectoris, cerebral vasospasm, asthma, premature birth, hyperaggregability of platelets, Peripheral Occlusive Arterial Disease (PAOD), Chronic Obstructive Pulmonary Disease (COPD), cancer development, and erectile dysfunction, or as the secondary disease cause, e.g. arteriosclerosis, ischemic organ failure (end organ damage), fibroid lung, fibroid liver, liver failure, fibroid kidney, renal glomerulosclerosis, kidney failure, organ hypertrophy, prostatic hypertrophy, complications of diabetes, blood vessel restenosis, atherosclerosis, cancer, cardiac hypertrophy, heart failure; ischemic diseases; inflammation; autoimmune diseases; AIDS, osteopathy such as osteoporosis, brain functional disorder, infection of digestive tracts with bacteria, sepsis, adult respiratory distress syndrome, retinopathy, glaucoma and Alzheimer's disease.

WO 01/64238 describes isoquinoline-5-sulfonamide derivatives optionally substituted by a —$(CH_2)_{1-6}$—O—$(CH_2)_{0-6}$—, a —$(CH_2)_{0-6}$—S—$(CH_2)_{0-6}$— or a —$(CH_2)_{0-6}$-linked heterocyclic group useful as neuroprotective agents.

JP 10087629 A describes isoquinoline derivatives useful for the treatment of infections caused by *Heliobacter pylori* such as for example gastritis or ulcer. The isoquinoline derivatives are preferably 5-substituted by X—[($C_1$-$C_6$)alkylene)]$_{0-1}$-Y wherein X may be oxygen and Y may be an aryl or a heterocyclic group.

Hagihara et al. (Bioorg. Med. Chem. 1999, 7, 2647-2666) disclose 6-benzyloxy-isoquinoline for the treatment of infections caused by *Heliobacter pylori*.

U.S. Pat. No. 5,480,883 generically discloses as EGF and/or PDGF receptor inhibitors useful for inhibiting cell proliferation compounds of the formula "Ar I-X-Ar II" wherein X may be $(CHR_1)_m$—Z—$(CHR_1)_n$, e.g. Z—$CH_2$, wherein Z may be O, $R_1$ is hydrogen or alkyl, Ar I may be among others an optionally substituted $C_{5-12}$ bicyclic heteroaryl ring system and Ar II may be among others an optionally substituted $C_{3-7}$ monocyclic saturated heterocyclic system.

WO 03/053330 describes isoquinoline derivatives of the formula

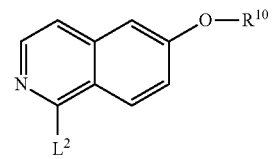

wherein $L^2$ is halogen and $R^{10}$ may be $C_{1-5}$alkylene-$C_{5-6}$heterocyclic group as intermediates in the synthesis of GSK-3 inhibitors.

An embodiment of the present invention is a compound of the formula (I)

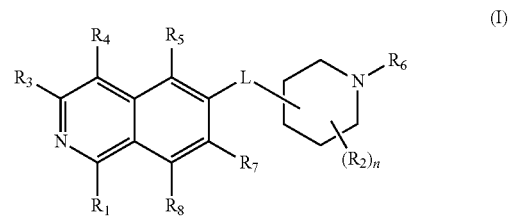

wherein
$R_1$ is
H,
$(C_1$-$C_6)$alkyl,
R',
NH—$(C_1$-$C_6)$alkyl,
NH—R', or
N[$(C_1$-$C_6)$alkyl]$_2$;
$R_2$ is hydrogen, halogen, or $(C_1$-$C_6)$alkyl;
$R_3$ is
H,
halogen,
$(C_1$-$C_6)$alkyl,
$(C_1$-$C_6)$alkylene-R', OH,
O—R'',
NH$_2$,
NHR'',
NR''R'' or
NH—C(O)—R'';
R$_4$ is
H,
halogen,
hydroxy,
CN,
(C$_1$-C$_6$)alkyl,
R',
(C$_1$-C$_6$)alkylene-R';
R$_5$ is
H,
halogen,
CN,
NO$_2$,
(C$_1$-C$_6$)alkyl,
(C$_2$-C$_6$)alkenyl,
R',
(C$_1$-C$_6$)alkylene-(C$_6$-C$_{10}$)aryl,
(C$_2$-C$_6$)alkenylene-(C$_6$-C$_{10}$)aryl,
(C$_1$-C$_6$)alkylene-(C$_5$-C$_{10}$)heterocyclyl,
CH(OH)—(C$_1$-C$_6$)alkyl,
NH$_2$,
NH—R',
NH—SO$_2$H,
NH—SO$_2$—(C$_1$-C$_6$)alkyl,
NH—SO$_2$—R',
NH—C(O)—(C$_1$-C$_6$)alkyl,
NH—C(O)—R',
C(O)N[(C$_1$-C$_6$)alkyl]$_2$,
C(O)OH, or
C(O)O—(C$_1$-C$_6$)alkyl;
R$_6$ is
H,
R',
(C$_1$-C$_8$)alkyl,
(C$_1$-C$_6$)alkylene-R',
(C$_1$-C$_6$)alkylene-O—(C$_1$-C$_6$)alkyl,
(C$_1$-C$_6$)alkylene-O—R',
(C$_1$-C$_6$)alkylene-CH[R']$_2$,
(C$_1$-C$_6$)alkylene-C(O)—R',
(C$_1$-C$_6$)alkylene-C(O)NH$_2$,
(C$_1$-C$_6$)alkylene-C(O)NH—R', or
(C$_1$-C$_6$)alkylene-C(O)N[R']$_2$;
R$_7$ is
H,
halogen,
CN,
NO$_2$,
(C$_1$-C$_6$)alkyl,
(C$_2$-C$_6$)alkenyl,
R',
(C$_2$-C$_6$)alkenylene-(C$_6$-C$_{10}$)aryl,
(C$_1$-C$_6$)alkylene-R',
CH(OH)—(C$_1$-C$_6$)alkyl,
CH(OH)—(C$_6$-C$_{10}$)aryl,
CH(OH)—(C$_5$-C$_{10}$)heterocyclyl,
NH$_2$,
NH—R',
NH—SO$_2$H,
NH—SO$_2$—(C$_1$-C$_6$)alkyl,
NH—SO$_2$—R',
SO$_2$—NH$_2$,
SO$_2$—NHR',
NH—C(O)—(C$_1$-C$_6$)alkyl,
NH—C(O)—R',
C(O)N[(C$_1$-C$_6$)alkyl]$_2$,
C(O)OH, or
C(O)O—(C$_1$-C$_6$)alkyl;
R$_8$ is H, halogen or (C$_1$-C$_6$)alkyl;
n is 1, 2, 3 or 4;
L is O or O—(C$_1$-C$_6$)alkylene;
R' is
(C$_3$-C$_8$)cycloalkyl,
(C$_5$-C$_{10}$)heterocyclyl,
(C$_6$-C$_{10}$)aryl; and
R'' is
(C$_3$-C$_8$)cycloalkyl,
(C$_5$-C$_{10}$)heterocyclyl,
(C$_6$-C$_{10}$)aryl,
(C$_1$-C$_6$)alkyl,
(C$_1$-C$_6$)alkylene-R',
(C$_1$-C$_6$)alkylene-O—(C$_1$-C$_6$)alkyl,
(C$_1$-C$_6$)alkylene-O—R', or
(C$_1$-C$_6$)alkylene-NR$_x$R$_y$; and
R$_x$ and R$_y$ are independently of each other
(C$_1$-C$_6$)alkyl,
(C$_5$-C$_{10}$)heterocyclyl,
(C$_6$-C$_{10}$)aryl,
(C$_1$-C$_4$)alkylene-(C$_5$-C$_{10}$)heterocyclyl,
(C$_1$-C$_4$)alkylene-(C$_6$-C$_{10}$)aryl,
(C$_1$-C$_4$)alkylene-NH(C$_1$-C$_6$)alkyl,
(C$_1$-C$_4$)alkylene-N[(C$_1$-C$_6$)alkyl]$_2$,
(C$_1$-C$_4$)alkylene-N[(C$_6$-C$_{10}$)aryl]$_2$, or
(C$_1$-C$_4$)alkylene-N[(C$_5$-C$_{10}$)heterocyclyl]$_2$; and
wherein in residues R$_4$, R$_5$, R$_7$ and R$_8$ one alkyl or alkylene hydrogen atom can optionally be substituted by OH, F, OCH$_3$, COOH, COOCH$_3$, NH$_2$, NHCH$_3$, N(CH$_3$)$_2$, CONH$_2$, CONHCH$_3$ or CON(CH$_3$)$_2$;
or a pharmaceutically acceptable salt thereof and/or a physiologically functional derivative thereof.

Preferably, R$_1$ is H, (C$_1$-C$_6$)alkyl, (C$_6$-C$_{10}$)aryl, NH—(C$_1$-C$_6$)alkyl, NH—(C$_6$-C$_{10}$)aryl or N[(C$_1$-C$_6$)alkyl]$_2$. More preferably, R$_1$ is H, halogen, (C$_1$-C$_4$)alkyl, NH—(C$_1$-C$_4$)alkyl, N[(C$_1$-C$_4$)alkyl]$_2$ or NH-phenyl. Most preferably, R$_1$ is H, (C$_1$-C$_2$)alkyl or NH—(C$_1$-C$_2$)alkyl, especially preferred H.

Preferably, R$_2$ is H, halogen or (C$_1$-C$_4$)alkyl. Preferably, R$_2$ is H or (C$_1$-C$_4$)alkyl. More preferred, R$_2$ is H, (C$_1$-C$_2$)alkyl. R$_2$ may be bound to any carbon atom of the piperidine ring including the position where the linker group L is bound.

R$_3$ is preferably H, halogen, (C$_1$-C$_4$)alkylene-R', O—R'' or NHR''. More preferred, R$_3$ is H or NHR''. Most preferred, R$_3$ is H, NH—(C$_5$-C$_6$)heterocyclyl or NH-phenyl, especially preferred are H, NH—(C$_5$-C$_6$)heteroaryl containing one or more N atoms or NH-phenyl. Most especially preferred, R$_3$ is H. Examples of R$_3$ substituents are

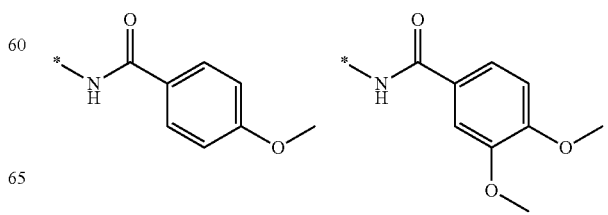

-continued
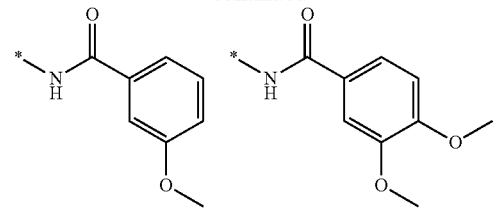
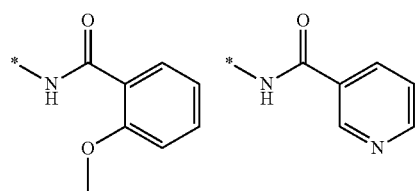
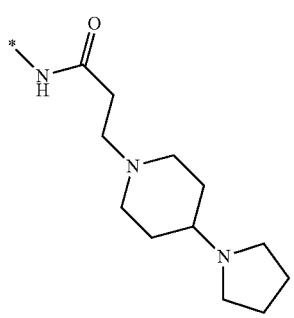
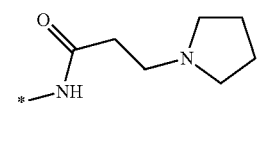
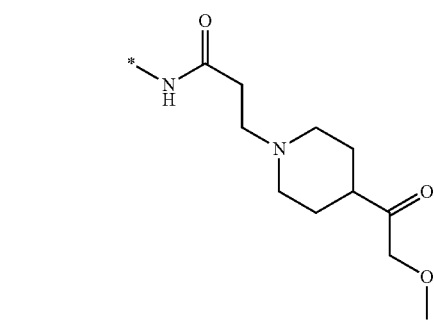
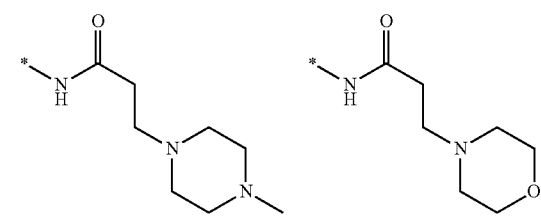
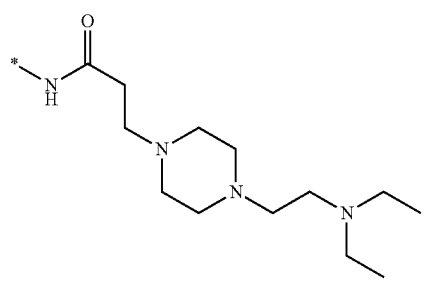
-continued
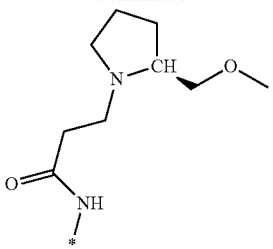
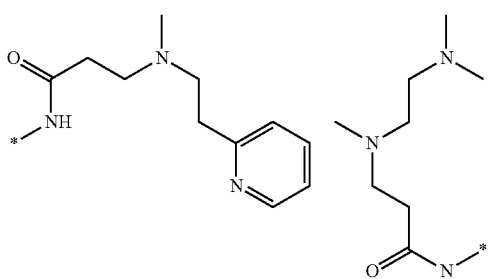
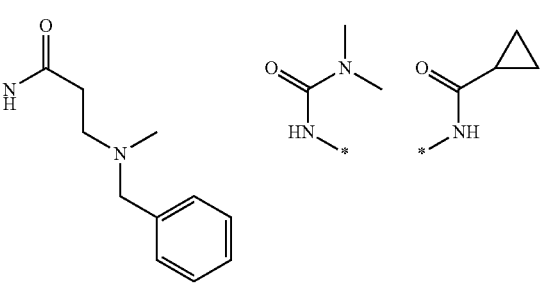
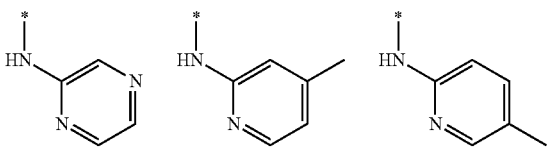
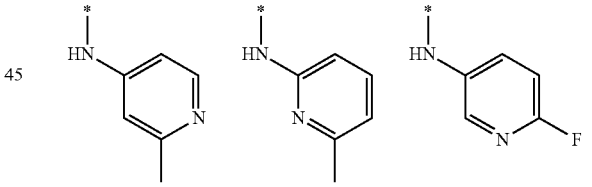
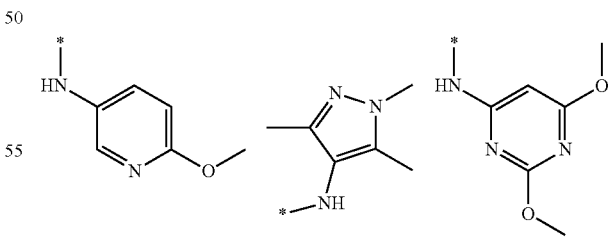
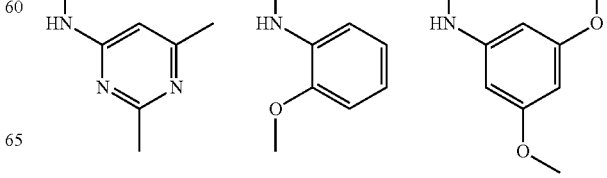

-continued
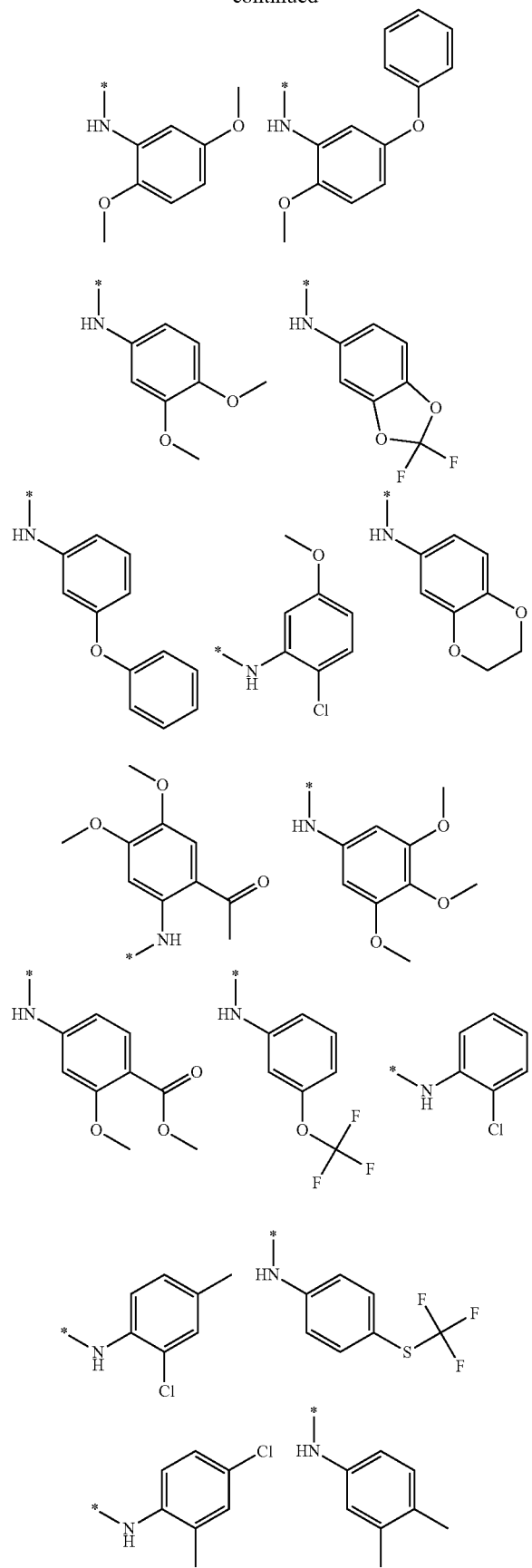
-continued
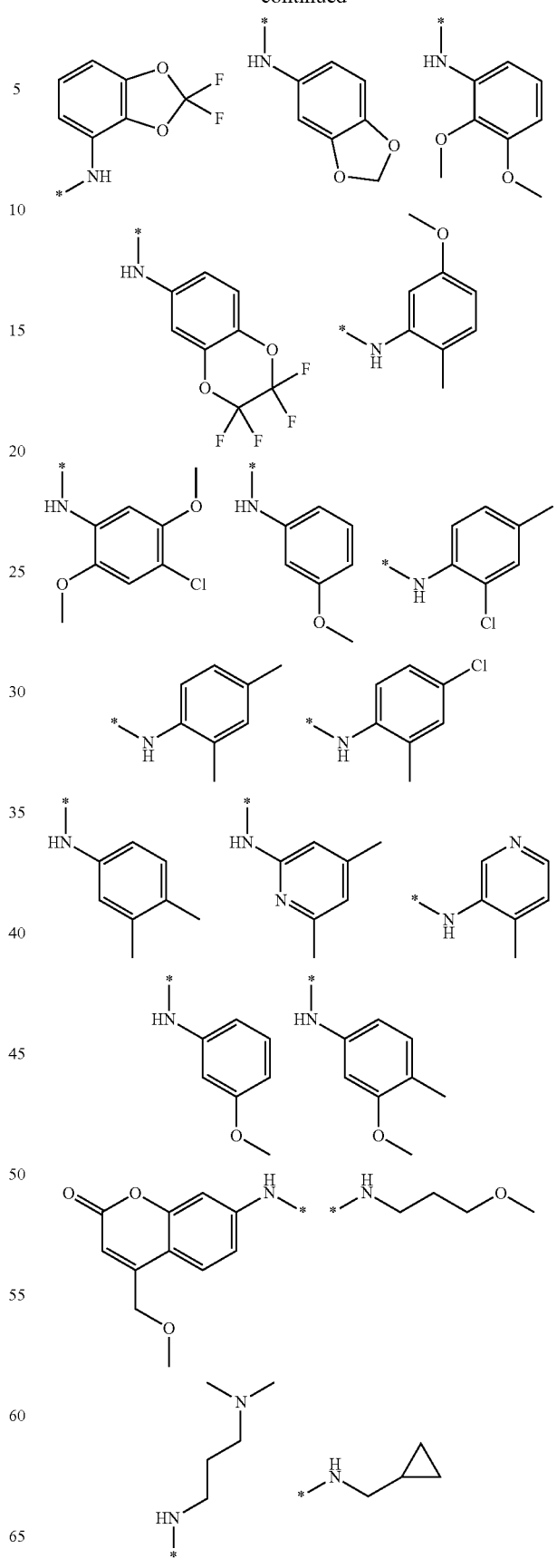

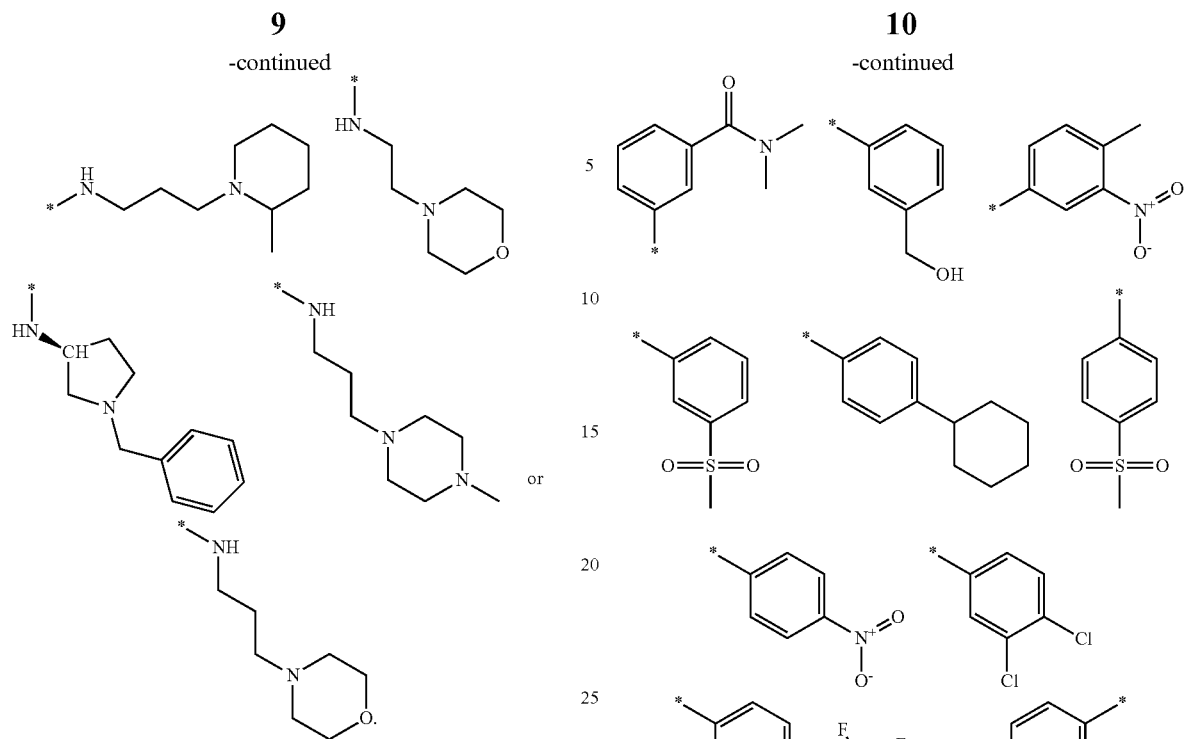

Preferably, $R_4$ is H, halogen or $(C_1-C_6)$alkyl. More preferred, $R_4$ is H, halogen or $(C_1-C_4)$alkyl. Most preferred, $R_4$ is H.

Preferably, $R_5$ is H, halogen, CN, $(C_1-C_6)$alkyl, R', NH—$(C_6-C_{10})$aryl or $(C_1-C_6)$alkylene-R'. More preferably, $R_5$ is H, halogen, $(C_1-C_6)$alkyl, R', NH—$(C_6-C_{10})$aryl or $(C_1-C_6)$alkylene-R'. Most preferably, $R_5$ is H, halogen, $(C_6-C_{10})$aryl, NH—$(C_6-C_{10})$aryl, $(C_1-C_2)$alkyl-$(C_6-C_{10})$aryl, $(C_1-C_6)$alkyl or $(C_5-C_{10})$heteroaryl. Especially preferred, $R_5$ is H, halogen, phenyl, $(C_1-C_6)$alkyl or $(C_5-C_6)$heteroaryl. Examples of $R_5$ are hydrogen, fluoro, chloro, bromo, iodo, nitrile, nitro, (p-methoxy)-phenyl, N-aniline, phenyl, benzyl, methyl, ethyl, vinyl, 2-propenyl, s-butenyl, cyclopropyl, thienyl, tetrazol, amino, 4-methoxy-anilin, N-acetyl or a substituent of the group consisting of

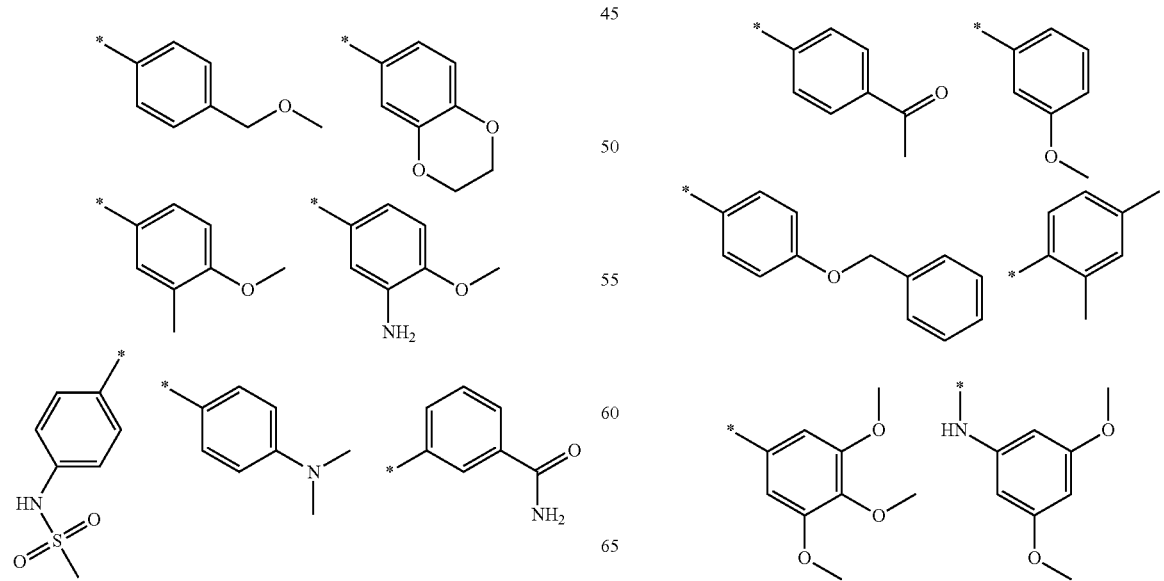

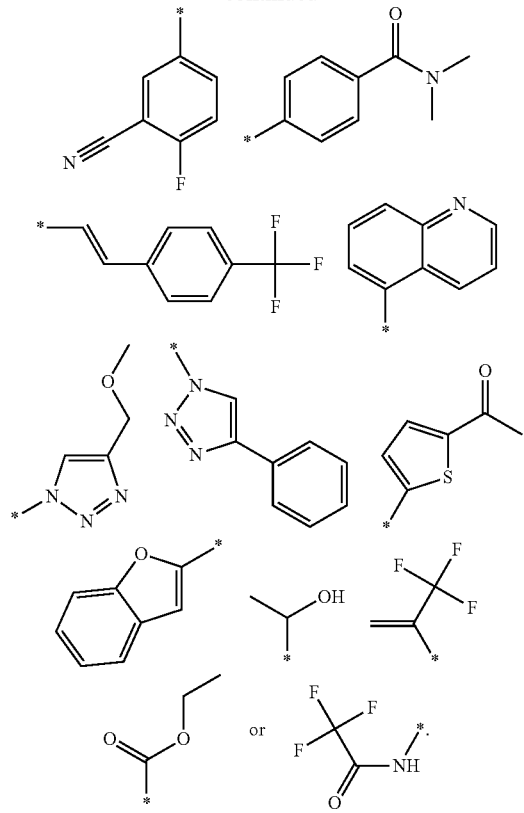

Preferably, $R_6$ is H, $(C_1-C_6)$alkyl, R', $(C_1-C_4)$alkylene-$(C_3-C_8)$cycloalkyl, $(C_1-C_4)$alkylene-$(C_5-C_{10})$heterocyclyl, $(C_1-C_4)$alkylene-C(O)—$(C_5-C_{10})$heterocyclyl, $(C_1-C_4)$alkylene-C(O)—$(C_6-C_{10})$aryl or $(C_1-C_6)$alkylene-$(C_6-C_{10})$aryl. More preferred, $R_6$ is H, $(C_1-C_6)$alkyl, $(C_5-C_{10})$heterocyclyl, $(C_1-C_4)$alkylene-$(C_5-C_{10})$heterocyclyl or $(C_1-C_6)$alkylene-$(C_6-C_{10})$aryl. Examples of $R_6$ are H, methyl, ethyl, propyl, butyl, s-butyl, pentyl, 3-methyl-butyl, isopropyl, trifluoromethyl, 3,3,3-trifluorobutyl, cyclopropyl, methylene cyclopropyl, 2-pyrimidinyl, benzyl or a substituent of the group consisting of

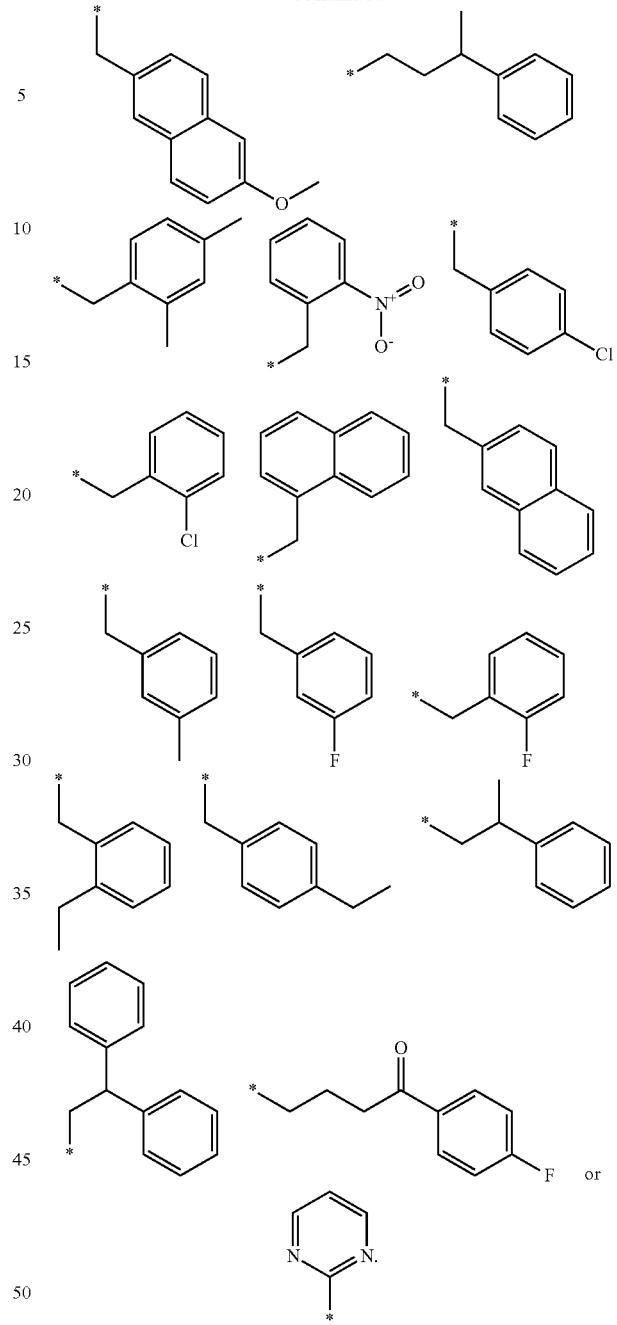

Preferably, $R_7$ is H, halogen, CN, $(C_1-C_6)$alkyl, $(C_2-C_6)$alkenyl, R' or $(C_1-C_6)$alkylene-$(C_3-C_8)$cycloalkyl. More preferred, $R_7$ is H, halogen, CN, $(C_1-C_4)$alkyl, $(C_1-C_4)$alkenyl, phenyl, cyclopropyl or $(C_5-C_6)$heteroaryl. Most preferably, $R_7$ is H, fluoro, chloro, bromo, methyl, ethyl, phenyl, nitrile, cyclopropyl, thienyl or vinyl.

$R_8$ is preferably H, halogen or $(C_1-C_4)$alkyl. More preferred, $R_8$ is H, Cl, F, methyl or ethyl.

Preferably, n is 1, 2 or 3. More preferred, n is 1.

The linker group L may be bound to the piperidine ring in any position via a piperidine ring carbon atom. In a preferred embodiment, L is attached to the 4-position of the piperidine ring

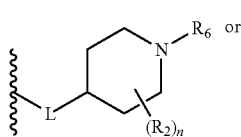

L is attached to the 3-position of the piperidine ring

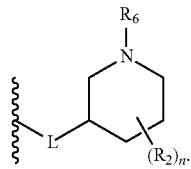

In an especially preferred embodiment, L is attached to the 4-position of the piperidine ring.

In a further preferred embodiment, L is O-methylene, O-ethylene or preferably O. More preferably, L is O-methylene, O-ethylene or O attached to the 4-position of the piperidine ring.

In preferred embodiments of the present invention one or more or all of the groups contained in the compounds of formula (I) can independently of each other have any of the preferred, more preferred or most preferred definitions of the groups specified above or any one or some of the specific denotations which are comprised by the definitions of the groups and specified above, all combinations of preferred definitions, more preferred or most preferred and/or specific denotations being a subject of the present invention. Also with respect to all preferred embodiments the invention includes the compounds of the formula (I) in all stereoisomeric forms and mixtures of stereoisomeric forms in all ratios, and their physiologically acceptable salts.

The term "*-" in the exemplified substituents vide supra marks the point where the substituent is attached, which means, for example, for a $R_3$ substituent

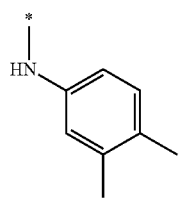

a compound of the formula

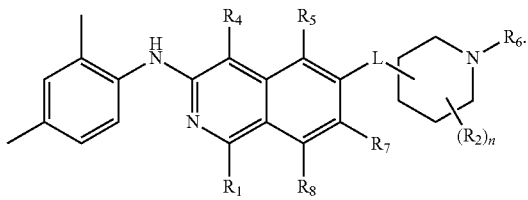

A preferred embodiment is a compound of the formula (I) wherein
$R_1$ is H, $(C_1-C_6)$alkyl, $(C_6-C_{10})$aryl, NH—$(C_1-C_6)$alkyl, NH—$(C_6-C_{10})$aryl, or N[$(C_1-C_6)$alkyl]$_2$;
$R_2$ is hydrogen, halogen, or $(C_1-C_6)$alkyl;
$R_3$ is H, halogen, $(C_1-C_4)$alkylene-R', O—R" or NHR", wherein R' and R" are defined as above;
$R_4$ is H, halogen or $(C_1-C_6)$alkyl;
$R_5$ is H, halogen, $(C_1-C_6)$alkyl, CN, $(C_6-C_{10})$aryl, NH—$(C_6-C_{10})$aryl, $(C_1-C_6)$alkylene-$(C_6-C_{10})$aryl, $(C_5-C_{10})$heterocyclyl or $(C_1-C_6)$alkylene-$(C_5-C_{10})$heterocyclyl;
$R_6$ is H, R', $(C_1-C_4)$alkylene-$(C_5-C_{10})$heterocyclyl, $(C_1-C_6)$alkylene-C(O)—$(C_6-C_{10})$aryl, $(C_1-C_4)$alkylene-C(O)—$(C_5-C_{10})$heterocyclyl, $(C_1-C_6)$alkylene-$(C_6-C_{10})$aryl or $(C_1-C_6)$alkyl.
$R_7$ is H, halogen, CN, $(C_1-C_6)$alkyl, $(C_2-C_6)$alkenyl or R';
$R_8$ is H, halogen or $(C_1-C_6)$alkyl;
n is 1, 2 or 3, and
L is O, O-methylene or O-ethylene;
or a pharmaceutically acceptable salt thereof and/or a physiologically functional derivative thereof.

A further preferred embodiment is a compound of the formula (I) wherein
$R_1$ is H, $(C_1-C_6)$alkyl, $(C_6-C_{10})$aryl, NH—$(C_1-C_6)$alkyl, NH—$(C_6-C_{10})$aryl, or N[$(C_1-C_6)$alkyl]$_2$;
$R_2$ is H or $(C_1-C_4)$alkyl;
$R_3$ is H, halogen or NHR", wherein R" is defined as above;
$R_4$ is H, halogen or $(C_1-C_4)$alkyl;
$R_5$ is H, halogen, $(C_1-C_6)$alkyl, $(C_6-C_{10})$aryl, NH—$(C_6-C_{10})$aryl, $(C_1-C_6)$alkylene-$(C_6-C_{10})$aryl or $(C_5-C_{10})$heterocyclyl;
$R_6$ is H, $(C_1-C_6)$alkyl, R', $(C_1-C_4)$alkylene-$(C_5-C_{10})$heterocyclyl or $(C_1-C_6)$alkylene-$(C_6-C_{10})$aryl;
$R_7$ is H, halogen, CN, $(C_1-C_6)$alkyl, $(C_2-C_6)$alkenyl or R';
$R_8$ is H, halogen or $(C_1-C_6)$alkyl;
n is 1, 2 or 3; and
L is O;
or a pharmaceutically acceptable salt thereof and/or a physiologically functional derivative thereof.

An especially preferred embodiment is a compound of the formula (I) wherein
$R_1$ is H, $(C_1-C_4)$alkyl, NH—$(C_1-C_4)$alkyl, N[$(C_1-C_4)$alkyl]$_2$ or NH-phenyl;
$R_2$ is H, $(C_1-C_4)$alkyl;
$R_3$ is H, NH—$(C_5-C_6)$heteroaryl or NH-phenyl;
$R_4$ is H, halogen or $(C_1-C_4)$alkyl;
$R_5$ is H, halogen, $(C_1-C_4)$alkyl, $(C_6-C_{10})$aryl, NH—$(C_6-C_{10})$aryl, $(C_1-C_2)$alkyl-$(C_6-C_{10})$aryl or $(C_5-C_{10})$heteroaryl;
$R_6$ is H, $(C_1-C_6)$alkyl, $(C_5-C_{10})$heterocyclyl, $(C_1-C_4)$alkylene-$(C_5-C_{10})$heterocyclyl, $(C_6-C_{10})$aryl or $(C_1-C_6)$alkylene-$(C_6-C_{10})$aryl;
$R_7$ is H, halogen, CN, $(C_1-C_4)$alkyl, $(C_1-C_4)$alkenyl, phenyl, cyclopropyl, $(C_5-C_6)$heteroaryl;
$R_8$ is H, halogen or $(C_1-C_4)$alkyl;
n is 1; and
L is O;
or a pharmaceutically acceptable salt thereof and/or a physiologically functional derivative thereof.

As in any embodiment of the invention, in the preceding embodiments which contain preferred, more preferred, most preferred or exemplary definitions of compounds according to the invention, one or more or all of the groups can have any of its preferred, more preferred, most preferred definitions specified above or any one or some of the specific denotations which are comprised by its definitions and are specified above.

Isoquinoline and piperidyl substitution pattern are numbered text according to IUPAC rules:

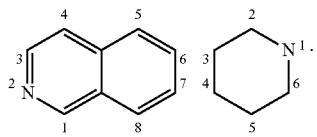

Physiologically acceptable salts of compounds of the formula (I) mean both their organic and inorganic salts as described in Remington's Pharmaceutical Sciences (17th edition, page 1418 (1985)). Because of the physical and chemical stability and the solubility, preference is given for acidic groups inter alia to sodium, potassium, calcium and ammonium salts; preference is given for basic groups inter alia to salts of maleic acid, fumaric acid, succinic acid, malic acid, tartaric acid, methylsulfonic acid, hydrochloric acid, sulfuric acid, phosphoric acid or of carboxylic acids or sulfonic acids, for example as hydrochlorides, hydrobromides, phosphates, sulfates, methanesulfonates, acetates, lactates, maleates, fumarates, malates, gluconates, and salts of amino acids, of natural bases or carboxylic acids. The preparation of physiologically acceptable salts from compounds of the formula (I) and (II) which are capable of salt formation, including their stereoisomeric forms, takes place in a manner known per se. The compounds of the formula (I) form stable alkali metal, alkaline earth metal or optionally substituted ammonium salts with basic reagents such as hydroxides, carbonates, bicarbonates, alcoholates and ammonia or organic bases, for example trimethyl- or triethylamine, ethanolamine, diethanolamine or triethanolamine, trometamol or else basic amino acids, for example lysine, ornithine or arginine. Where the compounds of the formula (I) have basic groups, stable acid addition salts can also be prepared with strong acids. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid.

Salts with a physiologically unacceptable anion such as, for example, trifluoroacetate likewise belong within the framework of the invention as useful intermediates for the preparation or purification of pharmaceutically acceptable salts and/or for use in nontherapeutic, for example in vitro, applications.

The term "physiologically functional derivative" used herein refers to any physiologically tolerated derivative of a compound of the formula (I) of the invention, for example an N-oxide, which on administration to a mammal such as, for example, a human is able to form (directly or indirectly) a compound of the formula (I) or an active metabolite thereof.

Physiologically functional derivatives include prodrugs of the compounds of the invention, as described, for example, in H. Okada et al., Chem. Pharm. Bull. 1994, 42, 57-61. Such prodrugs can be metabolized in vivo to a compound of the invention. These prodrugs may themselves be active or not.

The invention relates to compounds of the formula (I) in the form of their racemates, racemic mixtures and pure enantiomers and to their diastereomers and mixtures thereof.

If radicals or substituents may occur more than once in the compounds of the formula (I), they may all, independently of one another, have the stated meaning and be identical or different.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula (I)" hereinafter refer to compound(s) of the formula (I) as described above, and their physiologically acceptable salts, solvates and physiologically functional derivatives as described herein.

The terms $(C_1-C_2)$alkyl, $(C_1-C_4)$alkyl, $(C_1-C_6)$alkyl, $(C_1-C_8)$alkyl and the corresponding alkylene substituents are understood as a hydrocarbon residue which can be linear, i.e. straight-chain, or branched and has 1, 2, 3, 4, 5, 6, 7 or 8 carbon atoms, respectively. This also applies if an alkyl group occurs as a substituent on another group, for example in an alkoxy group (O-alkyl), S-alkyl or a —O$(C_1-C_6)$alkylene-O—, an alkoxycarbonyl group or an arylalkyl group. Examples of alkyl groups are methyl, ethyl, propyl, butyl, pentyl or hexyl, the n-isomers of all these groups, isopropyl, isobutyl, 1-methylbutyl, isopentyl, neopentyl, 2,2-dimethylbutyl, 2-methylpentyl, 3-methylpentyl, isohexyl, sec-butyl, tert-butyl or tert-pentyl. Alkyl groups may—if not otherwise stated—be halogenated once or more, i.e. alkyl groups may be fluorinated, i.e. perfluorinated. Examples of halogenated alkyl groups are $CF_3$ and $CH_2CF_3$, $OCF_3$, $SCF_3$, or —O—$(CF_2)_2$—O—.

Alkenyl are, for example, vinyl, 1-propenyl, 2-propenyl (=allyl), 2-butenyl, 3-butenyl, 2-methyl-2-butenyl, 3-methyl-2-butenyl, 5-hexenyl or 1,3-pentadienyl.

Alkynyl are, for example, ethynyl, 1-propynyl, 2-propynyl (=propargyl) or 2-butynyl.

Halogen means fluoro, chloro, bromo or iodo.

$(C_3-C_8)$cycloalkyl groups are cyclic alkyl groups containing 3, 4, 5, 6, 7 or 8 ring carbon atoms like cyclopropyl, cyclobutyl, cyclopentyl, cyclohexyl or cyclooctyl, which can also be substituted and/or contain 1 or 2 double bounds (unsaturated cycloalkyl groups) like, for example, cyclopentenyl or cyclohexenyl can be bonded via any carbon atom.

A $(C_6-C_{10})$aryl group means an aromatic ring or a ring system which comprises two aromatic rings which are fused or otherwise linked, for example a phenyl, naphthyl, biphenyl, tetrahydronaphthyl, alpha- or beta-tetralon-, indanyl- or indan-1-on-yl group. A preferred $(C_6-C_{10})$aryl group is phenyl.

A $(C_5-C_{10})$heterocyclyl group means a mono- or bicyclic ring system which comprises, apart from carbon, one or more heteroatoms such as, for example, e.g. 1, 2 or 3 nitrogen atoms, 1 or 2 oxygen atoms, 1 or 2 sulfur atoms or combinations of different hetero atoms. The heterocyclyl residues can be bound at any positions, for example on the 1-position, 2-position, 3-position, 4-position, 5-position, 6-position, 7-position or 8-position. $(C_5-C_{10})$heterocyclyl groups may be (1) aromatic (i.e., heteroaryl groups) or (2) saturated or (3) mixed aromatic/saturated.

Suitable $(C_5-C_{10})$heterocyclyl group include acridinyl, azocinyl, benzimidazolyl, benzofuryl, benzomorpholinyl, benzothienyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, furanyl, quinazolinyl, quinolinyl, 4H-quinolizinyl, quinoxalinyl, quinuclidinyl, chromanyl, chromenyl, chromen-2-onyl, cinnolinyl, decahydroquinolinyl, 2H,6H-1,5,2-dithiazinyl, dihydrofuro[2,3-b]-tetrahydrofuran, furyl, furazanyl, homomorpholinyl, homopiperazinyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, prolinyl, pteridinyl, purynyl, pyranyl, pyrazinyl, pyroazolidinyl, pyrazolinyl, pyrazolyl, pyridazinyl, pyridonyl, pyridooxazoles, pyridoimidazoles, pyridothiazoles, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, 6H-1,2,5-thiadazinyl, thiazolyl, 1,2,3-thiadiazolyl, 1,2,4-thiadiazolyl, 1,2,5-thiadiazolyl, 1,3,4-thiadiazolyl, thienyl, triazolyl, tetrazolyl and xanthenyl. Pyridyl stands both for 2-, 3- and 4-pyridyl. Thienyl stands both for 2- and 3-thienyl. Furyl stands both for 2- and 3-furyl. Also included are the corresponding N-oxides of these compounds, for example, 1-oxy-2-, 3- or 4-pyridyl.

Substitutions in $(C_5-C_{10})$heterocyclyl residues can occur on free carbon atoms or on nitrogen atoms.

Preferred examples of $(C_5-C_{10})$heterocyclyl residues are pyrazinyl, pyridyl, pyrimidinyl, pyrazolyl, morpholinyl, pyrrolidinyl, piperazinyl, piperidinyl, thienyl, benzofuryl, quinolinyl, tetrazolyl and triazolyl.

$(C_6-C_{10})$aryl and $(C_5-C_{10})$heterocyclyl groups are unsubstituted or substituted one or more times by suitable groups independently selected from halogen, $CF_3$, $NO_2$, $N_3$, CN, $C(O)$—$(C_1-C_6)$alkyl, $C(O)$—$(C_1-C_6)$aryl, COOH, $COO(C_1-C_6)$alkyl, $CONH_2$, $CONH(C_1-C_6)$alkyl, $CON[(C_1-C_6)alkyl]_2$, $(C_3-C_8)$cycloalkyl, $(C_1-C_6)$alkyl, $(C_1-C_6)$alkylene-OH, $(C_1-C_6)$alkylene-$NH_2$, $(C_1-C_6)$alkylene-$NH(C_1-C_6)$alkyl, $(C_1-C_6)$alkylene-$N[(C_1-C_6)alkyl]_2$, $(C_2-C_6)$alkenyl, $(C_2-C_6)$alkynyl, O—$(C_1-C_6)$alkyl, O—$C(O)$—$(C_1-C_6)$alkyl, O—$C(O)$—$(C_6-C_{10})$aryl, O—$C(O)$—$(C_5-C_{10})$heterocyclyl, $PO_3H_2$, $SO_3H$, $SO_2$—$NH_2$, $SO_2NH(C_1-C_6)$alkyl, $SO_2N[(C_1-C_6)alkyl]_2$, S—$(C_1-C_6)$alkyl; S—$(C_1-C_6)$alkylene-$(C_6-C_{10})$aryl, S—$(C_1-C_6)$alkylene-$(C_5-C_{10})$heterocyclyl, SO—$(C_1-C_6)$alkyl, SO—$(C_1-C_6)$alkylene-$(C_6-C_{10})$aryl, SO—$(C_1-C_6)$alkylene-$(C_5-C_{10})$heterocyclyl, $SO_2$—$(C_1-C_6)$alkyl, $SO_2$—$(C_1-C_6)$alkylene-$(C_6-C_{10})$aryl, $SO_2$—$(C_1-C_6)$alkylene-$(C_5-C_{10})$heterocyclyl, $SO_2$—$NH(C_1-C_6)$alkylene-$(C_6-C_{10})$aryl, $SO_2$—$NH(C_1-C_6)$alkylene-$(C_5-C_{10})$heterocyclyl, $SO_2$—$N[(C_1-C_6)$alkyl][$(C_1-C_6)$alkylene-$(C_6-C_{10})$aryl], $SO_2$—$N[(C_1-C_6)$alkyl][$(C_1-C_6)$alkylene-$(C_5-C_{10})$heterocyclyl], $SO_2$—$N[(C_1-C_6)$alkylene-$(C_6-C_{10})$aryl]_2$, $SO_2$—$N[(C_1-C_6)$alkylene-$(C_5-C_{10})$heterocyclyl]_2$, $C(NH)(NH_2)$, $NH_2$, NH—$(C_1-C_6)$alkyl, $N[(C_1-C_6)alkyl]_2$, NH—$C(O)$—$(C_1-C_6)$alkyl, NH—$C(O)O$—$(C_1-C_6)$alkyl, NH—$C(O)$—$(C_6-C_{10})$aryl, NH—$C(O)$—$(C_5-C_{10})$heterocyclyl, NH—$C(O)O$—$(C_6-C_{10})$aryl, NH—$C(O)O$—$(C_5-C_{10})$heterocyclyl, NH—$C(O)$—NH—$(C_1-C_6)$alkyl, NH—$C(O)$—NH—$(C_6-C_{10})$aryl, NH—$C(O)$—NH—$(C_5-C_{10})$heterocyclyl, NH—$SO_2$—$(C_1-C_6)$alkyl, NH—$SO_2$—$(C_6-C_{10})$aryl, NH—$SO_2$—$(C_5-C_{10})$heterocyclyl, $N(C_1-C_6)$alkyl-$C(O)$—$(C_1-C_6)$alkyl, $N(C_1-C_6)$alkyl-$C(O)O$—$(C_1-C_6)$alkyl, $N(C_1-C_6)$alkyl-$C(O)$—$(C_6-C_{10})$aryl, $N(C_1-C_6)$alkyl-$C(O)$-heterocyclyl, $N(C_1-C_6)$alkyl-$C(O)O$—$(C_6-C_{10})$aryl, $N(C_1-C_6)$alkyl-$C(O)O$—$(C_5-C_{10})$ heterocyclyl, $N(C_1-C_6)$alkyl-$C(O)$—NH—$(C_1-C_6)$alkyl], $N(C_1-C_6)$alkyl-$C(O)$—NH—$(C_6-C_{10})$aryl, $N(C_1-C_6)$alkyl-$C(O)$—NH—$(C_5-C_{10})$heterocyclyl, $N[(C_1-C_6)alkyl]$-$C(O)$—$N[(C_1-C_6)alkyl]_2$, $N[(C_1-C_6)alkyl]$-$C(O)$—$N[(C_1-C_6)alkyl]$-$(C_6-C_{10})$aryl, $N[(C_1-C_6)alkyl]$-$C(O)$—$N[(C_1-C_6)alkyl]$-$(C_5-C_{10})$heterocyclyl, $N[(C_1-C_6)alkyl]$-$C(O)$—$N[(C_6-C_{10})aryl]_2$, $N[(C_1-C_6)alkyl]$-$C(O)$—$N[(C_5-C_{10})heterocyclyl]_2$, $N[(C_6-C_{10})aryl]$-$C(O)$—$(C_1-C_6)$alkyl, $N[(C_5-C_{10})heterocyclyl]$-$C(O)$—$(C_1-C_6)$alkyl, $N[(C_6-C_{10})aryl]$-$C(O)O$—$(C_1-C_6)$alkyl, $N[(C_5-C_{10})heterocyclyl]$-$C(O)O$—$(C_1-C_6)$alkyl, N(aryl)-$C(O)$—$(C_6-C_{10})$aryl, $N[(C_5-C_{10})heterocyclyl]$-$C(O)$—$(C_6-C_{10})$aryl, $N[(C_6-C_{10})aryl]$-$C(O)O$—$(C_6-C_{10})$aryl, $N[(C_5-C_{10})heterocyclyl]$-$C(O)O$—$(C_6-C_{10})$aryl, $N[(C_6-C_{10})aryl]$-$C(O)$—NH—$(C_1-C_6)$alkyl, $N[(C_5-C_{10})heterocyclyl]$-$C(O)$—NH—$(C_1-C_6)$alkyl, N(aryl)-$C(O)$—NH—$(C_6-C_{10})$aryl, $N[(C_5-C_{10})heterocyclyl]$-$C(O)$—NH—$(C_6-C_{10})$aryl, $N[(C_6-C_{10})aryl]$-$C(O)$—$N[(C_1-C_6)alkyl]_2$, $N[(C_5-C_{10})heterocyclyl]$-$C(O)$—$N[(C_1-C_6)alkyl]_2$, $N[(C_6-C_{10})aryl]$-$C(O)$—$N[(C_1-C_6)alkyl]$-$(C_6-C_{10})$aryl, $N[(C_5-C_{10})heterocyclyl]$-$C(O)$—$N[(C_1-C_6)alkyl]$-$(C_6-C_{10})$aryl, $N[(C_6-C_{10})aryl]$-$C(O)$—$N[(C_6-C_{10})aryl]_2$, $N[(C_5-C_{10})heterocyclyl]$-$C(O)$—$N[(C_6-C_{10})aryl]_2$, $(C_6-C_{10})$aryl, $(C_1-C_6)$alkylene-$(C_6-C_{10})$aryl, O—$(C_1-C_6)$alkylene-$(C_6-C_{10})$aryl, $(C_5-C_{10})$heterocyclyl, $(C_1-C_6)$alkylene-$(C_5-C_{10})$heterocyclyl, O—$(C_1-C_6)$alkylene-$(C_5-C_{10})$heterocyclyl, wherein the $(C_6-C_{10})$aryl or $(C_5-C_{10})$heterocyclyl may be substituted one to 3 times by halogen, OH, $NO_2$, CN, O—$(C_1-C_6)$alkyl, $(C_1-C_6)$alkyl, $NH_2$, $NH(C_1-C_6)$alkyl, $N[(C_1-C_6)alkyl]_2$, $SO_2CH_3$, COOH, $C(O)O$—$(C_1-C_6)$alkyl, $CONH_2$, $(C_1-C_6)$alkylene-O—$(C_1-C_6)$alkyl, $(C_5-C_{10})$alkylene-O—$(C_6-C_{10})$aryl, O—$(C_1-C_6)$alkylene-$(C_6-C_{10})$aryl; or wherein $(C_6-C_{10})$aryl is vicinal substituted by a O—$(C_1-C_4)$alkylene-O group whereby a 5-8-membered ring is formed together with the carbon atoms the oxygen atoms are attached to. Aryl or heterocyclyl substituents of $(C_6-C_{10})$aryl and $(C_5-C_{10})$heterocyclyl groups may not be further substituted by an aryl or heterocyclyl containing group.

Preferred substituents for $(C_6-C_{10})$aryl groups are $(C_1-C_4)$alkyl, O—$(C_1-C_4)$alkyl, O-phenyl, $C(O)O$—$(C_1-C_6)$alkyl, C(O)OH, $C(O)$—$(C_1-C_4)$alkyl, halogen, $NO_2$, $SO_2NH_2$, CN, $SO_2$—$(C_1-C_4)$alkyl, NH—$SO_2$—$(C_1-C_4)$alkyl, $NH_2$, NH—$C(O)$—$(C_1-C_4)$alkyl, $(C_3-C_8)$cycloalkyl, $(C_1-C_4)$alkyl-OH, $C(O)N[(C_1-C_4)alkyl]_2$, $C(O)NH_2$, $N[(C_1-C_4)alkyl]_2$, $(C_2-C_4)$alkenylene-$(C_6-C_{10})$aryl, wherein the $(C_6-C_{10})$aryl may be further substituted by $(C_1-C_4)$alkyl, $(C_1-C_4)$alkylene-O—$(C_1-C_6)$alkyl, O—$(C_1-C_4)$alkyl-$(C_6-C_{10})$aryl, or may be vicinal substituted by a O—$(C_1-C_4)$alkylene-O group whereby a 5-8-membered ring is formed together with the carbon atoms the oxygen atoms are attached to.

In monosubstituted phenyl groups the substituent can be located in the 2-position, the 3-position or the 4-position, with the 3-position and the 4-position being preferred. If a phenyl group carries two substituents, they can be located in 2,3-position, 2,4-position, 2,5-position, 2,6-position, 3,4-position or 3,5-position. In phenyl groups carrying three substituents the substituents can be located in 2,3,4-position, 2,3,5-position, 2,3,6-position, 2,4,5-position, 2,4,6-position, or 3,4,5-position.

The above statements relating to phenyl groups correspondingly apply to divalent groups derived from phenyl groups, i.e. phenylene which can be unsubstituted or substituted 1,2-phenylene, 1,3-phenylene or 1,4-phenylene. The above statements also correspondingly apply to the aryl subgroup in arylalkylene groups. Examples of arylalkylene groups which can also be unsubstituted or substituted in the aryl subgroup as well as in the alkylene subgroup, are benzyl, 1-phenylethylene, 2-phenylethylene, 3-phenylpropylene, 4-phenylbutylene, 1-methyl-3-phenyl-propylene.

Preferred substituents for $(C_5-C_{10})$heterocyclyl groups are $(C_1-C_4)$alkyl, O—$(C_1-C_4)$alkyl, $(C_1-C_4)$alkylene-phenyl, halogen, $(C_1-C_4)$alkylene-O—$(C_1-C_4)$alkyl, $(C_5-C_{10})$heterocyclyl, $(C_1-C_4)$alkylene-$N[(C_1-C_4)alkyl]_2$, or $(C_6-C_{10})$aryl, wherein the $(C_6-C_{10})$aryl may be further substituted by $(C_1-C_4)$alkyl, $(C_1-C_4)$alkylene-O—$(C_1-C_6)$alkyl, O—$(C_1-C_6)$alkyl-$(C_6-C_{10})$aryl, or may be vicinal substituted by a O—$(C_1-C_4)$alkylene-O group whereby a 5-8-membered ring is formed together with the carbon atoms the oxygen atoms are attached to.

The general and preferred substituents of $(C_6-C_{10})$aryl and $(C_5-C_{10})$heterocyclyl groups may be combined with the general and preferred definitions of $R_1$, $R_2$, $R_3$, $R_4$, $R_5$, $R_6$, $R_7$, $R_8$, n and L as described above.

The present invention therefore also relates to the compounds of the formula (I) and/or their physiologically acceptable salts and/or their prodrugs for use as pharmaceuticals (or medicaments), to the use of the compounds of the formula (I) and/or their physiologically acceptable salts and/or their prodrugs for the production of pharmaceuticals for the treatment and/or prevention of diseases associated with Rho-kinase and/or Rho-kinase mediated phosphorylation of myosin light chain phosphatase, i.e. for the treatment and/or prevention of hypertension, i.e. pulmonary hypertension and ocular hypertension, peripheral circulatory disorder, angina pectoris, cerebral vasospasm, asthma, premature birth, hyperaggregability of platelets, Peripheral Occlusive Arterial Disease (PAOD), Chronic Obstructive Pulmonary Disease (COPD), cancer development, erectile dysfunction, arteriosclerosis, ischemic organ failure (end organ damage), fibroid lung, fibroid liver, liver failure, fibroid kidney, renal glomerulosclerosis, kidney failure, organ hypertrophy, prostatic hypertrophy, complications of diabetes, blood vessel restenosis, atherosclerosis, cancer, cardiac hypertrophy, heart failure; ischemic diseases; inflammation; autoimmune diseases; AIDS, osteopathy such as osteoporosis, brain functional disorder, infection of digestive tracts with bacteria, sepsis, adult respiratory distress syndrome, retinopathy, glaucoma and Alzheimer's disease.

The present invention furthermore relates to pharmaceutical preparations (or pharmaceutical compositions) which contain an effective amount of at least one compound of the formula (I) and/or its physiologically acceptable salts and/or its prodrugs and a pharmaceutically acceptable carrier, i.e. one or more pharmaceutically acceptable carrier substances (or vehicles) and/or additives (or excipients).

The pharmaceuticals can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions or tinctures, or in other ways, for example in the form of aerosols or nasal sprays.

The pharmaceutical preparations according to the invention are prepared in a manner known per se and familiar to one skilled in the art, pharmaceutically acceptable inert inorganic and/or organic carrier substances and/or additives being used in addition to the compound(s) of the formula (I) and/or its (their) physiologically acceptable salts and/or its (their) prodrugs. For the production of pills, tablets, coated tablets and hard gelatin capsules it is possible to use, for example, lactose, corn starch or derivatives thereof, talc, stearic acid or its salts, etc. Carrier substances for soft gelatin capsules and suppositories are, for example, fats, waxes, semisolid and liquid polyols, natural or hardened oils, etc. Suitable carrier substances for the production of solutions, for example injection solutions, or of emulsions or syrups are, for example, water, saline, alcohols, glycerol, polyols, sucrose, invert sugar, glucose, vegetable oils, etc. Suitable carrier substances for microcapsules, implants or rods are, for example, copolymers of glycolic acid and lactic acid. The pharmaceutical preparations normally contain about 0.5 to about 90% by weight of the compounds of the formula (I) and/or their physiologically acceptable salts and/or their prodrugs. The amount of the active ingredient of the formula (I) and/or its physiologically acceptable salts and/or its prodrugs in the pharmaceutical preparations normally is from about 0.5 to about 1000 mg, preferably from about 1 to about 500 mg.

In addition to the active ingredients of the formula (I) and/or their physiologically acceptable salts and/or prodrugs and to carrier substances, the pharmaceutical preparations can contain one or more additives such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formula (I) and/or their physiologically acceptable salts and/or their prodrugs. In case a pharmaceutical preparation contains two or more compounds of the formula (I) the selection of the individual compounds can aim at a specific overall pharmacological profile of the pharmaceutical preparation. For example, a highly potent compound with a shorter duration of action may be combined with a long-acting compound of lower potency. The flexibility permitted with respect to the choice of substituents in the compounds of the formula (I) allows a great deal of control over the biological and physicochemical properties of the compounds and thus allows the selection of such desired compounds. Furthermore, in addition to at least one compound of the formula (I) and/or its physiologically acceptable salts and/or its prodrugs, the pharmaceutical preparations can also contain one or more other therapeutically or prophylactically active ingredients.

When using the compounds of the formula (I) the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches well known in the medical art. In general, the daily dose for achieving the desired results in an adult weighing about 75 kg is from about 0.01 to about 100 mg/kg, preferably from about 0.1 to about 50 mg/kg, in particular from about 0.1 to about 10 mg/kg, (in each case in mg per kg of body weight). The daily dose can be divided, in particular in the case of the administration of relatively large amounts, into several, for example 2, 3 or 4, part administrations. As usual, depending on individual behavior it may be necessary to deviate upwards or downwards from the daily dose indicated.

Furthermore, the compounds of the formula (I) can be used as synthesis intermediates for the preparation of other compounds, in particular of other pharmaceutical active ingredients, which are obtainable from the compounds of the formula I, for example by introduction of substituents or modification of functional groups.

The compounds of the formula (I) can be prepared according to the following exemplified compounds without limiting the scope of the claims.

In general, protective groups that may still be present in the products obtained in the coupling reaction are then removed by standard procedures. For example, tert-butyl protecting groups, in particular a tert-butoxycarbonyl group which is a protected form of an amidino group, can be deprotected, i.e. converted into the amidino group, by treatment with trifluoroacetic acid. As already explained, after the coupling reaction also functional groups can be generated from suitable precursor groups. In addition, a conversion into a physiologically acceptable salt or a prodrug of a compound of the formula (I) can then be carried out by known processes.

In general, a reaction mixture containing a final compound of the formula (I) or an intermediate is worked up and, if desired, the product is then purified by customary processes known to those skilled in the art. For example, a synthesized compound can be purified using well known methods such as crystallization, chromatography or reverse phase-high performance liquid chromatography (RP-HPLC) or other methods of separation based, for example, on the size, charge or hydrophobicity of the compound. Similarly, well known methods such as amino acid sequence analysis, NMR, IR and mass spectrometry (MS) can be used for characterizing a compound of the invention.

It is understood that modifications that do not substantially affect the activity of the various embodiments of this invention are included within the invention disclosed herein. Accordingly, the following examples are intended to illustrate but not limit the present invention.

LCMS Methods
Method #1
Column: YMC J'shere 33×2 4 µm
gradient (AcN+0.05% TFA): H2O+0.05% TFA; 5:95 (0 min) to 95:5 (2.5 min) to 95:5 (3 min)
Method #2
Column: YMC J'shere 33×2 4 µm
gradient (AcN+0.05% TFA): H2O+0.05% TFA, 5:95 (0 min) to 95:5 (3.4 min) to 95:5 (4.4 min)
Method #3
Column: YMC J'shere 33×2 4 µm
gradient AcN+0.08% FA: H2O+0.1% FA; 5:95 (0 min) to 95:5(2.5 min) to 95:5(3 min)
Method #Top
Column: YMC YMC J'sphere ODS H80 20×2 1 4µ
gradient 0 min 96% H2O (0.05% TFA) 2.0 min-95% ACN; 95% ACN bis 2.4 min; 4% ACN 2.45 min
Building Block Syntheses 7-Bromo-isoquinoline-6-ol (1)

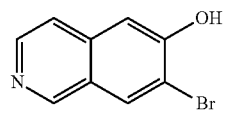

25 g (116.3 mmol) of 3-bromo-4-methoxybenzaldehyde, 19.0 mL (18.3 g, 174.5 mmol) of aminoacetaldehyde dimethyl acetal and 250 mL of toluene were heated to reflux for 6 h using a Dean-Stark apparatus. Solvent and excess reagent were distilled off and the crude product (approx. 37 g) was used for the next step without any additional purification.

The imine was dissolved in 240 mL of THF. 11.1 mL (12.6 g, 116.3 mmol) of ethyl chloroformate were added dropwise at 0° C. After stirring for 5 minutes 24.3 mL (23.2 g, 139.2 mmol) triethylphosphite were added dropwise. The mixture was stirred for 18 h at room temperature. Then the solvents were distilled off. Excess reagent was removed by repeated addition of 100 ml toluene and evaporation of the solvents. The P,N-acetal (approx. 62 g) was used for the next step without any additional purification.

The P,N-acetal, 51.3 mL (88.2 g, 465.2 mmol) titanium tetrachloride and 300 mL chloroform were heated to reflux for 48 h. The mixture was poured on ice and the pH was adjusted to 9 by using aqueous ammonia. Repeated extraction with ethyl acetate followed by removal of the solvents gave 14.8 g (53%) of 7-bromo-6-methoxyisoquinoline.

$^1$H-NMR (d$_6$-DMSO): δ=9.16 (1H, s), 8.46 (1H, d, J=5.9 Hz), 8.46 (1H, s), 7.76 (1H, d, J=5.9 Hz), 7.51 (1H, s), 4.01 (3H, s).
MS: m/z=238 (MH$^+$).

3.6 mL (9.5 g, 37.8 mmol) of BBr$_3$ were added at 0° C. to a solution of 4.5 g (18.9 mmol) 7-bromo-6-methoxy isoquinoline in 30 mL dichloromethane and stirred for 18 h at room temperature. Aqueous NaHCO$_3$-solution was added to adjust the pH to 8. Extraction with chloroform/isopropanol (3/1) followed by drying over sodium sulfate and removal of the solvents gave 2.7 g (64%) of compound 1.

$^1$H-NMR (d$_6$-DMSO): δ=9.19 (1H, s), 8.49 (1H, s), 8.38 (1H, d, J=6.1 Hz), 7.78 (1H, d, J=6.1 Hz), 7.34 (1H, s).
MS: m/z=224 (MH$^+$).

The following intermediates were synthesized using this procedure:

8-Fluoro-isoquinoline-6-ol (2)

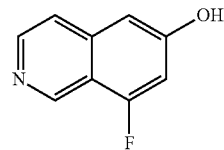 [SMILES: Oc1cc(F)c2cnccc2c1]

$^1$H-NMR (d$_6$-DMSO): δ=10.84 (1H, s), 9.21 (1H, s), 8.40 (1H, d, J=5.8 Hz), 7.67 (1H, d, J=5.8 Hz), 7.01 (2H, m).
MS: m/z=164 (MH$^+$).

7-Fluoro-isoquinoline-6-ol (3)

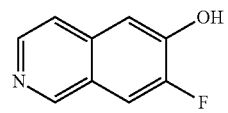

$^1$H-NMR (d$_6$-DMSO): δ=11.06 (1H, s), 9.07 (1H, s), 8.33 (1H, d, J=5.6 Hz), 7.88 (1H, d, J=11.4 Hz), 7.64 (1H, d, J=5.6 Hz), 7.31 (1H, d, J=8.6 Hz).
MS: m/z=164 (MH$^+$).

8-Methyl-isoquinoline-6-ol (4)

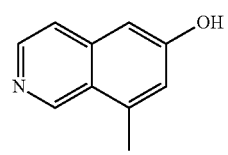

$^1$H-NMR (d$_6$-DMSO): δ=11.55 (1H, s), 9.47 (1H, s), 8.42 (1H, d, J=6.5 Hz), 8.11 (1H, d, J=6.5 Hz), 7.31 (1H, s), 7.25 (1H, s), 2.76 (3H, s).
MS: m/z=160 (MH$^+$).

7,8-Dimethyl-isoquinoline-6-ol (5)

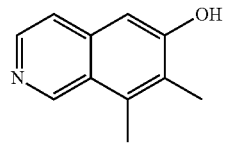

$^1$H-NMR (d$_6$-DMSO): δ=11.87 (1H, s), 9.58 (1H, s), 8.41 (1H, d, J=6.5 Hz), 8.18 (1H, d, J=6.5 Hz), 7.35 (1H, s), 7.25 (1H, s), 2.71 (3H, s), 2.35 (3H, s).
MS: m/z=174 (MH$^+$).

5,8-Dimethyl-isoquinoline-6-ol (6)

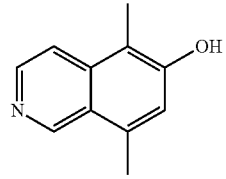

$^1$H-NMR (d$_6$-DMSO): δ=11.55 (1H, s), 9.52 (1H, s), 8.47 (1H, d, J=6.8 Hz), 8.26 (1H, d, J=6.8 Hz), 7.42 (1H, s), 2.76 (3H, s), 2.42 (3H, s).
MS: m/z=174 (MH$^+$).

6-Hydroxy-isoquinoline (7)

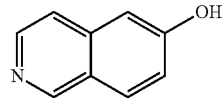

LCMS Method #1, retention time 0.14 min, detected mass 146.08 [M+H]$^+$

5-Chloroisoquinoline-6-ol (8)

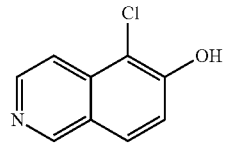 [SMILES: Oc1ccc2cnccc2c1Cl]

0.61 mL (1.02 g, 7.6 mmol) of sulfuryl chloride were added to a solution of 1.0 g (6.9 mmol) of compound 7 in 30 mL of dichloromethane. Three drops diethyl ether were added and the reaction was stirred at room temperature for 5 h. The solvents were removed by distillation and the remainder was treated with aqueous NaHCO$_3$ solution. The precipitate was filtered, washed with water and dried to give 1.1 g (89%) of compound 8 as a green-yellow solid.

$^1$H-NMR (d$_6$-DMSO): δ=11.37 (1H, s), 9.18 (1H, s), 8.50 (1H, d, J=6 Hz), 8.00 (1H, d, J=8.8 Hz), 7.83 (1H, J=6 Hz), 7.44 (1H, d, J=8.7 Hz).
MS: m/z=180 (MH$^+$).

5-Bromoisoquinoline-6-ol (9)

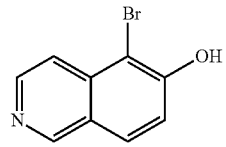 [SMILES: Oc1ccc2cnccc2c1Br]

7.9 mL (19.18 g, 120 mmol) of bromine were added dropwise to a suspension of 17.42 g (120 mmol) of compound 7 in 250 mL of chloroform at room temperature. After stirring for 2 h ethyl acetate was added. The precipitate was filtered, washed with ethyl acetate and dried. Aqueous NaHCO$_3$ solution was added carefully. The precipitate was filtered and washed with NaHCO$_3$ solution until the filtrate had a pH of 8. Drying gave 23.78 g (88%) of compound 9 as an off-white solid.

$^1$H-NMR (d$_6$-DMSO): δ=11.30 (1H, s), 9.13 (1H, s), 8.48 (1H, d, J=5.9 Hz), 8.02 (1H, d, J=8.8 Hz), 7.78 (1H, J=5.9 Hz), 7.40 (1H, d, J=8.8 Hz).
MS: m/z=224 (MH$^+$).

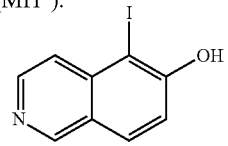

5-Iodoisoquinoline-6-ol (10)

Under argon atmosphere 1.77 g (12.2 mmol) of compound 7 were added to a solution of 5.0 g (13.5 mmol) bis(pyridin) iodonium tetrafluoroborate in 100 mL of dry dichloromethane. A solution of 2.4 mL (4 g, 26.8 mmol) trifluoromethane sulfonic acid in 20 mL dry dichloromethane was added dropwise at 0° C. and the mixture was stirred for 3 hours at room temperature. The solvents were removed by distillation and the remainder was treated with aqueous NaHCO$_3$ solution. The precipitate was filtered, washed with water and dried to yield 3.2 g (97%) of compound 10 as a beige solid.

$^1$H-NMR (d$_6$-DMSO): δ=9.09 (1H, s), 8.47 (1H, d, J=6.1 Hz), 8.04 (1H, d, J=8.8 Hz), 7.76 (1H, J=6.1 Hz), 7.37 (1H, d, J=8.8 Hz).
MS: m/z=272 (MH$^+$).

4-(5-Bromo-isoquinolin-6-yloxy)-piperidine-1-carboxylic acid tert-butyl ester (11)

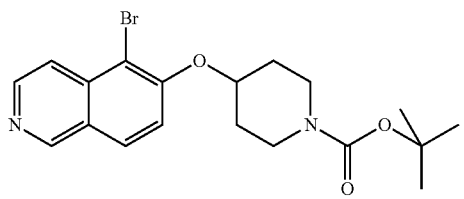 [SMILES: CC(C)(C)OC(=O)N1CCC(Oc2ccc3cnccc3c2Br)CC1]

3.75 mL (4.15 g, 23.8 mmol) of diethyl azo dicarboxylate were added to 12.7 g (19.9 mmol) of polymer-bound triphenylphosphine (PS—PPh$_3$, approx. 1.6 mmol/g, Argonaut) in 250 mL of dichloromethane at 0° C. and stirred for 15 min. 4.45 g (19.9 mmol) 5-bromo isoquinoline-6-ol (9), 4.0 g (19.9 mmol) Boc-(4-hydroxy)piperidine and 4.1 mL (3.0 g, 29.8 mmol) triethyl amine were added. The mixture was shaken for 16 h. The polymer was removed by filtration through Celite and the solvents were distilled off. 20 mL dichloromethane were added and the precipitate was isolated by filtration. The crude product (8 g) was purified by flash chromatography using ethyl acetate/n-heptane as eluent to give 4.78 g (60%) of compound 11.

$^1$H-NMR (d$_6$-DMSO): δ=9.24 (1H, s), 8.97 (1H, s), 8.56 (1H, d, J=6 Hz), 8.20 (1H, d, J=9 Hz), 7.85 (1H, d, J=6 Hz), 7.75 (1H, d, J=9 Hz), 5.02 (1H, m), 3.58 (2H, m), 3.40 (2H, m), 1.91 (2H, m), 1.70 (2H, m), 1.41 (9H, s).
MS: m/z=407 (MH$^+$).

The following building blocks were synthesized according to this method:

4-(5-Iodo-isoquinoline-6-yloxy)-piperidin-1-carboxylic acid tert-butyl ester (12)

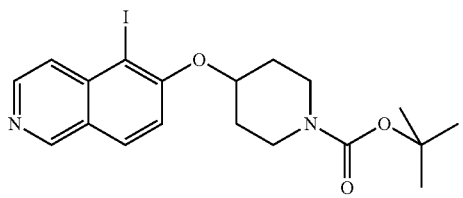 [SMILES: CC(C)(C)OC(=O)N1CCC(Oc2ccc3cnccc3c2I)CC1]

using compound 10 as starting material

¹H-NMR (CDCl₃): δ=9.04 (1H, s), 8.55 (1H, d, J=6 Hz), 7.93 (1H, d, J=9 Hz), 7.86 (1H, d, J=6 Hz), 7.27 (1H, d, J=9 Hz), 4.87 (1H, m), 3.66 (4H, m), 1.93 (4H, m), 1.48 (9H, s).

MS: m/z=455 (MH⁺).

4-(7-Bromo-isoquinoline-6-yloxy)-piperidin-1-carboxylic acid tert-butyl ester (13)

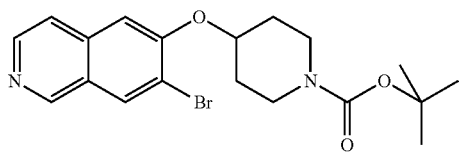 [SMILES: CC(C)(C)OC(=O)N1CCC(Oc2cc3ccncc3cc2Br)CC1]

using compound 1 as starting material

LCMS Method #4, retention time 1.13 min, detected mass 407.4 [M+H]⁺

4-[5-(4,4,5,5-Tetramethyl-[1,3,2]dioxaborolan-2-yl)-isoquinoline-6-yloxy]-piperidin-1-carboxylic acid tert-butyl ester (14)

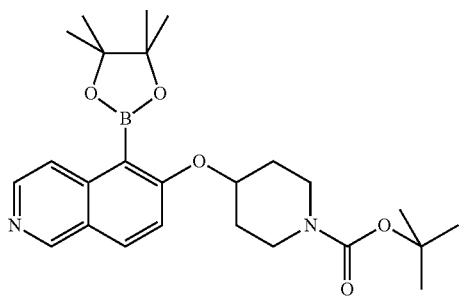 [SMILES: CC(C)(C)OC(=O)N1CCC(Oc2ccc3cnccc3c2B2OC(C)(C)C(C)(C)O2)CC1]

A solution of 0.55 g (1.34 mmol) 4-(5-bromo-isoquinolin-6-yloxy)-piperidine-1-carboxylic acid tert-butyl ester (11) in 14 mL of DMSO was added to a mixture of 1.0 g (4.0 mmol) bis(pinacolato)diboron, 0.78 g (8.0 mmol) K₂CO₃ and 29 mg (0.03 eq.) Pd(dppf)Cl₂. Argon was bubbled through the mixture for 30 min and then the reaction mixture was heated in a microwave reactor (CEM Discovery) to 100° C. for 60 min. After cooling to room temperature water was added. The mixture was extracted with ethyl acetate. After removal of the solvent the product was isolated by flash chromatography (ethyl acetate/n-heptane) to yield: 269 mg (44%) of compound 14 as a white solid. LCMS Method #4, retention time 1.30 min, detected mass 433.3 [M+H]⁺

4-(5-Cyano-isoquinolin-6-yloxy)-piperidine-1-carboxylic acid tert-butyl ester (15)

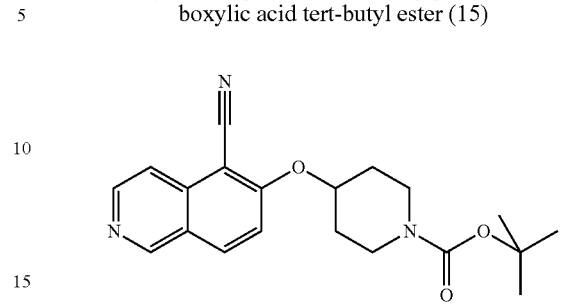

Under argon atmosphere 47 mg (0.4 mmol) of Zn(CN)₂ and 23 mg of (0.02 eq) Pd(PPh₃)₄ were added to a solution 62 mg (0.4 mmol) of 4-(5-bromo-isoquinolin-6-yloxy)-piperidine-1-carboxylic acid tert-butyl ester (11) in DMF. The reaction was heated for 5 minutes to 150° C. in a microwave reactor (CEM Discovery). After cooling to room temperature water and ethyl acetate were added. The mixture was filtered through celite, washed with ethyl acetate and concentrated to yield 176 mg of compound 15.

MS: m/z=354 (MH⁺).

4-(7-Cyano-isoquinolin-6-yloxy)-piperidine-1-carboxylic acid tert-butyl ester (16)

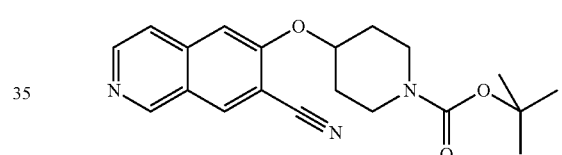

Under argon atmosphere 35 mg (0.3 mmol) of Zn(CN)₂ and 17 mg (0.05 eq) of Pd(PPh₃)₄ were added to a solution of 122 mg (0.3 mmol) of 4-(7-bromo-isoquinolin-6-yloxy)-piperidine-1-carboxylic acid tert-butyl ester (13) in DMF. The reaction was heated for 5 minutes to 150° C. in a microwave reactor (CEM Discovery). After cooling to room temperature water and ethyl acetate were added. The mixture was filtered through Celite, washed with ethyl acetate and concentrated. The crude product was purified by preparative HPLC to yield 77 mg of compound 16.

LCMS Method #4, retention time 1.06 min, detected mass 354.5 [M+H]⁺

4-(5-Azido-isoquinoline-6-yloxy)-piperidin-1-carboxylic acid tert-butyl ester (17)

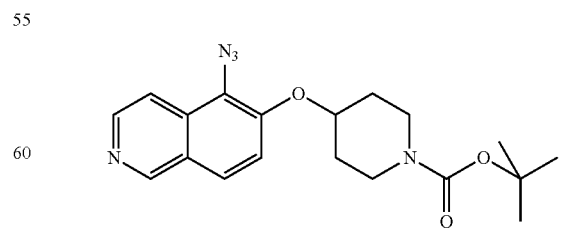

Under argon atmosphere 40 μL (0.04 mmol) of 1N NaOH, 4.6 mg (0.04 mmol) of L-proline, 3.8 mg of (0.02 mmol) CuI and 15.6 mg (0.24 mmol) of NaN₃ were added to a solution of 91 mg (0.2 mmol) of 4-(5-iodo-isoquinoline-6-yloxy)-piperidin-1-carboxylic acid tert-butyl ester (12) in 2 mL of DMSO. The mixture was heated to 60° C. for 18 h. NaN₃, NaOH and L-proline were added in the same amounts again and the reaction was heated to 60° C. for 5 h. After cooling to room temperature water was added. The precipitate was filtered, washed with water and dried in vacuo to give 74 mg of compound 17, which was used without any additional purification.

MS: m/z=370 (MH⁺).

4-(5-Amino-isoquinoline-6-yloxy)-piperidin-1-carboxylic acid tert-butyl ester (18)

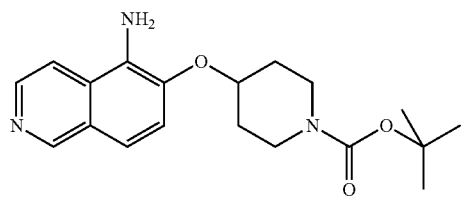 [SMILES: CC(C)(C)OC(=O)N1CCC(Oc2ccc3cnccc3c2N)CC1]

Under argon atmosphere 600 μL (0.6 mmol) of 1N NaOH, 13.8 mg (0.12 mmol) L-proline, 7.6 mg (0.04 mmol) of CuI and 52 mg (0.8 mmol) of NaN₃ were added to a solution of 163 mg (0.4 mmol) 4-(5-bromo-isoquinoline-6-yloxy)-piperidin-1-carboxylic acid tert-butyl ester (11) in 0.6 mL of water. The mixture was heated to 95° C. for 3 h in a microwave reactor (CEM Discovery). After cooling to room temperature water and ethyl acetate were added. The mixture was filtered through Celite, washed with ethyl acetate and concentrated. The crude product was purified by preparative HPLC to yield 42 mg of compound 18 (containing some 11 as impurity).

LCMS Method #4, retention time 0.97 min, detected mass 344.5 [M+H]⁺

4-(7-Vinyl-isoquinolin-6-yloxy)-piperidine-1-carboxylic acid tert-butyl ester (19)

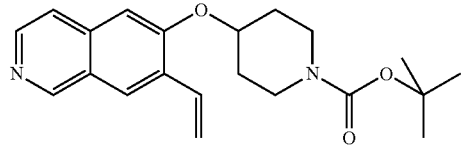 [SMILES: C=Cc1cc2cnccc2cc1OC1CCN(C(=O)OC(C)(C)C)CC1]

Under argon atmosphere 340 mg tributyl-vinyl-stannane (1.07 mmol, 1.2 eq.) and 103 mg of Pd(PPh₃)₄ (0.1 eq.) were added to a solution of 364 mg of 4-(7-Bromo-isoquinoline-6-yloxy)-piperidin-1-carboxylic acid tert-butyl ester (13) (0.98 mmol) in 4 ml of toluene. The reaction was heated to 100° C. in a microwave reactor (CEM Discovery) for 1 h.

After cooling to room temperature water and ethyl acetated were added. The mixture was filtered through a Celite cartridge, washed with ethyl acetate and concentrated. The crude product was purified by preparative HPLC to yield 256 mg (81%) of compound 19.

LCMS Method #4, retention time 1.19 min, detected mass 355.5 [M+H]⁺

The following building blocks were synthesized according to this method:

4-(5-Vinyl-isoquinolin-6-yloxy)-piperidine-1-carboxylic acid tert-butyl ester (19A)

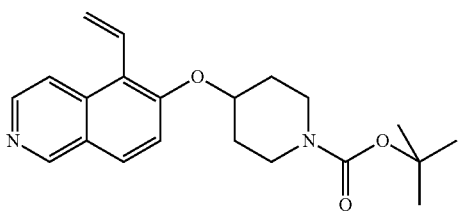 [SMILES: C=Cc1c(OC2CCN(C(=O)OC(C)(C)C)CC2)ccc2cnccc12]

using compound 11 as starting material
LCMS Method #4, retention time 1.11 min, detected mass 355.4 [M+H]⁺

4-(7-Thiophen-2-yl-isoquinolin-6-yloxy)-piperidine-1-carboxylic acid tert-butyl ester (20)

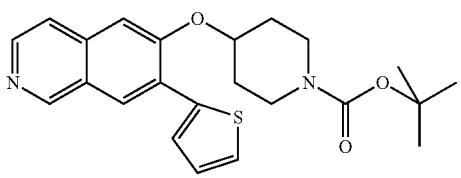 [SMILES: CC(C)(C)OC(=O)N1CCC(Oc2cc3ccncc3cc2-c2cccs2)CC1]

using compound 13 and tributyl-thiophen-2-yl-stannane as starting materials.
LCMS Method #4, retention time 1.26 min, detected mass 411.5 [M+H]⁺

(2,2-Dimethoxy-ethyl)-(4-fluoro-benzyl)-amine (21)

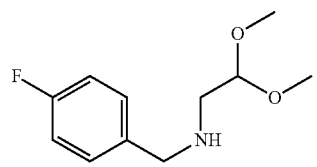

12.4 g of 4-Fluorobenzaldehyde were dissolved in 100 mL of toluene and reacted with 10.5 g 2-Aminoacetaldehyde dimethylacetal and 1.90 g (10 mmol) p-toluenesulfonic acid monohydrate for two hours at a Dean Stark apparatus. The solution was allowed to cool down, extracted with saturated sodium bicarbonate, water and brine, dried over magnesium sulfate and evaporated to dryness. The crude product was dissolved in 100 mL of ethanol. 1.89 g of sodium borohydride were added portionwise. Stirring was continued overnight. For workup, acetic acid was added until no gas evolution could be observed. Then the solution was evaporated to dryness, taken up in dichloromethane and washed twice with water. The organic layer was extracted with brine, dried over magnesium sulfate and evaporated to dryness. The obtained crude product (20 g) was used for further reactions without purification. R_f=0.86 min (Method #1). Detected mass: 182.1 (M-OMe⁻), 214.2 (M+H⁺).

N-(2,2-Dimethoxy-ethyl)-N-(4-fluoro-benzyl)-4-methyl-benzenesulfonamide (22)

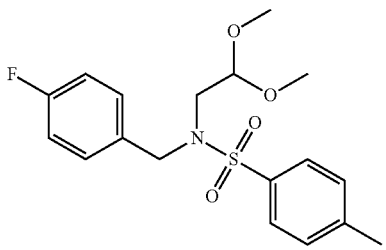 [SMILES: COC(CN(Cc1ccc(F)cc1)S(=O)(=O)c1ccc(C)cc1)OC]

20 g (2,2-Dimethoxy-ethyl)-(4-fluoro-benzyl)-amine (21) were dissolved in 120 ml of dichloromethane. 20 mL of pyridine are added. At 0° C. a solution of 23.8 g p-toluenesulfonic acid chloride in dichloromethane was added dropwise. The reaction was allowed to warm to room temperature and stirring is continued until conversion was completed. For workup, the reaction mixture was extracted twice with 2M hydrochloric acid, twice with sodium bicarbonate and once with brine. The organic layer was dried over magnesium sulfate, evaporated to dryness and the obtained crude product was purified by silica gel chromatography to yield 22.95 g of compound 22 as an orange oil. $R_f$=1.71 min (Method #4). Detected mass: 336.1 (M-OMe$^-$).

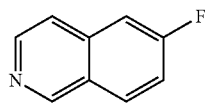 [SMILES: Fc1ccc2cnccc2c1]

6-Fluoro-isoquinoline (23)

41.6 g of AlCl$_3$ were suspended in 400 mL of dichloromethane. At room temperature, a solution of 22.95 g of N-(2,2-Dimethoxy-ethyl)-N-(4-fluoro-benzyl)-4-methyl-benzenesulfonamide (22) in 150 ml of dichloromethane was added. Stirring was continued at room temperature overnight, the solution was poured on ice, the organic layer was separated, the aqueous phase was extracted twice with dichloromethane and the combined organic layers are then extracted twice with sodium bicarbonate. The organic layer was dried over magnesium sulfate, evaporated to dryness and the obtained crude product (8.75 g) is purified by silica gel chromatography to yield 2.74 g of compound 23. $R_f$=0.30 min (Method #4). Detected mass: 148.1 (M+H$^+$).

4-Chloro-6-fluoro-isoquinoline (24)

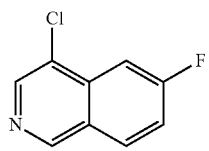 [SMILES: Fc1ccc2cncc(Cl)c2c1]

A solution of 1.5 g 6-fluoro-isoquinoline (23) in 4.5 ml sulfuryl chloride was heated to 60° C. in a microwave reactor (CEM Discovery) for 8 h. After cooling to room temperature the mixture was poured on ice and extracted three times with CHCl$_3$. After drying over Na$_2$SO$_4$ the solvent was distilled off and the crude product was purified by flash chromatography to yield 930 mg of compound 24.

LCMS Method #1, retention time 1.37 min, detected mass 182.01 [M+H]$^+$

Cis and trans N-Boc-2-methyl-piperidin-4-ol (25 and 26)

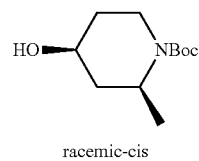

racemic-cis

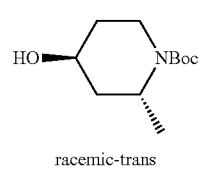

racemic-trans 213 mg (5.6 mmol) of NaBH$_4$ were added portionwise at 0° C. to a solution of 1.0 g (4.7 mmol) 1-Boc-2-methyl-piperidin-4-on in 10 mL EtOH. The mixture was stirred at room temperature for another 2 h. The solvent was removed by distillation and the remainder was dissolved in water and ethyl acetate. The aqueous layer was extracted twice with ethyl acetated and the combined organic layers were dried over Na$_2$SO$_4$. After filtration the solvent was removed by distillation and the crude product was purified by column chromatography n-heptane/ethyl acetate (1/1) to yield 367 mg (36%) of the cis-isomer 25 and 205 mg (20%) of the trans-isomer 26 in addition to 97 mg (10%) mixture of both isomers.

Cis-Isomer (25):
$^1$H-NMR (CDCl$_3$): δ=4.28 (1H, m), 4.17 (1H, m), 3.82 (1H, m), 3.26 (1H, m), 1.85 (1H, ddd, J=14.7, 6.6, und 3.4 Hz), 1.77 (1H, m), 1.66 (2H, m), 1.33 (3H, d, J=7.1 Hz).

Trans-Isomer (26):
$^1$H-NMR (CDCl$_3$): δ=4.50 (1H, m), 4.04 (1H, m), 3.95 (1H, m), 2.87 (1H, dt, J=2.9 und 13.6 Hz), 1.93 (1H, m), 1.83 (1H, m), 1.53 (1H, m), 1.32 (1H, m), 1.14 (3H, d, J=7.1 Hz).

Phenyl-[6-(piperidin-4-yloxy)-isoquinolin-5-yl]-amine (27)

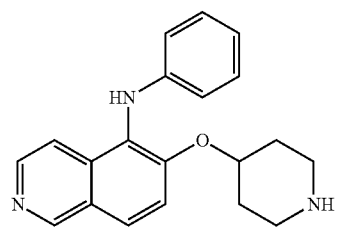 [SMILES: c1ccc(Nc2c(OC3CCNCC3)ccc3cnccc23)cc1]

Under an argon atmosphere 81 mg (0.2 mmol) of 4-(5-bromo-isoquinolin-6-yloxy)-piperidine-1-carboxylic acid tert-butyl ester (11) and 24 mg (0.26 mmol) of aniline were added to a solution of 27 mg (0.28 mmol) of NaOtBu in 3 mL of toluene. After stirring at room temperature for 10 min., 9 mg (0.05 eq) of Pd$_2$dba$_3$ were added and the mixture was heated to 100° C. in a microwave reactor (CEM Discovery) for 1 h. After cooling to room temperature water and ethyl acetate were added. The organic layer was separated, dried over Na$_2$SO$_4$ and concentrated. HPLC purification gave the Boc protected intermediate which was treated with 2 mL 5-6 N HCl in isopropanol for 2 h. The hydrochloride was filtered and subjected to another HPLC chromatography to yield compound 27 as trifluoroacetate (31.3 mg).

LCMS Method #2, retention time 0.78 min, detected mass 320.26 [M+H]$^+$

5-Methyl-6-(piperidin-4-yloxy)-isoquinoline hydrochloride (28)

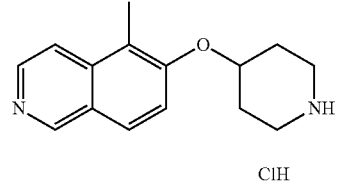 [SMILES: Cc1c(OC2CCNCC2)ccc2cnccc12 ; Cl]

Under an argon atmosphere a 2 M solution of dimethyl zinc (0.5 mL, 93.7 mg, 4 eq.) in toluene was added to a solution of 100 mg (0.24 mmol) 4-(5-bromo-isoquinoline-6-yloxy)-piperidin-1-carboxylic acid tert-butyl ester (11) and 10 mg (1,1'-bis(diphenylphosphino)ferrocen)palladium(II)chloride (0.056 eq. Pd(dppf)Cl$_2$) in 3 mL of dioxane. The mixture was heated to 100° C. for 5 h. After cooling the solvents were distilled off and the remainder was subjected to preparative HPLC to give the Boc-protected intermediate which was treated with 5-6 N HCl in isopropanol for 2 h at room temperature. Removal of the solvents gave 13.7 mg (18%) of compound 28.

LCMS Method #1, retention time 0.67 min, detected mass 243.24 [M+H]$^+$

5-Benzyl-6-(piperidin-4-yloxy)-isoquinoline (29)

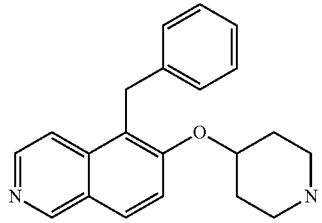 [SMILES: c1ccc(Cc2c(OC3CCNCC3)ccc3cnccc23)cc1]

0.3 mL of water were added to a solution of 81 mg (0.2 mmol) of 4-(5-bromo-isoquinoline-6-yloxy)-piperidin-1-carboxylic acid tert-butyl ester (11), 195 mg (0.6 mmol) of Cs$_2$CO$_3$, 14.6 mg (0.02 mmol) of Pd(dppf)Cl$_2$ and 51 mg (0.26 mmol) of potassium benzyltrifluoroborate in 3 mL of THF. Argon was bubbled through the mixture for 10 minutes and then the reaction was heated to reflux for 16 h (incomplete conversion). After cooling to room temperature water and ethyl acetate were added. The organic layer was separated, dried over Na$_2$SO$_4$. After removal of the solvents 2 mL 5-6 N HCl in isopropanol was added. After 2 h the solvents were distilled off and the remainder was subjected twice to preparative HPLC to give 3.5 mg compound 29 as trifluoroacetate.

LCMS Method #3, retention time 0.56 min, detected mass 319.23 [M+H]$^+$ 6-(Piperidin-4-yloxy)-isoquinoline-5-carboxylic acid ethyl ester (30)

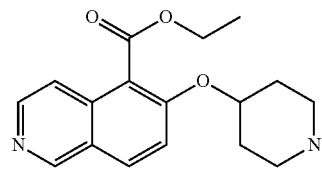 [SMILES: CCOC(=O)c1c(OC2CCNCC2)ccc2cnccc12]

A solution of 200 mg (0.44 mmol) 4-(5-iodo-isoquinoline-6-yloxy)-piperidin-1-carboxylic acid tert-butyl ester (12), 107 mg (0.88 mmol) of DMAP, 4.7 mg (0.1 eq) of Pd on charcoal (10%), 150 µL (0.88 mmol) of triethyl amine and 58 mg (0.22 mmol) of Mo(CO)$_6$ in 3 mL of ethanol was heated to 135° C. for 1 h in a microwave reactor (CEM Discovery). Then water and ethyl acetate were added and the mixture was filtered through a Celite cartridge. After removal of the solvents the remainder was subjected to preparative HPLC to give the 7.4 mg Boc-protected intermediate. To remove the Boc group the intermediate was treated with 2 mL 5-6 N HCl in isopropanol at room temperature for 2 h. Purification by preparative HPLC gave 2.5 mg of compound 30 as TFA salt.

LCMS Method #3, retention time 0.14 min, detected mass 301.29 [M+H]$^+$ 6-(Piperidin-4-yloxy)-isoquinolin-5-ylamine (31)

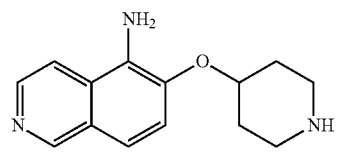 [SMILES: Nc1c(OC2CCNCC2)ccc2cnccc12]

60 µL of 1N NaOH-solution, 6.9 mg (0.3 eq) of L-proline, 3.8 mg (0.1 eq) of CuI and 26 mg (0.4 mmol) of NaN$_3$ were added to a solution of 82 mg (0.2 mmol) of 4-(5-Bromo-isoquinolin-6-yloxy)-piperidine-1-carboxylic acid tert-butyl ester (11) in 2 mL of ethanol/water (7/3). The mixture was heated to 95° C. for 3 h in a microwave reactor (CEM Discover). After cooling water and ethyl acetate were added and the mixture was filtered through a celite cartridge. After removal of the solvents by distillation the remainder was subjected to preparative HPLC. The N-Boc-protected intermediate was deprotected by treatment with 2 mL 5-6 N HCl in isopropanol for 2 h at room temperature. Then water was added and all solvents were removed by freeze drying to yield 18 mg of compound 31 as hydrochloride.

$^1$H-NMR (d$_6$-DMSO): δ=9.60 (1H, s), 8.95 (2H, br s), 8.56 (1H, d, J=7.1 Hz), 8.41 (1H, d, J=7.1 Hz), 7.85 (1H, d, J=9.0 Hz), 7.81 (1H, d, J=9.0 Hz), 5.03 (1H, m), 3.13 (1H, m), 2.92 (1H, m), 2.15 (2H, m), 1.99 (2H, m), 1.84 (1H, m), 1.55 (1H, m).

LCMS Method #1, retention time 0.35 min, detected mass 244.25 [M+H]+

6-(Piperidin-4-yloxy)-5-(1H-tetrazol-5-yl)-isoquinoline (32)

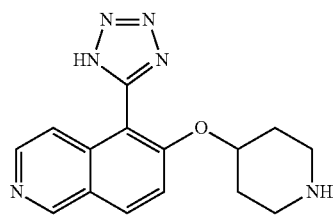 [SMILES: c1cc2c(-c3nnn[nH]3)c(OC3CCNCC3)ccc2cn1]

Under argon atmosphere 78 mg (1.2 mmol) of NaN$_3$ and 64 mg (1.2 mmol) of NH$_4$Cl were added to a solution of 35 mg (0.1 mmol) 4-(5-Cyano-isoquinolin-6-yloxy)-piperidine-1-carboxylic acid tert-butyl ester (15) in 1 mL of DMF. The mixture was heated to approximately 160° C. and 7 bar pressure for 3 h in a microwave reactor (CEM Discovery). After cooling to room temperature aqueous NH$_4$Cl-solution and dichloromethane was added. The mixture was filtered through a phase separation cartridge and the aqueous layer was washed twice with dichloromethane. The organic layers were combined and the solvents were distilled off. The remainder was subjected to preparative HPLC to yield 4 mg (8%) of compound 32 as trifluoroacetate. LCMS Method #3, retention time 0.90 min, detected mass 297.04 [M+H]+

5-(4-Methoxymethyl-[1,2,3]triazol-1-yl)-6-(piperidin-4-yloxy)-isoquinoline (33)

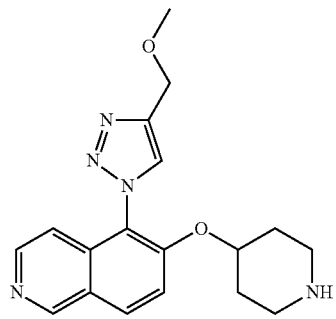 [SMILES: COCc1cn(-c2c(OC3CCNCC3)ccc3cnccc23)nn1]

4 mg (0.1 eq.) of sodium ascorbate and 0.5 mg (0.01 eq.) of Copper(II)sulfate-hydrate were added to a solution of 73 mg (0.2 mmol) of 4-(5-Azido-isoquinoline-6-yloxy)-piperidin-1-carboxylic acid tert-butyl ester (17) and 14 mg (0.2 mmol) of methyl propargyl ether in 4 ml of water/tert-butanol (1/1). The mixture was stirred for 18 h at room temperature. Then ethyl acetate was added and the mixture was filtered through a Celite cartridge. After removal of the solvents the remainder was subjected to preparative HPLC. The N-Boc-protected intermediate was deprotected by treatment with 2 mL 5-6 N HCl in isopropanol for 2 h at room temperature. Then the solvent was evaporated and the product was isolated by preparative HPLC to yield 2.8 mg compound 33 as trifluoroacetate.

LCMS Method #3, retention time 0.08 min, detected mass 340.17 [M+H]+

5-(4-Phenyl-[1,2,3]triazol-1-yl)-6-(piperidin-4-yloxy)-isoquinoline (34)

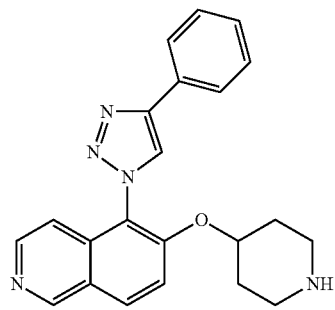 [SMILES: c1ccc(-c2cn(-c3c(OC4CCNCC4)ccc4cnccc34)nn2)cc1]

According to the procedure described for compound 33 the title compound was obtained using 20 mg (0.2 mmol) phenylacetylene. Yield 2.5 mg of compound 34 as trifluoroacetate.

LCMS Method #3, retention time 0.14 min, detected mass 372.2 [M+H]+

7-Ethyl-6-(piperidin-4-yloxy)-isoquinoline hydrochloride (35)

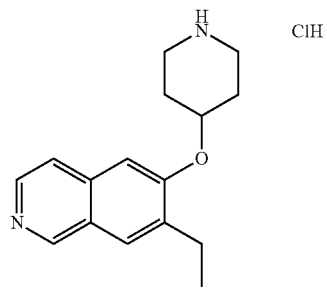 [SMILES: CCc1cc2cnccc2cc1OC1CCNCC1 ; Cl]

1 mg of 5% Palladium on charcoal (0.02 eq.) was added to a solution of 174 mg 4-(7-Vinyl-isoquinolin-6-yloxy)-piperidine-1-carboxylic acid tert-butyl ester (19) (0.49 mmol, 1 eq.) in 15 mL of methanol. The olefin was hydrogenated under 5 bar H$_2$ at ambient temperature over night. Only partial conversion was observed, thus the catalyst was removed by filtration and fresh catalyst was added. Another treatment under the same hydrogenation conditions completed the reaction. Then the catalyst was removed by filtration and the crude product was purified by preparative HPLC to give 97 mg of the Boc protected intermediate.

The protecting group was removed by treatment with 5-6 N HCl in isopropanol for 2 h at room temperature. The solvent was distilled of and water and acetonitrile were added. Freeze drying of the mixture gave 53 mg of compound 35.

LCMS Method #1, retention time 0.71 min, detected mass 257.18 [M+H]+

The following example compound was synthesized according to this method:

5-Ethyl-6-(piperidin-4-yloxy)-isoquinoline trifluoroacetate (36)

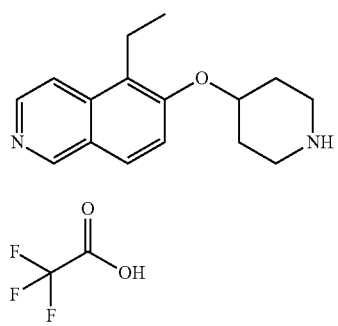

using compound 19A as the starting material

LCMS Method #2, retention time 0.17 min, detected mass 257.21 [M+H]+

Phenyl-[6-(piperidin-4-yloxy)-isoquinolin-5-yl]-methanol hydrochloride (37)

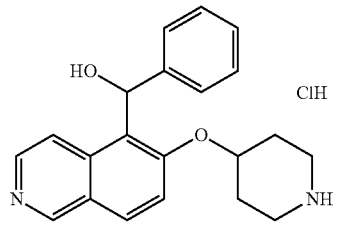 [SMILES: OC(c1ccccc1)c1c(OC2CCNCC2)ccc2cnccc12 ; Cl]

At −78° C. 0.6 mL (0.98 mmol, 1.6 M in hexane) n-butyl lithium were added to a solution of 200 mg (0.49 mmol, 1 eq.) 4-(5-Bromo-isoquinolin-6-yloxy)-piperidine-1-carboxylic acid tert-butyl ester (11) in 3 mL of THF. After 30 min 110 µL (115 mg, 1.08 mmol) of benzaldehyde were added and the mixture was allowed to warm to ambient temperature. After 2 h of stirring at room temperature water and ethyl acetate were added. The layers were separated and the organic layer was washed with water and brine. After drying over Na$_2$SO$_4$ and evaporation of the solvent the remainder was subjected to preparative HPLC to yield the Boc protected intermediate.

The Boc group was removed by dissolving the intermediate in isopropanol and addition of 5-6 N HCl in isopropanol. The precipitated hydrochloride was isolated by filtration to yield 5.2 mg of compound 37 (3%).

$^1$H-NMR (d$_6$-DMSO): δ=9.43 (1H, s), 8.50 (1H, br s), 8.40 (1H, br s), 8.30 (3H, m), 7.87 (1H, d, J=9.2 Hz), 7.33 (2H, d, J=7.4 Hz), 7.28 (2H, t, J=7.4 Hz), 7.19 (1H, t, J=7.4 Hz), 6.74 (1H, s), 6.34 (1H, s), 5.10 (1H, m), 3.25 (2H, m), 3.15 (2H, m), 2.19 (2H, m), 1.93 (2H, m).

LCMS Method #1, retention time 0.80 min, detected mass 335.22 [M+H]+

The following example compound was also synthesized according to this method:

1-[6-(Piperidin-4-yloxy)-isoquinolin-5-yl]-ethanol hydrochloride (38)

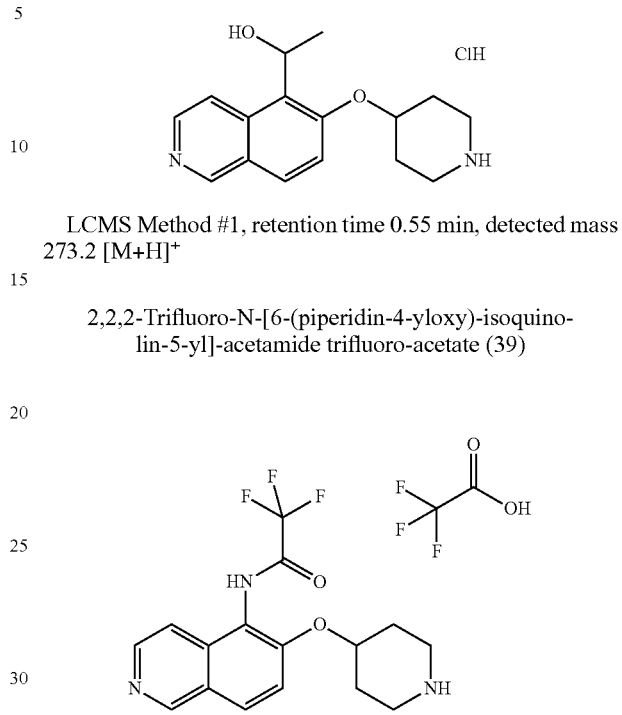

LCMS Method #1, retention time 0.55 min, detected mass 273.2 [M+H]+

2,2,2-Trifluoro-N-[6-(piperidin-4-yloxy)-isoquinolin-5-yl]-acetamide trifluoro-acetate (39)

62.8 mg of potassium carbonate (0.46 mmol, 4 eq.) and 10.7 µL of methanesulfonyl chloride (0.13 mmol, 1.2 eq.) were added to a solution of 39 mg (0.11 mmol) of 4-(5-Amino-isoquinoline-6-yloxy)-piperidin-1-carboxylic acid tert-butyl ester (18) (containing some compound 11) in 3 mL DMF. The reaction was stirred for 4 h at room temperature. Then water and ethyl acetate were added. The mixture was filtered through Celite, washed with ethyl acetate and concentrated to yield a single product. The N-Boc-protected intermediate was deprotected by treatment with 2 mL 5-6 N HCl in isopropanol for 2 h at room temperature. Then the solvent was evaporated and the product was isolated by preparative HPLC to yield 18.5 mg of compound 39.

LCMS Method #1, retention time 0.39 min, detected mass 340.15 [M+H]+

N-[6-(Piperidin-4-yloxy)-isoquinolin-5-yl]-acetamide trifluoro-acetate (40)

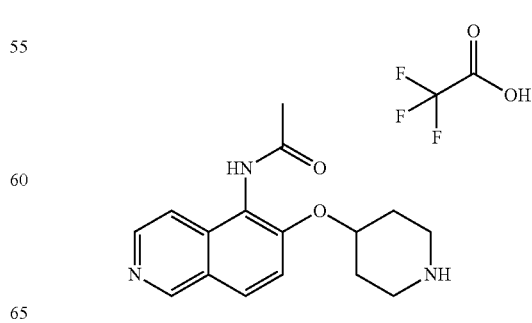

Under argon atmosphere 81.5 mg (0.2 mmol) of 4-(5-bromo-isoquinoline-6-yloxy)-piperidin-1-carboxylic acid tert-butyl ester (11) and 14.2 mg of acetamide (0.24 mmol, 1.2 eq.) were added to a solution of 27 mg (0.28 mmol, 1.4 eq) of NaOtBu in 3 mL toluene. After stirring for 10 minutes at room temperature 9.1 mg (0.01 mmol, 0.05 eq) $Pd_2(dba)_3$ and 11.9 mg (0.04 mmol, 0.2 eq) of 2-(dt-butylphosphino)biphenyl were added. The reaction was heated to 120° C. for 2 h in a microwave reactor (CEM Discovery). Then water and ethyl acetate were added. The mixture was filtered through Celite, washed with ethyl acetate and concentrated. The remainder was subjected twice to preparative HPLC to yield the N-Boc-protected intermediate. The N-Boc-protected intermediate was deprotected by treatment with 2 mL 5-6 N HCl in isopropanol for 2 h at room temperature. Then the solvent was evaporated and the product was isolated by preparative HPLC to yield 2.5 mg of compound 40.

LCMS Method #3, retention time 0.15 min, detected mass 286.15 [M+H]$^+$

General procedure for Boc-deprotection of building blocks:

The corresponding N-Boc-protected compounds were treated with 5-6 N HCl in isopropanol for 2 h at room temperature. The precipitated hydrochlorides were isolated by filtration and dried. If necessary, additional purification by preparative HPLC was performed.

| No. | Compound | Starting material # | LCMS Method # | Retention time | Detected mass [M + H]$^+$ |
|---|---|---|---|---|---|
| 41 | (5-bromoisoquinolin-6-yl)oxy-piperidine · HCl | 11 | 2 | 0.57 | 307.13 |
| 42 | (5-vinylisoquinolin-6-yl)oxy-piperidine · trifluoroacetic acid | 19A | 2 | 0.64 | 255.19 |
| 43 | (5-cyanoisoquinolin-6-yl)oxy-piperidine · HCl | 15 | 2 | 0.46 | 254.15 |
| 44 | (5-iodoisoquinolin-6-yl)oxy-piperidine · HCl | 12 | 1 | 0.67 | 355.04 |
| 45 | (7-cyanoisoquinolin-6-yl)oxy-piperidine · HCl | 16 | 1 | 0.64 | 254.13 |

| No. | Compound | | Starting material # | LCMS Method # | Retention time | Detected mass [M + H]+ |
|---|---|---|---|---|---|---|
| 46 | 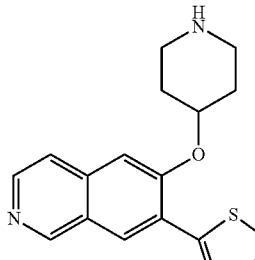 | HCl | 20 | 1 | 0.87 | 311.12 |
| 47 | 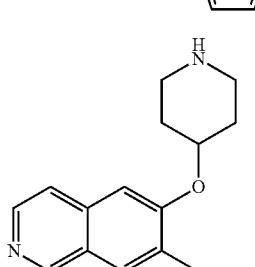 | HCl | 19 | 1 | 0.72 | 255.19 |
| 48 | 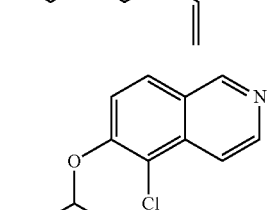 | | 8 | 1 | 0.52 | 263.10 |

General procedure for Suzuki-coupling with 4-(5-Bromo-isoquinoline-6-yloxy)-piperidin-1-carboxylic acid tert-butyl ester (11)

Aqueous Na₂CO₃ solution (0.2 ml, 0.4 mmol, 2 eq. 2M) was added to a solution of 81 mg (0.2 mmol, 1 eq.) of 4-(5-Bromo-isoquinoline-6-yloxy)-piperidin-1-carboxylic acid tert-butyl ester (11) and 1.5 eq. (0.3 mmol) of the corresponding boronic acid (reagent 2) in 3 mL of DME. Argon was bubbled through the reaction mixture for 10 min. Then 23 mg (0.1 eq.) Pd(PPh₃)₄ were added and the reaction was stirred at 95° C. overnight under Argon atmosphere. After cooling 2 mL of water and 10 mL of ethyl acetate were added. The organic layer was separated, dried and the solvent was distilled off. The remainder was subjected to preparative HPLC.

The Boc group was removed by dissolving the intermediate in isopropanol and addition of 5-6 N HCl in isopropanol. The precipitate was isolated by filtration.

In some reactions no hydrochloride precipitated or the purity of the precipitate was unsatisfactory. In these cases the solvent was distilled off and the remainder was purified by preparative HPLC.

The following examples were synthesized using this method:

| No. | Compound | Reagent 1 | Reagent 2 | Method # | retention time | detected mass [M + H]+ |
|---|---|---|---|---|---|---|
| 49 | 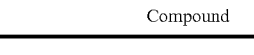 | 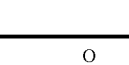 11 | 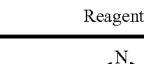 | 2 | 0.15 | 306.22 |

-continued

| No. | Compound | Reagent 1 | Reagent 2 | Method # | retention time | detected mass [M + H]+ |
|---|---|---|---|---|---|---|
| 50 | | 11 TFA | | 4 | 0.75 | 335.20 |
| 51 | | 11 HCl | | 4 | 0.76 | 305.15 |
| 52 | | 11 TFA | | 1 | 0.81 | 347.18 |
| 53 | | 11 HCl | | 1 | 0.84 | 347.17 |
| 54 | | 11 HCl | | 1 | 0.90 | 349.24 |

| No. | Compound | Reagent 1 | Reagent 2 | Method # | retention time | detected mass [M + H]+ |
|---|---|---|---|---|---|---|
| 55 | (acetamidophenyl isoquinoline piperidinyloxy) · HCl | 11 | 3-acetamidophenylboronic acid | 1 | 0.75 | 362.22 |
| 56 | (4-fluorophenyl isoquinoline piperidinyloxy) · HCl | 11 | 4-fluorophenylboronic acid | 1 | 0.88 | 323.20 |
| 57 | (4-cyanophenyl isoquinoline piperidinyloxy) · TFA | 11 | 4-cyanophenylboronic acid | 3 | 0.44 | 371.24 [M + MeCN + H]+ |
| 58 | (4-trifluoromethoxyphenyl isoquinoline piperidinyloxy) · TFA | 11 | 4-trifluoromethoxyphenylboronic acid | 3 | 1.09 | 389.13 |

-continued

| No. | Compound | Reagent 1 | Reagent 2 | Method # | retention time | detected mass [M + H]+ |
|---|---|---|---|---|---|---|
| 59 | | 11 TFA | benzofuran-2-boronic acid | 3 | 1.02 | 345.14 |
| 60 | | 11 TFA | 3,4-dichlorophenylboronic acid | 3 | 1.06 | 373.03 |
| 61 | | 11 TFA | 4-nitrophenylboronic acid | 1 | 0.87 | 350.16 |
| 62 | | 11 HCl | 4-(methylsulfonyl)phenylboronic acid | 1 | 0.72 | 383.14 |

-continued

| No. | Compound | Reagent 1 | Reagent 2 | Method # | retention time | detected mass [M + H]+ |
|---|---|---|---|---|---|---|
| 62A | (isoquinoline with O-piperidine and 2-methylpropenyl substituent) · TFA | 11 | 2-methylpropenyl boronic acid | 1 | 0.79 | 283.18 |
| 63 | (isoquinoline with O-piperidine and quinolin-5-yl substituent) · TFA | 11 | quinolin-5-yl boronic acid | 2 | 0.18 / 0.47 | 356.21 / 356.23 |
| 64 | (isoquinoline with O-piperidine and 4-cyclohexylphenyl substituent) · TFA | 11 | 4-cyclohexylphenyl boronic acid | 2 | 1.31 | 387.30 |
| 65 | (isoquinoline with O-piperidine and 3-(methylsulfonyl)phenyl substituent) · HCl | 11 | 3-(methylsulfonyl)phenyl boronic acid | 2 | 0.73 | 383.21 |
| 66 | (isoquinoline with O-piperidine and 4-methyl-3-nitrophenyl substituent) · TFA | 11 | 4-methyl-3-nitrophenyl boronic acid | 1 | 0.90 | 364.15 |

-continued

| No. | Compound | Reagent 1 | Reagent 2 | Method # | retention time | detected mass [M + H]+ |
|---|---|---|---|---|---|---|
| 67 | (isoquinoline with phenyl-CH2OH and piperidinyloxy substituents) TFA | 11 | 3-(hydroxymethyl)phenylboronic acid | 1 | 0.76 | 335.17 |
| 68 | (isoquinoline with 3-(N,N-dimethylcarbamoyl)phenyl and piperidinyloxy substituents) TFA | 11 | 3-(N,N-dimethylcarbamoyl)phenylboronic acid | 3 | 0.42 | 376.18 |
| 69 | (isoquinoline with 3-carbamoylphenyl and piperidinyloxy substituents) HCl | 11 | 3-carbamoylphenylboronic acid | 2 | 0.61 | 348.23 |
| 70 | (isoquinoline with 4-(N,N-dimethylamino)phenyl and piperidinyloxy substituents) HCl | 11 | 4-(N,N-dimethylamino)phenylboronic acid | 1 | 0.61 | 348.21 |

-continued

| No. | Compound | Reagent 1 | Reagent 2 | Method # | retention time | detected mass [M + H]+ |
|---|---|---|---|---|---|---|
| 71 | HCl | 11 | | 4 | 0.75 | 398.15 |
| 72 | TFA | 11 | | 2 | 0.64 | 350.24 |
| 73 | TFA | 11 | | 2 | 0.93 | 349.24 |
| 74 | TFA | 11 | | 2 | 1.22 | 399.23 |

| No. | Compound | Reagent 1 | Reagent 2 | Method # | retention time | detected mass [M + H]+ |
|---|---|---|---|---|---|---|
| 75 | (structure) TFA | 11 | (structure) | 2 | 0.75 | 363.23 |
| 76 | (structure) TFA | 11 | (structure) | 2 | 0.87 | 349.25 |
| 77 | (structure) TFA | 11 | (structure) | 2 | 0.81 | 348.20 |
| 78 | (structure) HCl | 11 | (structure) | 2 | 1.00 | 333.25 |

Suzuki Coupling Procedure for Variation in the 5- and 7-Position

The base was added to a solution of reagent 1 (typically 0.2 mmol) and reagent 2 in DME. Argon was bubbled through the reaction mixture for 10 min. Then the catalyst was added and the reaction was stirred at reflux temperature overnight under Argon atmosphere. After cooling 2 mL of water and 10 mL of ethyl acetate were added. The mixture was filtered through a celite cartridge. The solvents were removed by distillation and the remainder was subjected to preparative HPLC.

The isolated intermediate was deprotected by treatment with 2 mL 5-6 N HCl in isopropanol for 2 h at room temperature. The solvent was distilled of and the precipitate was isolated by filtration. In some reactions no hydrochloride precipitated or the purity of the precipitate was unsatisfactory. In these cases the solvent was distilled off and the remainder was purified by preparative HPLC.

Using this method the following examples were prepared:

| No. | Compound | Reagent 1 | Reagent 2 | Catalyst | Base | LCMS Method # | Retention time | Detected mass [M + H]+ |
|---|---|---|---|---|---|---|---|---|
| 79 | | 12 | cyclopropyl-B(OH)₂ | 0.05 eq. PdOAc₂ 0.1 eq. P(Cy)₃ | 3.5 eq. K₃PO₄ | 2 | 0.66 | 269.17 |
| 80 | | 12 | ethyl-B(OH)₂ | 0.05 eq. PdOAc₂ 0.1 eq. P(Cy)₃ | 3.5 eq. K₃PO₄ | 1 | 0.81 | 271.19 |
| 81 | | 13 | phenyl-B(OH)₂ | 0.15 eq. Pd(PPh₃)₄ | 2 eq. K₂CO₃ | 1 | 0.87 | 305.16 |
| 82 | | 13 | cyclopropyl-B(OH)₂ | 0.15 eq. Pd(PPh₃)₄ | 2 eq. K₂CO₃ | 1 | 0.85 | 269.2 |

5-Isopropenyl-6-(piperidin-4-yloxy)-isoquinoline (83)

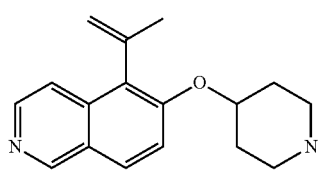 [SMILES: C=C(C)c1c(OC2CCNCC2)ccc2cnccc12]

85 mg (0.62 mmol) of K₂CO₃ and 70 mg (0.15 mmol) of 4-[5-(4,4,5,5-Tetramethyl-[1,3,2]dioxaborolan-2-yl)-iso-quinoline-6-yloxy]-piperidin-1-carboxylic acid tert-butyl ester (14) were added to a solution of 22 mg (0.18 mmol) 2-Bromo-propene in 2 mL of DMF. Under argon atmosphere 5.6 mg (0.05 eq) of Pd(dppf)Cl₂ were added and the mixture was heated to 100° C. for 16 h. After cooling to room temperature water and dichloromethane were added. The mixture was filtered through a Celite cartridge. The solvents were removed by distillation and the remainder was subjected to preparative HPLC. The isolated intermediate was deprotected by treatment with 2 mL 5-6 N HCl in isopropanol for 2 h at room temperature. The solvent was distilled of and compound 83 was isolated by preparative HPLC to give 3.2 mg as the trifluoroacetate.

LCMS Method #3, retention time 0.15 min, detected mass 269.15 [M+H]+

Using this method the following examples were prepared:

| No. | Compound | Reagent | LCMS Method # | retention time | detected mass [M + H]+ |
|---|---|---|---|---|---|
| 84 | | | 3 | 0.14 | 353.16 |
| 85 | | | 3 | 0.41 | 311.22 |
| 86 | | | 3 | 0.56 | 323.15 |

6-Methoxy-4-(4,4,4-trifluoro-butyl)-isoquinoline (87)

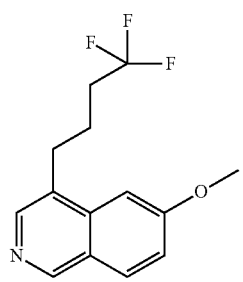 [SMILES: COc1ccc2cncc(CCCC(F)(F)F)c2c1]

2 g 6-Methoxy-isoquinoline were dissolved in 25 mL of dry tetrahydrofuran. 12.56 mL of a 1 M solution of potassium triethyl borohydrate were added dropwise. The solution was allowed to stir at room temperature for 2 h, then 3.29 g of 4,4,4-Trifluoro-1-iodobutane were added dropwise. The solution was allowed to stir overnight, then 32 mL of 1M sodium hydroxide and 12 mL of sodium peroxide solution (35%) were added. Stirring was continued for another 3 hrs, then the solution was diluted with dichloromethane, extracted with water and brine and the organic layer was dried over sodium sulfate and evaporated to dryness. Silica gel chromatography yields 1.03 g of the desired product.

LCMS Method #1, retention time 1.20 min, detected mass 270.06 [M+H]+

6-Hydroxy-4-(4,4,4-trifluoro-butyl)-isoquinoline (88)

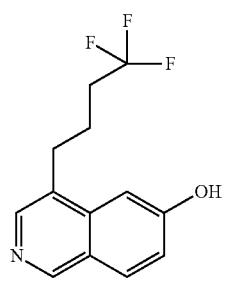 [SMILES: Oc1ccc2cncc(CCCC(F)(F)F)c2c1]

1.02 g of 6-Methoxy-4-(4,4,4-trifluoro-butyl)-isoquinoline (87) were treated with boron tribromide as described for the synthesis of compound 1 to give 410 mg of the desired product 88. LCMS Method #1, retention time 1.04 min, detected mass 256.00 [M+H]+

59

4-[4-(4,4,4-Trifluoro-butyl)-isoquinolin-6-yloxy]-piperidine-1-carboxylic acid tert-butyl ester (89)

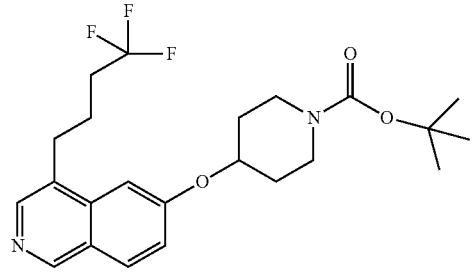 [SMILES: CC(C)(C)OC(=O)N1CCC(Oc2ccc3cncc(CCCC(F)(F)F)c3c2)CC1]

100 mg of compound 88, 118 mg of Boc-(4-hydroxy) piperidine and 416 mg of Diphenyl-[4-[1H,1H,2H,2H-perfluorodecyl]phenyl]phosphine were dissolved in 5 mL of dry tetrahydrofuran. 208 mg of Bis (1H, 2H, 2H, 3H, 3H-perfluorononyl)-azodicarboxylate were added and the reaction was allowed to stir overnight. The mixture was evaporated to dryness and filtered over a 5 g Fluoro-Flash cartridge. The obtained crude product was purified by preparative HPLC to yield 46 mg of the desired product.

LCMS Method #1, retention time 1.51 min, detected mass 439.13 [M+H]$^+$

60

6-(Piperidin-4-yloxy)-4-(4,4,4-trifluoro-butyl)-isoquinoline (90)

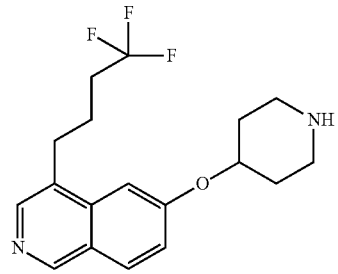 [SMILES: FC(F)(F)CCCc1cncc2ccc(OC3CCNCC3)cc12]

42 mg of compound 89 were dissolved in 5M hydrochloric acid in isopropanol. The solution was stirred at room temperature for 2 hrs and another 2 hrs at 40° C., evaporated to dryness and taken up in water and lyophilized three times to give 32 mg of the desired product as the hydrochloride salt. LCMS Method #1, retention time 0.98 min, detected mass 338.16 [M+H]$^+$ The following isoquinolines were synthesized in a similar fashion as described for compound 90, using appropriate alkyl halides:

| No. | Compound | Weight | Method | RT [min] | Detected Mass [MH$^+$] |
|---|---|---|---|---|---|
| 91 | HCl | 242.14 | 1 | 0.56 | 243.13 |
| 92 | HCl | 318.17 | 1 | 0.84 | 319.17 |

General procedure for reductive amination:

1.5 eq of aldehyde was dissolved in 1 mL of methanol and 50 mg of compound 124 and 27 mg of anhydrous sodium acetate, dissolved in methanol, were added. 0.250 mL of a solution of 1M sodium cyanoborohydride in THF was added. The reaction was allowed to run overnight, then the solution was filtered, evaporated to dryness and the residue was taken up in ethyl acetate. The organic layer was extracted with a solution of 5% sodium carbonate in water, then with 5% sodium chloride in water. The organic layer was dried, evaporated to dryness and purified by RP chromatography.

This procedure was used to obtain compounds 93 to 123:

| No. | Compound | RT | Mass [MH]+ |
|---|---|---|---|
| 93 | | 0.13 | 257.23 |
| 94 | | 0.53 | 271.26 |
| 95 | | 0.79 | 285.27 |
| 96 | | 0.92 | 299.29 |
| 97 | | 0.74 | 285.27 |

| No. | Compound | RT | Mass [MH]+ |
|---|---|---|---|
| 98 | 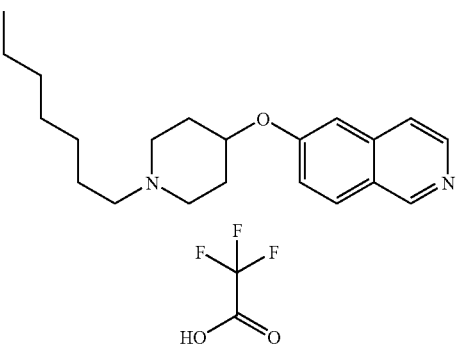 | 1.22 | 327.30 |
| 99 | 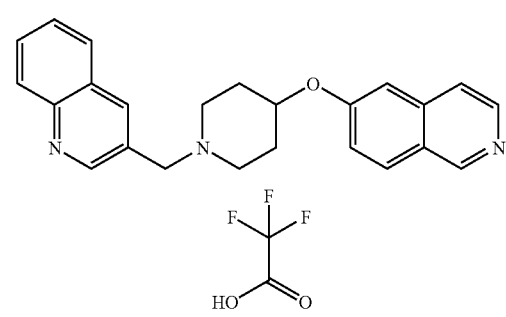 | 0.89 | 370.29 |
| 100 | 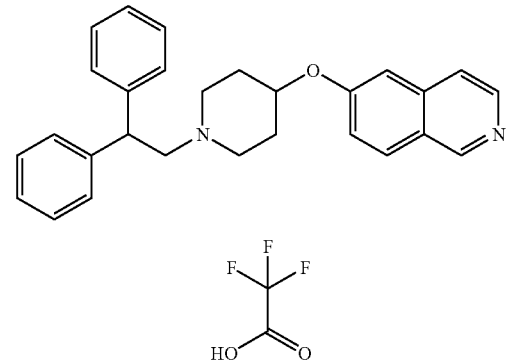 [SMILES: c1ccc(C(CN2CCC(Oc3ccc4cnccc4c3)CC2)c2ccccc2)cc1 ; O=C(O)C(F)(F)F] | 1.25 | 409.34 |
| 101 | 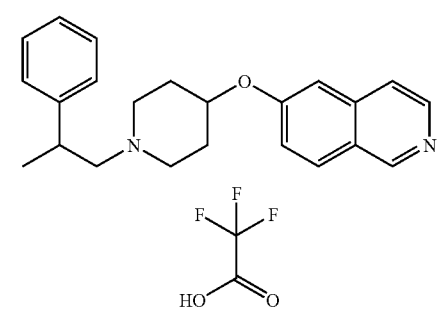 | 1.06 | 347.29 |
| 102 | 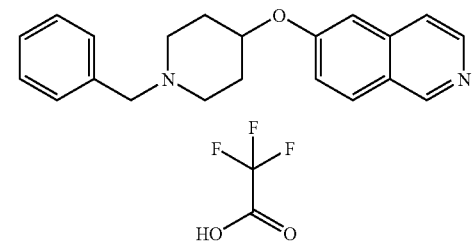 | 0.89 | 319.26 |

-continued

| No. | Compound | RT | Mass [MH]+ |
|---|---|---|---|
| 103 | 4-ethylbenzyl-piperidinyloxy-isoquinoline, TFA salt | 0.99 | 347.32 |
| 104 | 2-ethylbenzyl-piperidinyloxy-isoquinoline, TFA salt | 0.96 | 347.29 |
| 105 | cyclopropylmethyl-piperidinyloxy-isoquinoline, TFA salt | 0.60 | 283.15 |
| 106 | 2-fluorobenzyl-piperidinyloxy-isoquinoline, TFA salt | 0.74 | 337.26 |
| 107 | 3-fluorobenzyl-piperidinyloxy-isoquinoline, TFA salt | 0.95 | 337.24 |

-continued
| No. | Compound | RT | Mass [MH]+ |
|---|---|---|---|
| 108 | 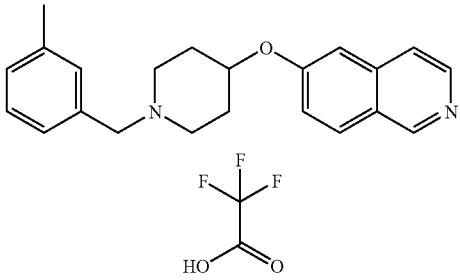 | 1.01 | 333.28 |
| 109 | 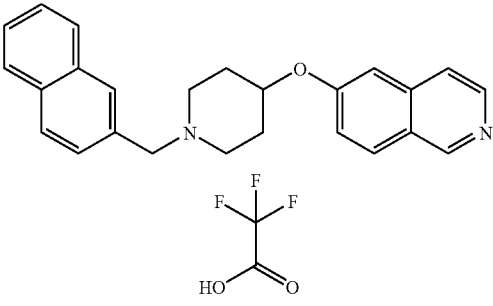 | 1.04 | 369.29 |
| 110 | 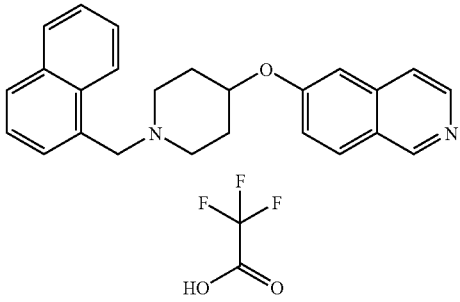 | 1.14 | 369.30 |
| 111 | 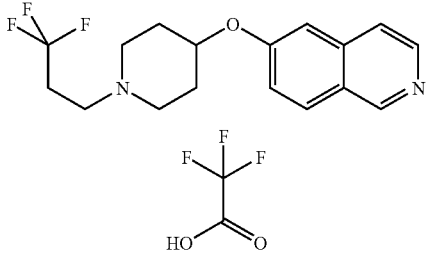 | 0.58/0.74 | 325.23 |
| 112 | 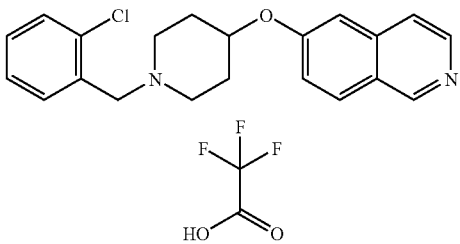 | 1.00 | 353.22/355.23 |

| No. | Compound | RT | Mass [MH]+ |
|---|---|---|---|
| 113 | 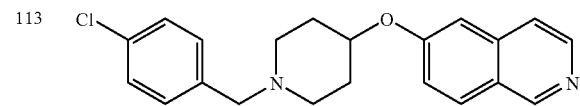 | 0.91 | 353.23/355.23 |
| 114 | 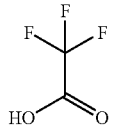 | 0.88 | 353.24/355.24 |
| 115 | 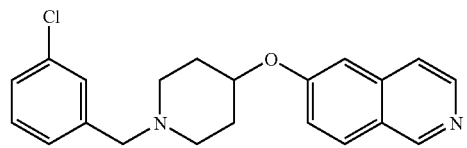 | 0.87 | 364.20 |
| 116 | 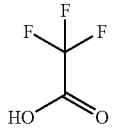 | 0.92 | 364.26 |
| 117 | 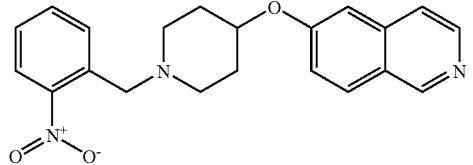 | 1.10 | 347.31 |

-continued

| No. | Compound | RT | Mass [MH]+ |
|---|---|---|---|
| 118 | | 0.77 | 299.28 |
| 119 | | 1.13 | 361.31 |
| 120 | | 1.07 | 399.30 |
| 121 | | 0.86 | 367.27 |
| 122 | | 1.15 | 447.22/449.68 |

-continued

| No. | Compound | RT | Mass [MH]+ |
|---|---|---|---|
| 123 | 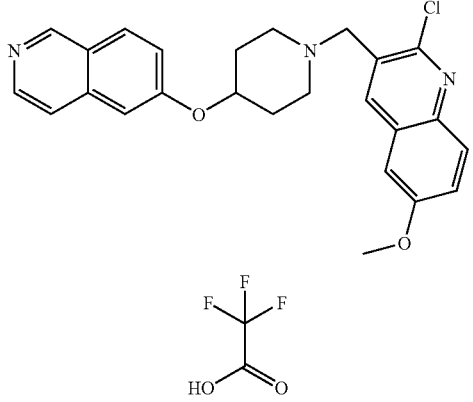 [SMILES: COc1ccc2nc(Cl)c(CN3CCC(Oc4ccc5cnccc5c4)CC3)cc2c1 ; O=C(O)C(F)(F)F] | 1.13 | 434.16 |

All LCMS in this table were obtained using LCMS method #2.

General Procedure for the Reaction of Boc-Protected Aminoalcohols with 6-Hydroxy Isoquinolines (Mitsunobu-Reaction):

AAV1:

To 500 mg (1.5 mmol) of triphenylphosphine (bound to polystyrene, 3 mmol/g) and 10 ml of dichloromethane 0.195 mL (1.2 mmol) of diethylazodicarboxylate (or alternatively diisopropylazodicarboxylate) were added. The reaction mixture was allowed to shake for 10 min. and then 0.14 mL of triethylamine, 145 mg of 6-hydroxyisoquinoline (7) (or an equivalent amount of a different suitable isoquinoline) (reagent 1) and 1 mmol of the desired, boc-protected aminoalcohol (reagent 2) was added. The reaction was shaken at room temperature until no further conversion could be observed by LCMS. For workup, the solution was filtered, the residue was washed with dichloromethane and the organic layer was washed twice with 1N sodium hydroxide, twice with water and once with brine, dried over magnesium sulfate and evaporated. The crude product was purified by preparative HPLC to yield the boc protected coupled product.

General Procedure for Removal of the Boc-Group (AAV2):

The starting material was dissolved in 2M hydrochloric acid and reacted overnight. To compounds with poor aqueous solubility, methanol or dioxane was added until a homogenous solution was obtained. Alternatively, 4M hydrochloric acid in isopropanol was used as the reactive compound. The reaction mixture was lyophilised and the deprotected product is obtained as the corresponding hydrochloride of the free amine.

| No. | Compound | Reagent 1 | Reagent 2 | LCMS Method # | Retention time | Detected mass [M + H]+ |
|---|---|---|---|---|---|---|
| 124 | 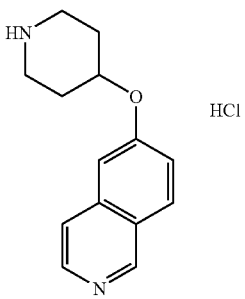 [SMILES: c1cc2cc(OC3CCNCC3)ccc2cn1 ; Cl] | 7 | 4-Hydroxypiperidine-1-carboxylic acid tert-butyl ester | 1 | 0.47 | 229.21 |
| 125 | 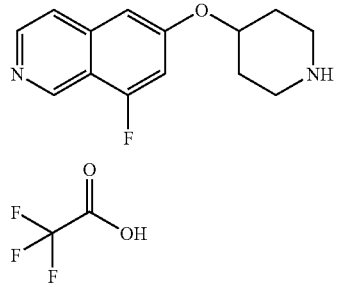 | 2 | 4-Hydroxypiperidine-1-carboxylic acid tert-butyl ester | 4 | 0.37 | 247.4 |

-continued

| No. | Compound | Reagent 1 | Reagent 2 | LCMS Method # | Retention time | Detected mass [M + H]+ |
|---|---|---|---|---|---|---|
| 126 | (structure with TFA) | 2 | 3-Hydroxypiperidine-1-carboxylic acid tert-butyl ester | 4 | 0.34 | 247.35 |
| 127 | (structure) HCl | 2 | 4-Piperidylmethanol-1-carboxylic acid tert-butyl ester | 4 | 0.53 | 261.20 |
| 128 | (structure) HCl | 2 | 3-Piperidylmethanol-1-carboxylic acid tert-butyl ester | 4 | 0.57 | 261.20 |
| 129 | (structure) HCl | 3 | 4-Hydroxypiperidine-1-carboxylic acid tert-butyl ester | 4 | 0.35 | 247.10 |
| 130 | (structure) HCl | 3 | 3-Hydroxypiperidine-1-carboxylic acid tert-butyl ester | 4 | 0.35 | 247.10 |

-continued

| No. | Compound | Reagent 1 | Reagent 2 | LCMS Method # | Retention time | Detected mass [M + H]+ |
|---|---|---|---|---|---|---|
| 131 | | 4 | 4-Hydroxypiperidine-1-carboxylic acid tert-butyl ester | 3 | 0.14 | 243.12 |
| 132 | | 8 | 3-Hydroxypiperidine-1-carboxylic acid tert-butyl ester | 4 | 0.60 | 263.15 |
| 133 | | 6 | 4-Hydroxypiperidine-1-carboxylic acid tert-butyl ester | 4 | 0.67 | 257.15 |
| 134 | | 5 | 4-Hydroxypiperidine-1-carboxylic acid tert-butyl ester | 1 | 0.68 | 257.20 |
| 135 | | 8 | 4-Hydroxypiperidine-1-carboxylic acid tert-butyl ester | 1 | 0.52 | 263.10 |
| 136 | | 9 | 4-Hydroxymethyl-piperidine-1-carboxylic acid tert-butyl ester | 2 | 0.33 | 321.14/323.15 |

-continued

| No. | Compound | Reagent 1 | Reagent 2 | LCMS Method # | Retention time | Detected mass [M + H]+ |
|---|---|---|---|---|---|---|
| 137 | | 9 | 3-Hydroxy-piperidine-1-carboxylic acid tert-butyl ester | 2 | 0.31 | 307.12/309.12 |
| 138 | | 9 | N-Methyl-3-piperidylmethanol | 1 | 0.75 | 335.12 |
| 139 | | 1 | 4-Hydroxypiperidine-1-carboxylic acid tert-butyl ester | 2 | 0.62 | 307.06 |
| 140 | | 7 | 26 | 1 | 0.60 | 243.22 |
| 141 | | 7 | 25 | 1 | 0.60 | 243.19 |
| 142 | | 7 | 25 | 1 | 0.60 | 243.29 |
| 143 | | 7 | 26 | 3 | 0.12 | 243.13 |

-continued

| No. | Compound | Reagent 1 | Reagent 2 | LCMS Method # | Retention time | Detected mass [M + H]+ |
|---|---|---|---|---|---|---|
| 144 | (isoquinoline-6-yloxymethyl-1-benzylpiperidine structure); TFA | 7 | (1-Benzyl-piperidin-4-yl)-methanol | 2 | 0.17 | 333.2 |
| 145 | (isoquinoline-6-yloxy-piperidin-3-yl structure); TFA | 7 | 3-Hydroxy-piperidine-1-carboxylic acid tert-butyl ester | 2 | 0.2 | 229.2 |
| 146 | (isoquinoline-6-yloxyethyl-piperidin-4-yl structure); HCl | 7 | 4-(2-Hydroxy-ethyl)-piperidine-1-carboxylic acid tert-butyl ester | 2 | 0.18 | 257.2 |
| 147 | (isoquinoline-6-yloxy-1-methylpiperidin-4-yl structure); HCl | 7 | 1-Methyl-piperidin-4-ol | 1 | 0.45 | 243.2 |
| 148 | (isoquinoline-6-yloxymethyl-piperidin-3-yl structure); HCl | 7 | 3-Hydroxymethyl-piperidine-1-carboxylic acid tert-butyl ester | 2 | 0.17 | 243.2 |
| 149 | (isoquinoline-6-yloxymethyl-piperidin-4-yl structure); HCl | 7 | 4-Hydroxymethyl-piperidine-1-carboxylic acid tert-butyl ester | 2 | 0.17 | 243.2 |

Chromatographic Resolution of Compounds 140 and 143:

The N-Boc protected intermediate, obtained as an enantiomeric mixture of compound 140 and compound 143, was separated into the enantiomers on a chiral column (Chiralcel OD-H/56 250×4.6 mm). The removal of the protection group as the final step was performed as described in the general procedure.

The absolute configuration of the stereo centers has not been determined.

Compound 140: earlier eluting Boc-protected intermediate;

Compound 143: later eluting Boc-protected intermediate

Chromatographic Resolution of Compounds 141 and 142:

The N-Boc protected intermediate, obtained as an enantiomeric mixture of compound 141 and compound 142, was separated into the enantiomers on a chiral column (Chiralpak AD-H/40 250×4.6 mm). The removal of the protection group as the final step was performed as described in the general procedure.

The absolute configuration of the stereo centers has not been determined.

Compound 141: earlier eluting Boc-protected intermediate;

Compound 142: later eluting Boc-protected intermediate.

7-Chloro-6-fluoro-isoquinoline (150)

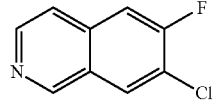 [SMILES: Fc1cc2ccncc2cc1Cl]

7-Chloro-6-fluoro-isoquinoline is obtained by the same reaction sequence, used for the synthesis of 6-Fluoro-isoquinoline (23), starting from 3-Chloro-4-fluoro-benzaldehyde. $R_t$=0.77 min (Method #2). Detected mass: 182.1/184.1 (M+H$^+$).

5-Chloro-6-fluoro-isoquinoline-trifluoro acetate (151)

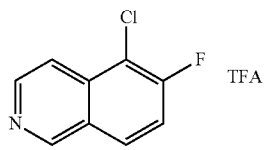 [SMILES: Fc1ccc2cnccc2c1Cl]

7.0 g (38.1 mmol) of 6-Fluoroisoquinoline (23) are dissolved in 60 mL of concentrated sulfuric acid. At 0° C. 10.18 g of N-Chlorosuccinimide are added. After 1 h another 5.2 g of N-Chlorosuccinimide are added and the solution is warmed to 50° C. Two more portions of 5.2 g N-Chlorosuccinimide are added successively and stirring is continued at 50° C. until the reaction is complete. The reaction mixture is cooled to room temperature, is poured on ice and adjusted to pH 10 by addition of sodium hydroxide. The precipitate is filtered off, taken up in dichloromethane and washed with aqueous sodium hydroxide. The organic layer is dried over magnesium sulfate, evaporated and the crude product is purified by preparative HPLC to yield 4.04 g of 5-Chlor-6-fluoro-isoquinoline (151) as trifluoroacetate. $R_t$=0.97 min (Method #2). Detected mass: 182.0/184.0 (M+H$^+$).

6-Fluoro-5-nitro-isoquinoline (152)

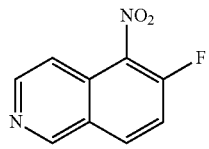 [SMILES: O=[N+]([O-])c1c(F)ccc2cnccc12]

Under cooling 2.0 mL of concentrated nitric acid are added to 2.8 mL of sulphuric acid. Subsequently 350 mg of 6-fluoroisoquinoline (23) are added, the reaction is warmed up to room temperature and allowed to stir overnight. The reaction mixture is poured on ice, extracted with dichloromethane and adjusted to alkaline pH by addition of sodium hydroxide. The aqueous layer is extracted again with dichloromethane. The dichloromethane layer is dried over magnesium sulfate and evaporated to give 90 mg of 6-Fluoro-5-nitro-isoquinoline, which can be used without further purification. $R_t$=1.03 min (Method #1). Detected mass: 193.0 (M+H$^+$).

4-(Isoquinolin-6-yloxy)-piperidine-1-carboxylic acid-tert-butylester (154)

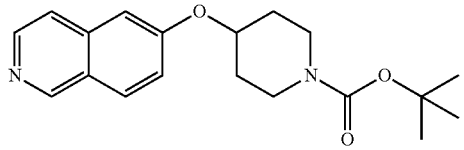 [SMILES: CC(C)(C)OC(=O)N1CCC(Oc2ccc3cnccc3c2)CC1]

7.49 g of 4-Hydroxy-piperidine-1-carboxylic acid-tert-butylester are dissolved in 20 mL of dry dimethyl acetamide. 1.49 g of sodium hydride (60%) are added. Then a solution of 3.65 g 6-Fluoroisoquinoline (23) is added dropwise. The solution is heated at 80° C. for 2 hours, then the solvent is removed and the residue is taken up in dichloromethane. The organic layer is extracted twice with water and then with brine, dried over magnesium sulfate and evaporated to dryness. The crude product is purified by silica gel chromatography to yield 6.22 g of 4-(Isoquinolin-6-yloxy)-piperidine-1-carbocyclic acid-tert-butylester. $R_t$=1.32 min (Method #1). Detected mass: 329.1 (M+H$^+$).

6-(Piperidin-4-yloxy)-isoquinoline hydrochloride (124)

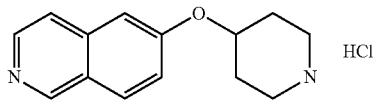 [SMILES: c1cc2cc(OC3CCNCC3)ccc2cn1 ; Cl]

4-(Isoquinolin-6-yloxy)-piperidine-1-carboxylic acid-tert-butylester (154) is deprotected by the general procedure described in AAV2 to yield the title compound as HCl-salt. $R_t$=0.20 min (Method #2). Detected mass: 229.1 (M+H$^+$).

The following example was synthesized according to this method:

4-Chloro-6-(piperidin-4-yloxy)-isoquinoline hydrochloride (156)

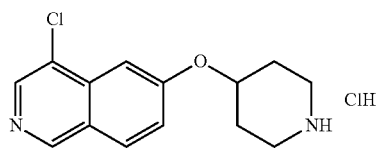 [SMILES: Clc1cncc2ccc(OC3CCNCC3)cc12 ; Cl]

using 4-chloro-6-fluoro-isoquinoline (24) as starting material
LCMS Method #2, retention time 0.56 min, detected mass 263.12 [M+H]$^+$

6-(1-Pyrimidin-2-yl-piperidin-4-yloxy)-isoquinoline-hydrochloride (157)

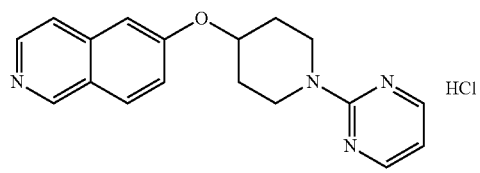 [SMILES: c1cnc(N2CCC(Oc3ccc4cnccc4c3)CC2)nc1 ; Cl]

150 mg of 6-(Piperidine-4-yloxy)-isoquinoline hydrochloride (124) are dissolved in 10 mL of dry pyridine. 177 mg of triethylamine and 69 mg of 4-chloropyrimidine are added and the solution is stirred at 65° C. for 6 hours. The reaction mixture is poured on brine and extracted three times with ethyl acetate. The combined organic layers are dried over magnesium sulfate, evaporated to dryness and the crude product is purified by preparative HPLC. The product is converted into the corresponding HCl salt by taking up the product in 20 mL of 1 N hydrochloric acid followed by lyophilization. Yield: 47 mg. $R_t$=1.05 min (Method #2). Detected mass: 307.1 (M+H$^+$).

6-[1-(4-Trifluoromethyl-pyrimidin-2-yl)-piperidin-4-yloxy]-isoquinoline hydrochloride (158)

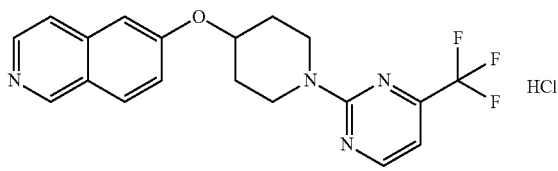 [SMILES: FC(F)(F)c1ccnc(N2CCC(Oc3ccc4cnccc4c3)CC2)n1 ; Cl]

75 mg of 6-(Piperidine-4-yloxy)-isoquinoline-Hydrochloride (124) are dissolved in 5 mL of dry pyridine and 5 mL of DMF. 55 mg 2-Chlor-4-trifluoromethyl-pyrimidine are added and the solution is stirred at 60° C. for 3 hours. The solvents are removed in vacuo and the residue is taken up in brine and extracted three times with ethyl acetate. The combined organic layers are dried over magnesium sulfate, evaporated to dryness and the crude product is purified by preparative HPLC. The product is converted into the corresponding HCl salt by taking up the product in 20 mL of 1 N hydrochloric acid followed by lyophilization. Yield: 29 mg. $R_t$=1.69 min (Method #2). Detected mass: 375.1 (M+H$^+$).

6-(1-Cyclopropyl-piperidin-4-yloxy)-isoquinoline-hydrochloride (159)

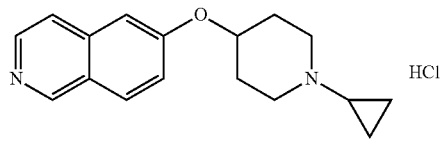 [SMILES: c1cc2cc(OC3CCN(C4CC4)CC3)ccc2cn1 ; Cl]

300 mg (1.13 mmol) 6-(Piperidine-4-yloxy)-isoquinoline hydrochloride (124) are dissolved in 10 mL of methanol. 202 mg of triethylamine, molecular sieves 4A, 600 mg of glacial acetic acid, 871 mg of (1-Ethoxy-cyclopropyloxy)-trimethylsilane and 101 mg of sodium cyanoborohydride are added successively and the reaction mixture is heated under reflux for 6 hours. The reaction mixture is cooled to room temperature, 6 mL of 2N sodium hydroxide are added and the reaction mixture is filtered. The filtrate is evaporated, the residue is taken up in dichloromethane, extracted with 2 N sodium hydroxide and brine, dried with sodium sulfate, evaporated to dryness and the crude material is purified by preparative HPLC. The product fractions are evaporated, the product is taken up in 2 N hydrochloric acid and lyophilized.
Yield: 60 mg. $R_t$=0.50 min (Method #1). Detected mass: 269.2 (M+H$^+$).

4-(2-Oxy-isoquinolin-6-yloxy)-piperidine-1-carboxylic acid tert-butyl ester (160)

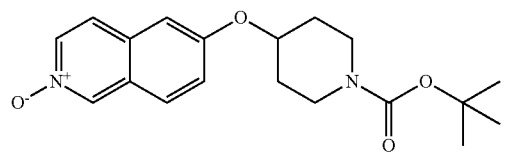 [SMILES: CC(C)(C)OC(=O)N1CCC(Oc2ccc3c[n+]([O-])ccc3c2)CC1]

3.97 g (12.1 mmol) of 4-(Isoquinolin-6-yloxy)-piperidine-1-carboxylic acid tert-butyl ester (154) are dissolved in 100 ml of dichloromethane and 4.47 g (18.1 mmol) of 3-chloroperbenzoic acid (70%) are added at room temperature. The reaction mixture is stirred for 1 h and then washed with saturated sodium bicarbonate-solution. The aqueous phase is separated and extracted with dichloromethane. The combined organic layers are dried over magnesium sulfate and evaporated, to yield 4.19 g of crude material, which can be used for further conversion without purification. $R_t$=1.46 min (Method #1). Detected mass: 345.2 (M+H$^+$).

1-Chloro-6-(piperidin-4-yloxy)-isoquinoline-hydrochloride (161)

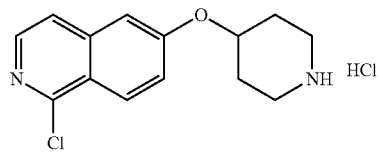 [SMILES: Clc1nccc2cc(OC3CCNCC3)ccc12 ; Cl]

3.5 g (10.16 mmol) 4-(2-Oxy-isoquinolin-6-yloxy)-piperidine-1-carboxylic acid tert-butyl ester (160) were dissolved in 250 ml of HCl-saturated ethanol at 50° C. The clear solution was concentrated i. vac. and the residue was refluxed in 50 ml POCl₃. After 3 h the POCl₃ was removed i. vac. and the residue was taken up in H₂O. The pH was adjusted to 11, by adding sodium hydroxide and the aqueous solution was extracted twice with dichloromethane. The combined organic layers were dried over magnesium sulfate and evaporated to dryness. The residue was purified by preparative HPLC, by which the title compound was obtained as trifluoroacetate. This was converted to the corresponding HCl-salt by dissolving the product in 2 N HCl, followed by lyophilization. Yield: 950 mg. $R_t$=1.03 min (Method #1). Detected mass: 263.1/265.1 (M+H⁺).

4-(1-Chloro-isoquinolin-6-yloxy)-piperidine-1-carboxylic acid tert-butyl ester (162)

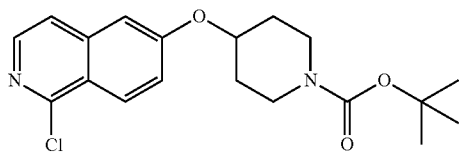 [SMILES: CC(C)(C)OC(=O)N1CCC(Oc2ccc3c(Cl)nccc3c2)CC1]

1.23 g (4.11 mmol) of 1-Chloro-6-(piperidin-4-yloxy)-isoquinoline hydrochloride (161) were dissolved in 50 ml of dichloromethane and 0.85 ml (6.15 mmol) of triethylamine were added. At 0° C. a solution of 1.09 g (5.0 mmol) of tert-butyl-carbonate in 10 ml dichloromethane was added dropwise and the mixture was allowed to stand at room temperature overnight. For working up, the mixture was washed twice with H₂O, dried over magnesium sulfate and evaporated, to yield 1.1 g of the desired product, which could be used without further purification. $R_t$=1.86 min (Method #4). Detected mass: 363.1/365.2 (M+H⁺).

4-(1-Methylamino-isoquinolin-6-yloxy)-piperidine-1-carboxylic acid tert-butyl ester (163)

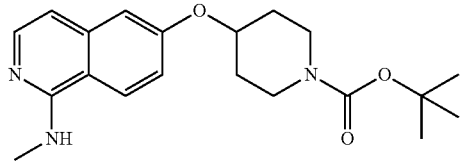 [SMILES: CNc1nccc2cc(OC3CCN(C(=O)OC(C)(C)C)CC3)ccc12]

154 mg (0.42 mmol) of 4-(1-Chloro-isoquinolin-6-yloxy)-piperidine-1-carbocyclic acid tert-butyl ester (162) were heated in 15 ml of an aqueous methylamine-solution (41%)) at 110° C. in a sealed tube. After 7 h the reaction mixture was evaporated and the residue was taken up in saturated sodium bicarbonate solution and extracted with ethyl acetate. The organic layer was separated, dried over magnesium sulfate and the solvent was removed i. vac. The residue was purified by silica gel chromatography (ethyl acetate/methanol 5:1). Yield: 45 mg. $R_t$=1.14 min (Method #4). Detected mass: 358.3 (M+H⁺).

Methyl-[6-(piperidin-4-yloxy)-isoquinolin-1-yl]-amine-hydrochloride (164)

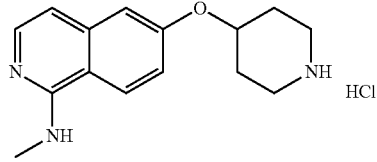 [SMILES: CNc1nccc2cc(OC3CCNCC3)ccc12 ; Cl]

4-(1-Methylamino-isoquinolin-6-yloxy)-piperidine-1-carboxylic acid tert-butyl ester (163) was converted to the deprotected title compound by the general procedure, described in AAV2, by which 34 mg of the corresponding HCl-salt could be obtained. $R_t$=0.69 min (Method #1). Detected mass: 258.3 (M+H⁺).

Following the synthetic route, described for compound 164, the following compounds were prepared starting from 4-(1-Chloro-isoquinolin-6-yloxy)-piperidine-1-carbocyclic acid tert-butyl ester (162) and the corresponding amines:

| No. | Compound | Amine | T [° C.] | Mass [MH⁺] | Retention time [min] | Method |
|---|---|---|---|---|---|---|
| 165 | ![structure] | Ethylamine; 70% in H₂O | 110° C. | 272.28 | 0.72 | 1 |
| 166 | ![structure] | Dimethylamine; 2M in THF | 110° C. | 272.29 | 0.68 | 1 |

| No. | Compound | Amine | T [° C.] | Mass [MH+] | Retention time [min] | Method |
|---|---|---|---|---|---|---|
| 167 | 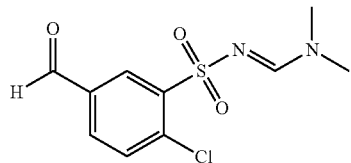 [SMILES: CN(C)/C=N/S(=O)(=O)c1cc(C=O)ccc1Cl] | Aniline; 1:1 in dioxan (v/v) | 120° C. | 320.20 | 0.88 | 1 |

2-Chloro-N-dimethylaminomethylene-5-formyl-benzenesulfonamide (168)

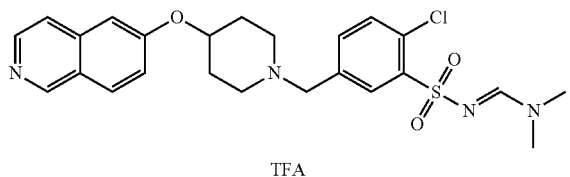 [SMILES: CN(C)/C=N/S(=O)(=O)c1cc(CN2CCC(Oc3ccc4cnccc4c3)CC2)ccc1Cl]

5.0 g (22.8 mmol) of 2-Chloro-5-formyl-benzenesulfonamide were dissolved in 50 ml of dichloromethane. 4.08 g (34.3 mmol) of dimethylformamide dimethylacetal were added and the mixture was refluxed for 2 h. After cooling to room temperature, the solution was washed twice with $H_2O$, dried over magnesium sulfate and evaporated. 5.16 g of the crude product were obtained and used in the next step without further purification. $R_t$=1.14 min (Method #1). Detected mass: 275.1/277.1 (M+H+).

2-Chloro-N-dimethylaminomethylene-5-[4-(isoquinolin-6-yloxy)-piperidin-1-ylmethyl]-benzene-sulfonamide-trifluoro acetate (169)

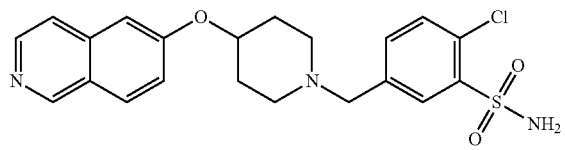 [SMILES: NS(=O)(=O)c1cc(CN2CCC(Oc3ccc4cnccc4c3)CC2)ccc1Cl]

200 mg (0.88 mmol) of 6-(piperidine-4-yloxy)-isoquinoline hydrochloride (124) were dissolved in 20 ml of methanol and 158 mg (1.56 mmol) of triethylamine were added. After stirring for 15 minutes at room temperature 467 mg (7.78 mmol) of glacial acetic acid, 482 mg (1.76 mmol) of 2-Chloro-N-dimethylaminomethylene-5-formyl-benzene-sulfonamide (168), 166 mg (2.64 mmol) of sodium cyanoborohydride and freshly dried molecular sieves were added and the mixture was refluxed for 3 h. After stirring overnight at room temperature, the mixture was filtered and the filtrate was evaporated. The residue was dissolved in dichloromethane and washed twice with saturated sodium bicarbonate solution and brine. After drying over magnesium sulfate and evaporation of the solvent, the crude product was purified by preparative HPLC, by which 133 mg of the desired product could be isolated as trifluoroacetate. $R_t$=0.87 min (Method #2), Detected mass: 487.2/489.2 (M+H+).

2-Chloro-5-[4-(isoquinolin-6-yloxy)-piperidin-1-ylmethyl]-benzenesulfonamide (170)

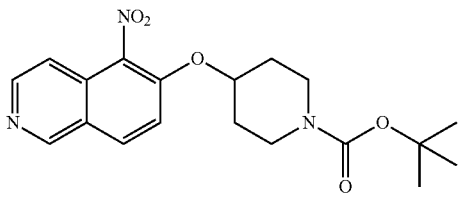 [SMILES: CC(C)(C)OC(=O)N1CCC(Oc2ccc3cnccc3c2[N+](=O)[O-])CC1]

133 mg (0.27 mmol) of 2-Chloro-N-dimethylaminomethylene-5-[4-(isoquinolin-6-yloxy)-piperidin-1-ylmethyl]-benzenesulfonamide (169) were dissolved in ethanol. After adding 50 ml of 2N NaOH, the solution was heated to 60° C. for 6 h. After cooling to room temperature, the mixture was neutralized by addition of aqueous HCl and the solvent was removed i. vac. The residue was stirred with ethanol, the inorganic salts were filtered off and the filtrate was evaporated. $R_t$=0.78 min (Method #2), Detected mass: 432.1 (M+H+).

4-(5-Nitro-isoquinolin-6-yloxy)-piperidine-1-carboxylic acid tert-butyl ester (171)

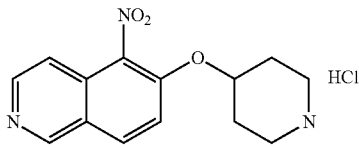 [SMILES: O=[N+]([O-])c1c(OC2CCNCC2)ccc2cnccc12 ; Cl]

90 mg (0.47 mmol) 6-Fluoro-5-nitro-isoquinoline (152) were treated with 4-Hydroxy-piperidine-1-carboxylic acid tert-butyl ester following the method described for the preparation of compound 154.

5-Nitro-6-(piperidin-4-yloxy)-isoquinoline-hydrochloride (172)

18.5 mg (0.05 mmol) 4-(5-Nitro-isoquinolin-6-yloxy)-piperidine-1-carboxylic acid tert-butyl ester (171) were deprotected following the procedure, described in AAV2, by which 12.5 mg of the title compound could be isolated as HCl-salt. $R_t$=0.57 min (Method #1). Detected mass: 274.2 (M+H+).

7-Chloro-6-(piperidin-4-yloxy)-isoquinoline-hydrochloride (173)

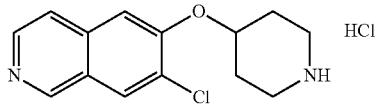 [SMILES: Clc1cc2cnccc2cc1OC1CCNCC1 ; Cl]

Starting from 7-Chloro-6-fluoro-isoquinoline (150), the title compound was prepared by the same synthetic route as for compound 124. $R_t$=0.66 min (Method #1), detected mass: 263.1/265.1 (M+H$^+$).

Synthetic procedure for the generation of 3,6-disubstituted isoquinolines

General reaction scheme:

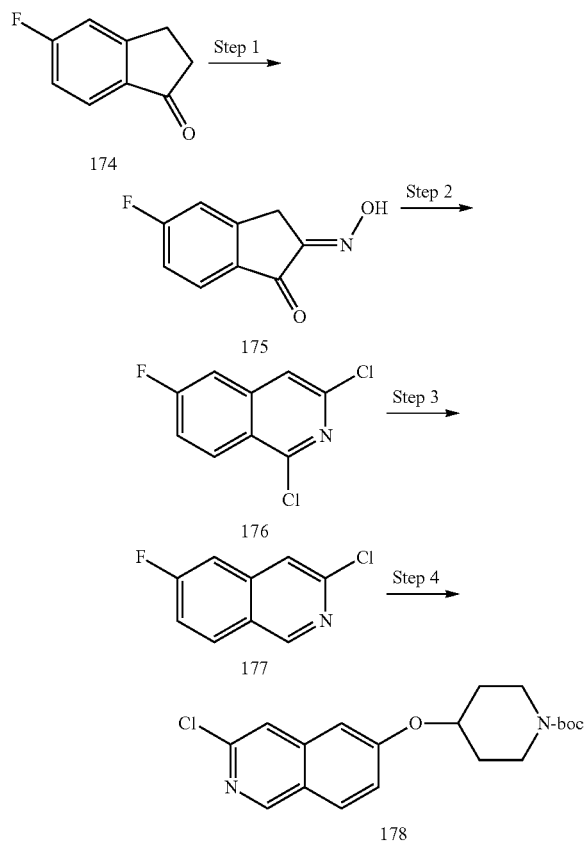

Step 1

188 g of 5-Fluoro-indanone-1 (174) were dissolved in 1.8 l of diethyl ether, 50 ml of EtOH saturated with HCl are added at 0° C. and 1.1 l of a 15% ethyl nitrite solution in ether is added over 1 hour.

The solution is allowed to stir for an additional 3 hours to reach room temperature, then the solvent is removed partially and the precipitated product is collected by filtration.

Step 2

129 g of the product from Step 1 was added to a mixture of 170 g of PCl$_5$ in 2 l of POCl$_3$. Then gaseous HCl was added at 0° C. until saturation of the solution was reached. The remaining mixture was heated to 60° C. for 6 h, the solvent partially removed in vacuo and the residue was hydrolyzed on a crushed ice/water mixture. The precipitated product is isolated by filtration.

Step 3

155 g of product from Step 2 were added to a mixture of 740 ml HOAc and 330 ml HI (57%) containing 53 g of red phosphorous. After heating to reflux for 4 hours, the solution was treated with concentrated NaOH (until pH=8) and the precipitated product is isolated by filtration.

Step 4

16.5 g of N-Boc-4-hydroxypiperidine were dissolved in 210 ml of diglyme and treated with 4.1 g 50% NaH under nitrogen. The resulting mixture was stirred for 1 h at room temperature, then 14.8 g of the product from Step 4 was added. The mixture was allowed to stir for 1 day at room temperature, then 100 ml of toluene were added and the resulting mixture was washed with water 3 times. The organic phases were collected and the solvent was removed in vacuo.

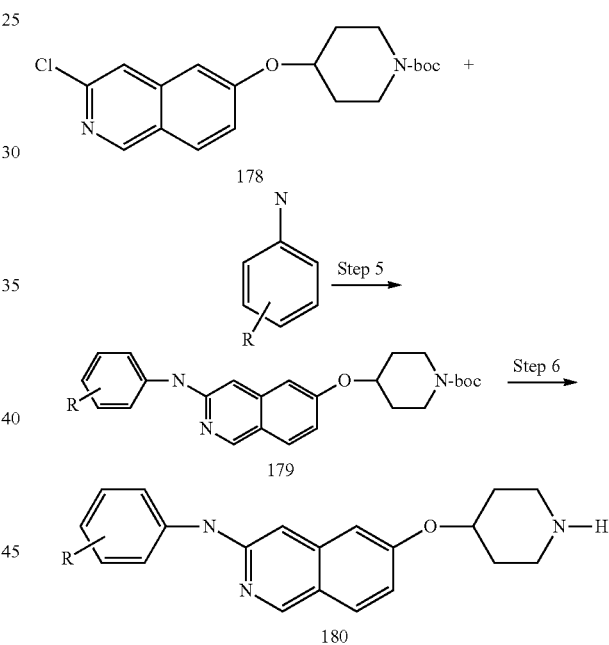

Step 5

100 mg of compound 178 and 1.1 equivalents of the corresponding aniline are dissolved in 5 ml of dioxane, 350 mg of Cs$_2$CO$_3$, 20 mg of Pd(OAc)$_2$ and 60 mg of XANTHPHOS are added and the resulting mixture is heated to reflux under nitrogen until the starting material is consumed. (reaction is monitored by LCMS) The solvent is removed in vacuo and the residue is subjected to chromatography on a HPLC system.

Step 6

The products of Step 5 are dissolved in 5 ml of ethanol saturated with gaseous HCl. After stirring for 5 h the desired product is isolated by removal of the solvent in vacuo.

All 3,5,6-trisubstituted derivatives were synthesized according to the procedure illustrated by the synthesis of compound 184. For synthesis of compound 185, acetamide was used as amine component in the Pd coupling step.

Synthesis of 4-(5-Bromo-3-chloro-isoquinolin-6-yloxy)-piperidine-1-carboxylic acid tert-butyl ester (181)

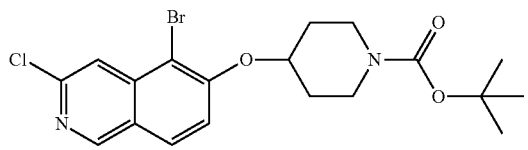 [SMILES: CC(C)(C)OC(=O)N1CCC(Oc2ccc3cnc(Cl)cc3c2Br)CC1]

200 mg of 4-(3-Chloro-isoquinolin-6-yloxy)-piperidine-1-carboxylic acid tert-butyl ester (178) were dissolved in 5 ml of $CH_3CN$ and heated to 85° C. Then a mixture of 148 mg of N-bromosuccinimide and 9 mg of AIBN was added as solid and the resulting mixture was heated to reflux for 1 h. The solvent was removed in vacuo and the residue subjected to flash column chromatography. The yield of the isolated product was 41% LCMS: detected mass: 441.03, $R_t$=2.41 min (Method #1)

Synthesis of 4-[3-Chloro-5-(4-fluoro-phenyl)-isoquinolin-6-yloxy]-piperidine-1-carboxylic acid tert-butyl ester (182)

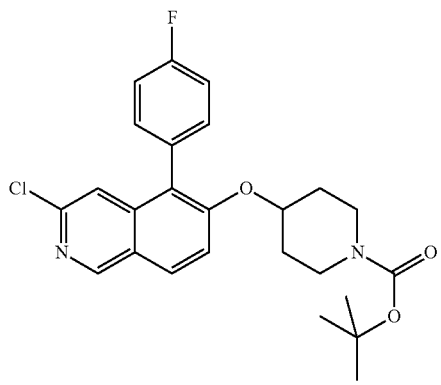 [SMILES: CC(C)(C)OC(=O)N1CCC(Oc2ccc3cnc(Cl)cc3c2-c2ccc(F)cc2)CC1]

150 mg of 4-(5-Bromo-3-chloro-isoquinolin-6-yloxy)-piperidine-1-carboxylic acid tert-butyl ester (181) were dissolved in a mixture of 9 ml of dioxane and 3 ml of water, 47 mg of 4-fluoro-benzene-boronic acid, 47 mg of $Na_2CO_3$ and 40 mg of $Pd(PPh_3)_4$ were added and the resulting mixture was heated to 100° C. for 6 h. The solvent was removed in vacuo and the residue subjected to chromatography on a HPLC system. Yield: 44% LCMS: detected mass: 457.22, $R_t$=2.45 min (Method #1)

Synthesis of 4-[5-(4-Fluoro-phenyl)-3-(3,4,5-trimethoxy-phenylamino)-isoquinolin-6-yloxy]-piperidine-1-carboxylic acid tert-butyl ester (183)

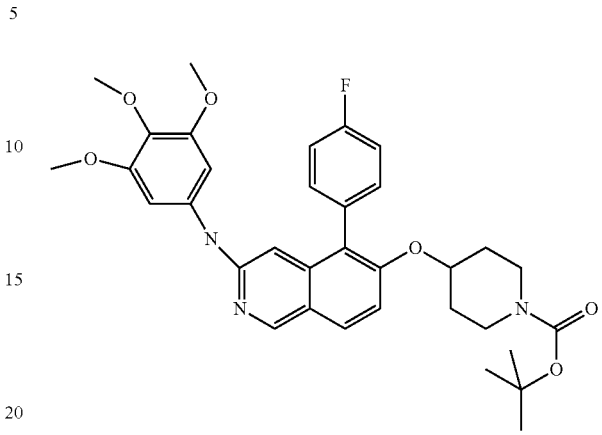

70 mg of 4-[3-Chloro-5-(4-fluoro-phenyl)-isoquinolin-6-yloxy]-piperidine-1-carboxylic acid tert-butyl ester(182) were dissolved in 7 ml of toluene, 20 mg of $Pd(OAc)_2$, 60 mg of XANTHPHOS, 400 mg of $Cs_2CO_3$ and 30 mg of 3,4,5 trimethoxyaniline were added and the resulting mixture was heated to 100° C. for 6 h. Then the solvent was removed in vacuo and the residue subjected to chromatography on a HPLC system. The yield of isolated product was 24%

LCMS: detected mass: 604.17, RT=1.81 min (Method #1)

Synthesis of [5-(4-Fluoro-phenyl)-6-(piperidin-4-yloxy)-isoquinolin-3-yl]-(3,4,5-trimethoxy-phenyl)-amine (184)

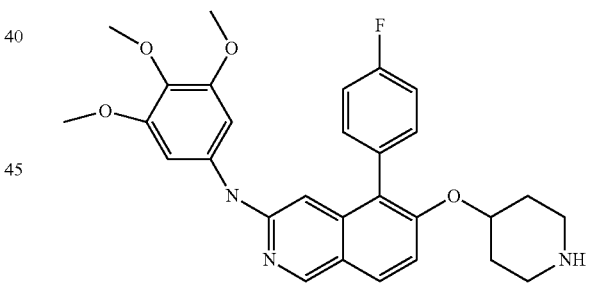

20 mg of 4-[5-(4-Fluoro-phenyl)-3-(3,4,5-trimethoxy-phenylamino)-isoquinolin-6-yloxy]-piperidine-1-carboxylic acid tert-butyl ester (183) were dissolved in 5 ml of ethanol saturated with HCl (gaseous). The resulting mixture was stirred for 1 h, then the solvent was evaporated and the product collected. Yield: 85%

LCMS: detected mass: 503.22, $R_t$=1.22 min (Method #1)

| No. | Compound | RT | Method | Detected Mass [MH+] |
|---|---|---|---|---|
| 185 | ![compound] | 0.12 | #2 | 244.14 |

| No. | Compound | RT | Method | Detected Mass [MH+] |
|---|---|---|---|---|
| 186 | | 0.19 | #2 | 286.18 |
| 187 | | 0.17 | #2 | 335.21 |
| 188 | HCl | 1.02 | #2 | 335.21 |
| 189 | HCl | 1.02 | #2 | 335.21 |
| 190 | HCl | 1.02 | #2 | 335.21 |
| 191 | | 1.02 | #2 | 335.21 |
| 192 | | 1.32 | #2 | 335.20 |

-continued

| No. | Compound | RT | Method | Detected Mass [MH⁺] |
|---|---|---|---|---|
| 193 | | 1.21 | #2 | 349.21 |
| 194 | | 0.11 | #2 | 329.34 |
| 195 | | 0.17 | #2 | 371.32 |
| 196 | | 0.15 | #2 | 316.21 |
| 197 | | 1.18 | #2 | 322.25 |

-continued
| No. | Compound | RT | Method | Detected Mass [MH+] |
|---|---|---|---|---|
| 198 | 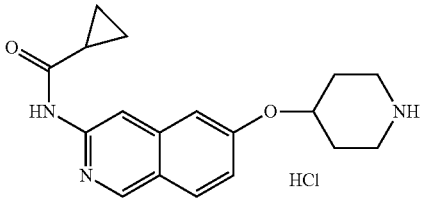 [SMILES: O=C(Nc1cc2cc(OC3CCNCC3)ccc2cn1)C1CC1 ; Cl] | 1..18 | #2 | 312.18 |
| 199 | 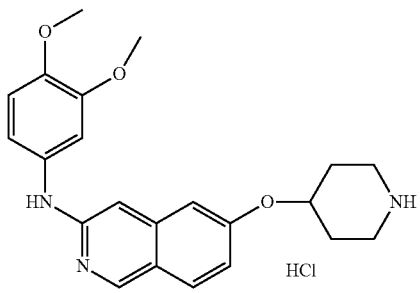 [SMILES: COc1ccc(Nc2cc3cc(OC4CCNCC4)ccc3cn2)cc1OC ; Cl] | 1.29 | #2 | 380.30 |
| 200 | 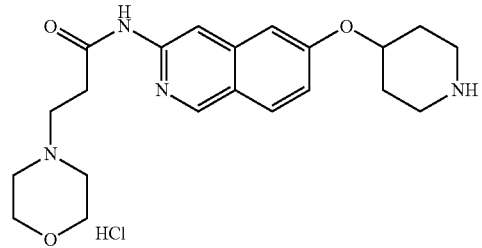 [SMILES: O=C(CCN1CCOCC1)Nc1cc2cc(OC3CCNCC3)ccc2cn1 ; Cl] | 0.63 | #2 | 385.29 |
| 201 | 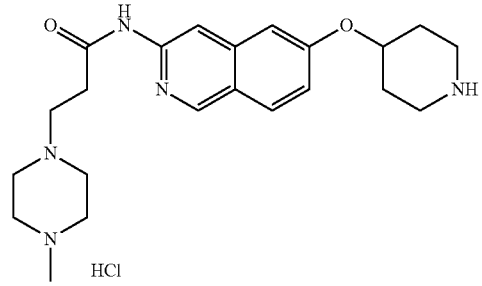 [SMILES: CN1CCN(CCC(=O)Nc2cc3cc(OC4CCNCC4)ccc3cn2)CC1 ; Cl] | 0.2 | #2 | 398.34 |
| 202 | 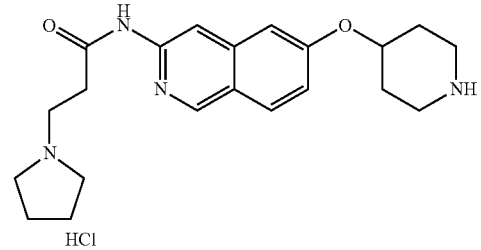 [SMILES: O=C(CCN1CCCC1)Nc1cc2cc(OC3CCNCC3)ccc2cn1 ; Cl] | 0.18 | #2 | 369.30 |

-continued

| No. | Compound | RT | Method | Detected Mass [MH+] |
|---|---|---|---|---|
| 203 | | 0.2 | #2 | 400.27 |
| 204 | | 0.16 | #2 | 455.27 |
| 205 | | 0.16 | #2 | 483.34 |
| 206 | | 0.16 | #2 | 434.26 |

| No. | Compound | RT | Method | Detected Mass [MH⁺] |
|---|---|---|---|---|
| 206A | (structure shown, HCl salt) | 0.15 | #2 | 452.30 |
| 207 | (structure shown, CHIRAL) | 0.15 | #2 | 403.25 |
| 208 | (structure shown, HCl salt) | 1.02 | #2 | 321.17 |
| 209 | (structure shown) | 1.02 | #2 | 321.17 |
| 210 | (structure shown, HCl salt) | 1.06 | #2 | 321.17 |

-continued
| No. | Compound | RT | Method | Detected Mass [MH+] |
|---|---|---|---|---|
| 211 | 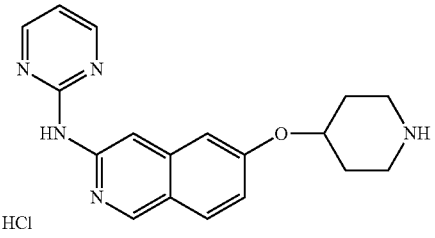 [SMILES: c1cnc(Nc2cc3cc(OC4CCNCC4)ccc3cn2)nc1 ; Cl] HCl | 0.85 | #2 | 322.17 |
| 212 | 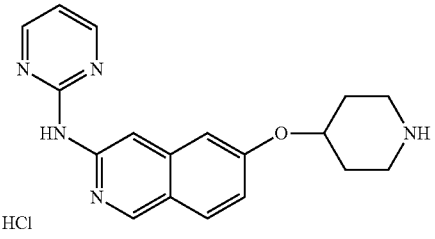 [SMILES: c1cnc(Nc2cc3cc(OC4CCNCC4)ccc3cn2)nc1 ; Cl] HCl | 0.85 | #2 | 322.17 |
| 213 | 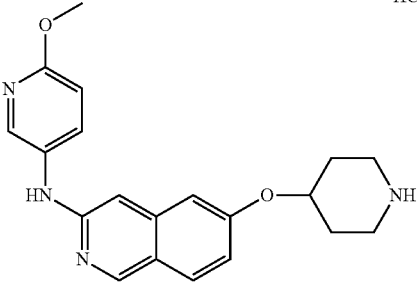 HCl | 0.89 | #2 | 351.18 |
| 214 | 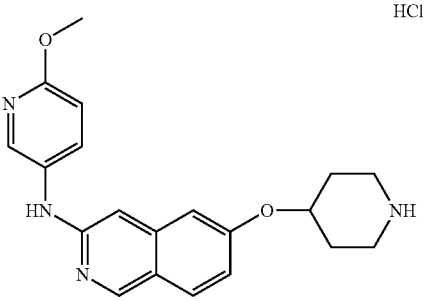 [SMILES: Cl ; COc1ccc(Nc2cc3cc(OC4CCNCC4)ccc3cn2)cn1] HCl | 0.89 | #2 | 351.18 |
| 215 | 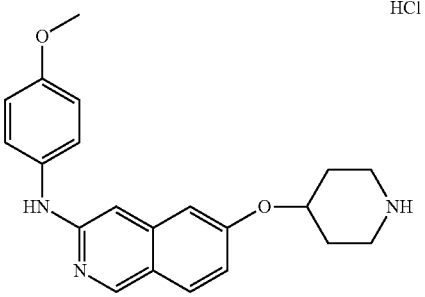 [SMILES: Cl ; COc1ccc(Nc2cc3cc(OC4CCNCC4)ccc3cn2)cc1] HCl | 1.03 | #2 | 350.19 |

-continued

| No. | Compound | RT | Method | Detected Mass [MH+] |
|---|---|---|---|---|
| 216 | 2,5-dimethoxyphenyl-NH-isoquinoline-O-piperidine · HCl | 1 | #2 | 380.20 |
| 217 | 2,5-dimethoxyphenyl-NH-isoquinoline-O-piperidine · HCl | 1 | #2 | 380.20 |
| 218 | 2-methylpyridin-4-yl-NH-isoquinoline-O-piperidine · HCl | 0.95 | #2 | 335.19 |
| 219 | 6-fluoropyridin-3-yl-NH-isoquinoline-O-piperidine · HCl | 1 | #2 | 339.16 |
| 220 | 3,5-dimethoxyphenyl-NH-isoquinoline-O-piperidine | 1.05 | #1 | 380.20 |

-continued
| No. | Compound | | RT | Method | Detected Mass [MH+] |
|---|---|---|---|---|---|
| 221 | 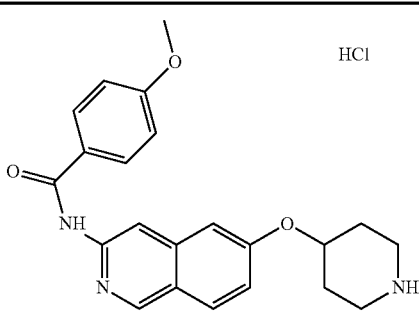 | HCl | 1.06 | #1 | 378.18 |
| 222 | 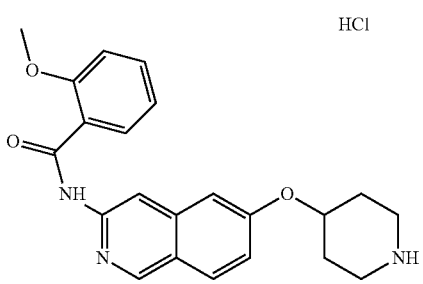 [SMILES: Cl ; COc1ccccc1C(=O)Nc1cc2cc(OC3CCNCC3)ccc2cn1] | HCl | 1.17 | #1 | 378.18 |
| 223 | 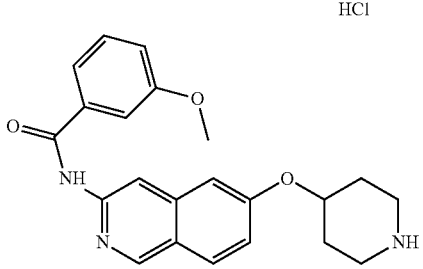 [SMILES: Cl ; COc1cccc(C(=O)Nc2cc3cc(OC4CCNCC4)ccc3cn2)c1] | HCl | 1.12 | #1 | 378.18 |
| 224 | 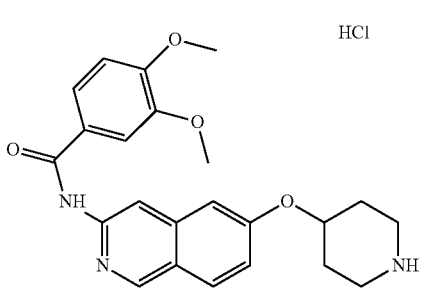 [SMILES: Cl ; COc1ccc(C(=O)Nc2cc3cc(OC4CCNCC4)ccc3cn2)cc1OC] | HCl | 1.04 | #1 | 408.19 |
| 225 | 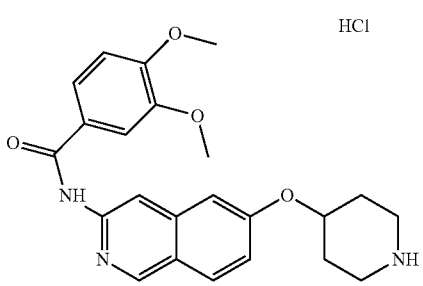 [SMILES: Cl ; COc1ccc(C(=O)Nc2cc3cc(OC4CCNCC4)ccc3cn2)cc1OC] | HCl | 1.04 | #1 | 408.19 |

-continued

| No. | Compound | RT | Method | Detected Mass [MH+] |
|---|---|---|---|---|
| 226 | HCl | 0.95 | #1 | 378.18 |
| 227 | | 1.1 | #1 | 432.19 |
| 228 | | 1.02 | #1 | 410.21 |
| 230 | | 1.12 | #1 | 384.15 |
| 231 | | 1.28 | #1 | 412.20 |

-continued

| No. | Compound | | RT | Method | Detected Mass [MH+] |
|---|---|---|---|---|---|
| 232 | (structure) | HCl | 1.31 | #1 | 404.16 |
| 233 | (structure) | HCl | 1.15 | #1 | 433.22 |
| 234 | (structure) | HCl | 1.25 | #1 | 400.15 |
| 235 | (structure) | HCl | 1.39 | #1 | 442.21 |
| 236 | (structure) | HCl | 1 | #1 | 350.19 |

-continued
| No. | Compound | RT | Method | Detected Mass [MH+] |
|---|---|---|---|---|
| 237 | 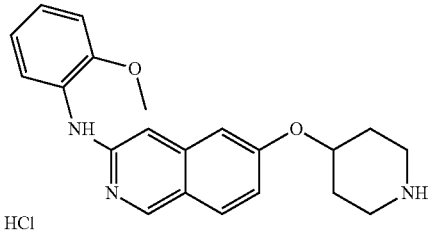 [SMILES: COc1ccccc1Nc1cc2cc(OC3CCNCC3)ccc2cn1 ; Cl] HCl | 0.99 | #1 | 350.19 |
| 238 | 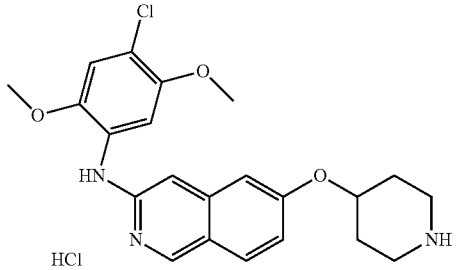 [SMILES: COc1cc(Nc2cc3cc(OC4CCNCC4)ccc3cn2)c(OC)cc1Cl ; Cl] HCl | 1.13 | #1 | 414.16 |
| 239 | 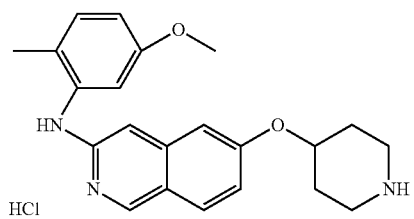 [SMILES: COc1ccc(C)c(Nc2cc3cc(OC4CCNCC4)ccc3cn2)c1 ; Cl] HCl | 1.03 | #1 | 364.20 |
| 240 | 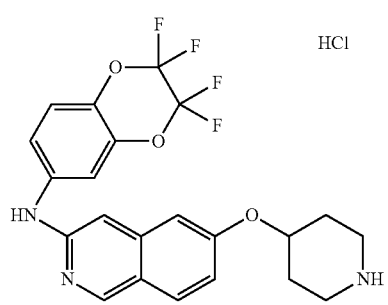 [SMILES: FC1(F)Oc2ccc(Nc3cc4cc(OC5CCNCC5)ccc4cn3)cc2OC1(F)F ; Cl] HCl | 1.5 | #1 | 450.14 |
| 241 | 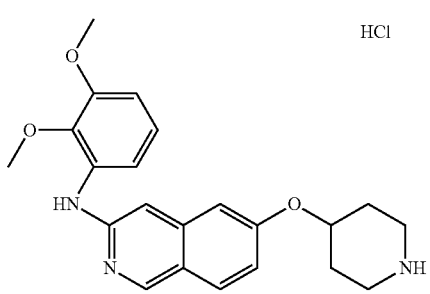 [SMILES: COc1cccc(Nc2cc3cc(OC4CCNCC4)ccc3cn2)c1OC ; Cl] HCl | 0.99 | #1 | 380.20 |
| 242 | 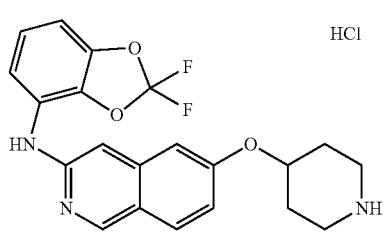 [SMILES: FC1(F)Oc2cccc(Nc3cc4cc(OC5CCNCC5)ccc4cn3)c2O1 ; Cl] HCl | 1.25 | #1 | 400.15 |

-continued
| No. | Compound | | RT | Method | Detected Mass [MH+] |
|---|---|---|---|---|---|
| 243 | 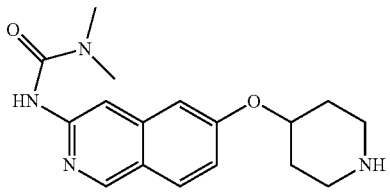 | HCl | 0.75 | #1 | 315.18 |
| 244 | 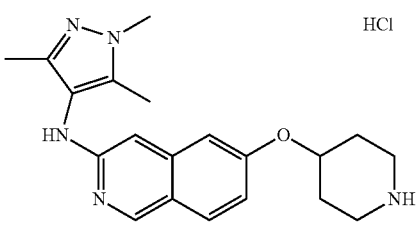 [SMILES: Cc1nn(C)c(C)c1Nc1cc2cc(OC3CCNCC3)ccc2cn1 ; Cl] | HCl | 0.83 | #1 | 352.21 |
| 245 | 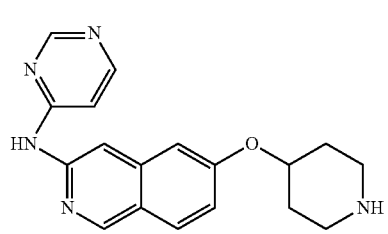 | HCl | 0.73 | #1 | 322.17 |
| 246 | 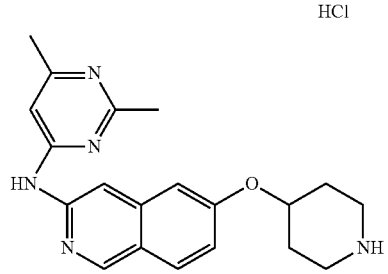 [SMILES: Cl ; Cc1cc(Nc2cc3cc(OC4CCNCC4)ccc3cn2)nc(C)n1] | HCl | 0.84 | #1 | 350.20 |
| 247 | 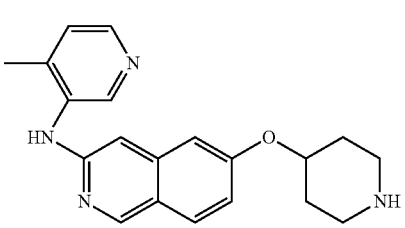 HCl | | 0.85 | #1 | 335.19 |
| 248 | 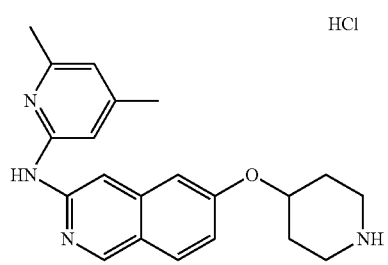 [SMILES: Cl ; Cc1cc(C)nc(Nc2cc3cc(OC4CCNCC4)ccc3cn2)c1] | HCl | 1.05 | #1 | 349.20 |

| No. | Compound | | RT | Method | Detected Mass [MH+] |
|---|---|---|---|---|---|
| 249 | (3,4-dimethylphenyl-NH-isoquinoline-6-O-piperidine) | HCl | 1.1 | #1 | 348.21 |
| 250 | (4-chloro-2-methylphenyl-NH-isoquinoline-6-O-piperidine) | HCl | 1.1 | #1 | 368.15 |
| 251 | (4-SCF3-phenyl-NH-isoquinoline-6-O-piperidine) | HCl | 1.33 | #1 | 420.14 |
| 252 | (2-chloro-4-methylphenyl-NH-isoquinoline-6-O-piperidine) | HCl | 1.12 | #1 | 368.15 |
| 253 | (2-chlorophenyl-NH-isoquinoline-6-O-piperidine) | HCl | 1.04 | #1 | 354.14 |
| 254 | (2,4-dimethylphenyl-NH-isoquinoline-6-O-piperidine) | HCl | 1.07 | #1 | 348.21 |

| No. | Compound | | RT | Method | Detected Mass [MH+] |
|---|---|---|---|---|---|
| 255 | 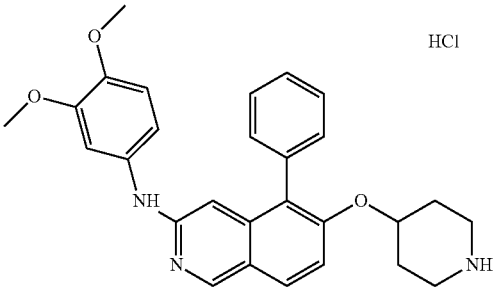 [SMILES: COc1ccc(Nc2cc3c(-c4ccccc4)c(OC4CCNCC4)ccc3cn2)cc1OC ; Cl] | HCl | 1.15 | #1 | 456.23 |
| 256 | 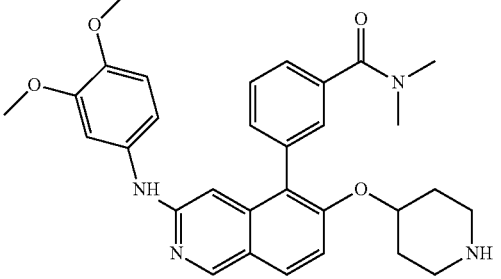 | HCl | 1.11 | #1 | 527.27 |
| 257 | 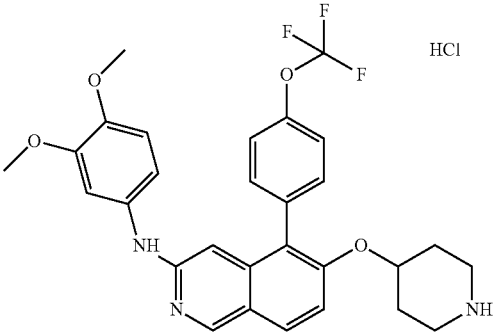 [SMILES: COc1ccc(Nc2cc3c(-c4ccc(OC(F)(F)F)cc4)c(OC4CCNCC4)ccc3cn2)cc1OC ; Cl] | HCl | 1.36 | #1 | 540.21 |
| 258 | 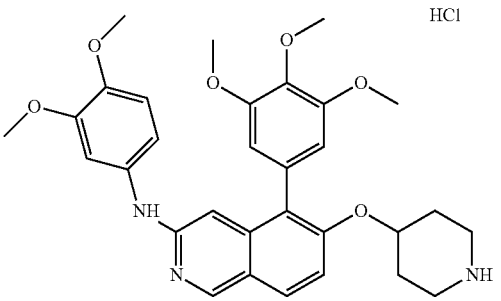 [SMILES: Cl ; COc1ccc(Nc2cc3c(-c4cc(OC)c(OC)c(OC)c4)c(OC4CCNCC4)ccc3cn2)cc1OC] | HCl | 1.15 | #1 | 546.26 |
| 259 | 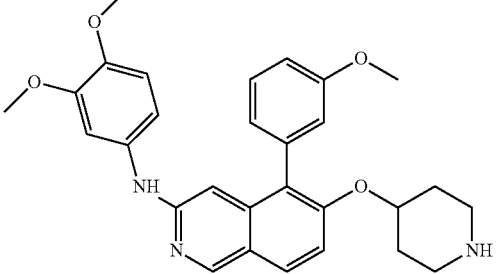 | HCl | 1.07 | #1 | 486.24 |

-continued

| No. | Compound | RT | Method | Detected Mass [MH+] |
|---|---|---|---|---|
| 260 | | 1.08 | #1 | 527.27 |
| 261 | HCl | 0.95 | #1 | 364.17 |
| 262 | HCl | 1.08 | #1 | 450.24 |
| 263 | HCl | 1.14 | #1 | 486.24 |
| 264 | HCl | 1.03 | #1 | 364.20 |

| No. | Compound | RT | Method | Detected Mass [MH+] |
|---|---|---|---|---|
| 265 | 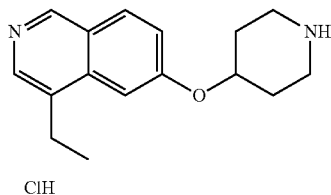 [SMILES: CCc1cncc2ccc(OC3CCNCC3)cc12 ; Cl] HCl | 1.11 | #1 | 390.22 |

4-Ethyl-6-(piperidin-4-yloxy)-isoquinoline (266)

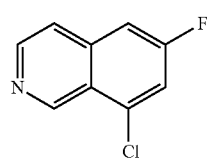 [SMILES: Fc1cc(Cl)c2cnccc2c1]

ClH

The compound 266 was synthesized in a similar fashion as described for compound 90, using ethyl iodide. LCMS Method #1, retention time 0.98 min, detected mass 257.31 [M+H]+

Also using the same reaction sequence as for the synthesis of 6-Fluoro-isoquinoline (23), the following two compounds were obtained:

8-Chloro-6-fluoro-isoquinoline (267)

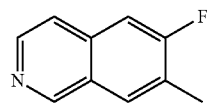

$R_t$=0.83 min (Method #1). Detected mass: 182.12 (M+H+).

6-Fluoro-7-Methylisoquinoline (268)

$R_t$=0.70 min (Method #TOP). Detected mass: 162.3 (M+H+).

8-Chloro-6-(Piperidin-4-yloxy)-isoquinoline hydrochloride (269)

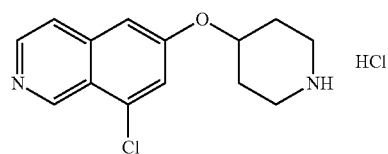 [SMILES: Clc1cc(OC2CCNCC2)cc2ccncc12 ; Cl]

8-Chloro-6-(Piperidin-4-yloxy)-isoquinoline hydrochloride (269) was obtained in a similar fashion as described above for the synthesis of (124), starting from 267 $R_t$=0.63 min (Method #1). Detected mass: 263.14 (M+H+).

6-(Piperidin-4-yloxy)-7-Methyl isoquinoline hydrochloride (270)

6-(Piperidin-4-yloxy)-7-methyl isoquinoline hydrochloride (270) was obtained in a similar fashion as described above for the synthesis of (124), starting from 268 $R_t$=0.64 min (Method #1). Detected mass: 243.18 (M+H+).

The following set of compounds was obtained the same way, following the reductive amination procedure used to obtain examples 93-123 using 269, 129 or 270, respectively and the corresponding aldehydes as starting material. All LCMS in the following tables were obtained using LCMS method #2.

| Example No | Formula | $T_R$ | Mass [MH$^+$] |
|---|---|---|---|
| 271 | 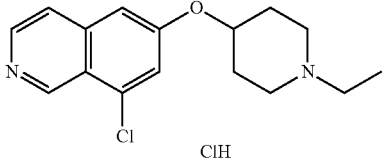 [SMILES: CCN1CCC(Oc2cc(Cl)c3cnccc3c2)CC1 ; Cl] ClH | 0.71 | 291.09 |
| 272 | 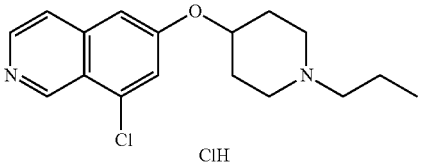 [SMILES: CCCN1CCC(Oc2cc(Cl)c3cnccc3c2)CC1 ; Cl] ClH | 0.87 | 305.11 |
| 273 | 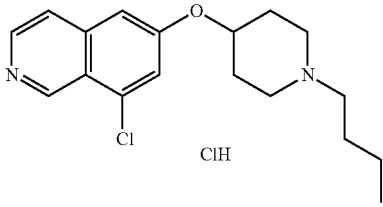 [SMILES: CCCCN1CCC(Oc2cc(Cl)c3cnccc3c2)CC1 ; Cl] ClH | 0.85 | 319.11 |
| 274 | 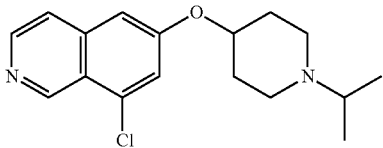 ClH | 0.69 | 305.10 |
| 275 | 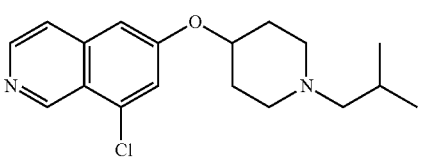 ClH | 0.85 | 319.20 |
| 276 | 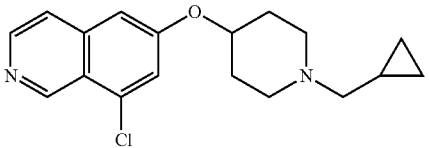 ClH | 0.79 | 317.10 |
| 277 | 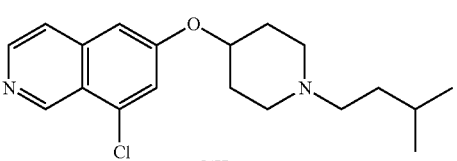 ClH | 0.92 | 333.12 |
| 278 | 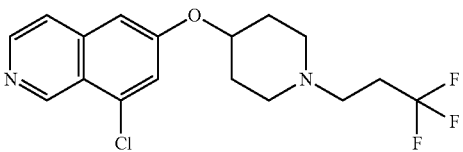 ClH | 0.87 | 359.06 |

-continued
| Example No | Formula | $T_R$ | Mass [MH$^+$] |
|---|---|---|---|
| 279 | 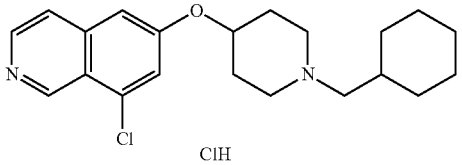 [SMILES: Clc1cc(OC2CCN(CC3CCCCC3)CC2)cc2ccncc12 ; Cl] ClH | 1.01 | 359.15 |
| 280 | 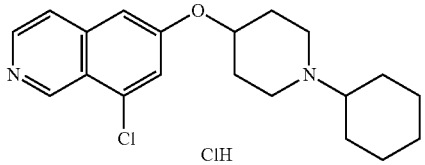 [SMILES: Clc1cc(OC2CCN(C3CCCCC3)CC2)cc2ccncc12 ; Cl] ClH | 0.90 | 345.13 |
| 281 | 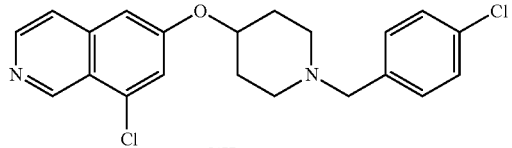 ClH | 1.02 | 387.06 |
| 282 | 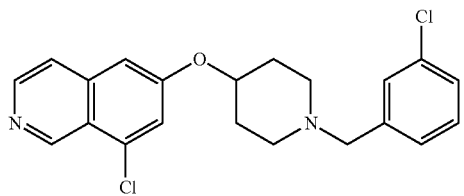 ClH | 1.09 | 387.05 |
| 283 | 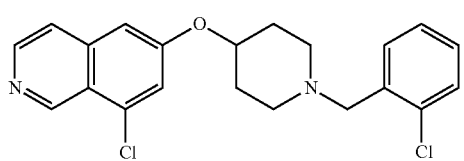 ClH | 1.05 | 387.06 |
| 284 | 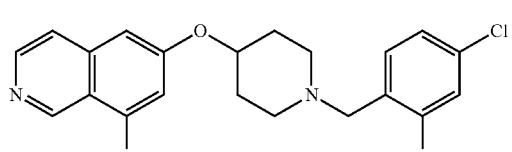 ClH | 1.10 | 421.02 |
| 285 | 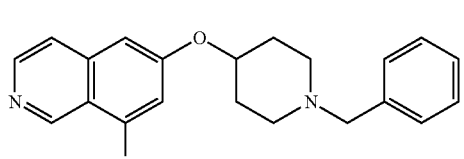 ClH | 0.95 | 353.10 |
| 286 | 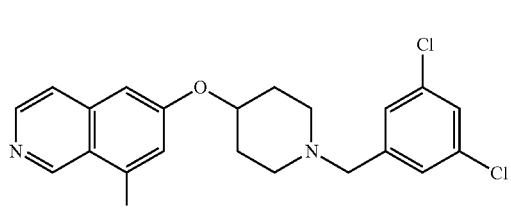 ClH | 1.14 | 421.02 |

-continued

| Example No | Formula | $T_R$ | Mass [MH$^+$] |
|---|---|---|---|
| 287 | | 1.00 | 367.10 |
| 288 | | 1.13 | 421.06 |
| 289 | | 0.63 | 354.11 |
| 290 | | 0.90 | 354.11 |
| 291 | | 0.46 | 275.33 |
| 292 | | 0.57 | 289.21 |
| 293 | | 0.73 | 303.22 |
| 294 | | 0.52 | 289.25 |

-continued
| Example No | Formula | $T_R$ | Mass [MH$^+$] |
|---|---|---|---|
| 295 | 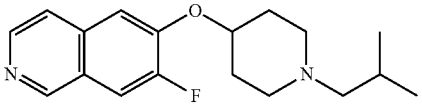 ClH | 0.65 | 303.23 |
| 296 | 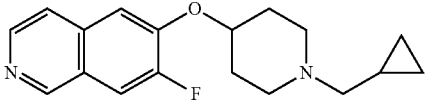 ClH | 0.63 | 301.20 |
| 297 | 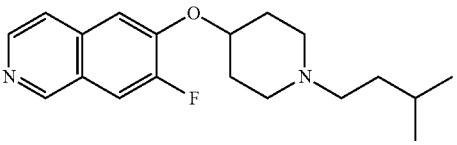 ClH | 0.90 | 317.26 |
| 298 | 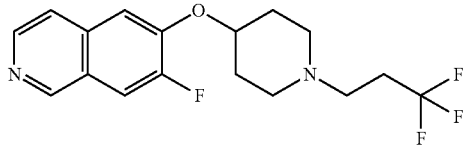 ClH | 0.66 | 343.21 |
| 299 | 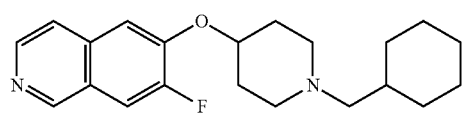 ClH | 0.96 | 343.27 |
| 300 | 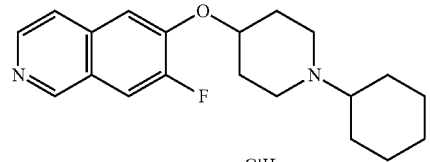 ClH | 0.72 | 329.30 |
| 301 | 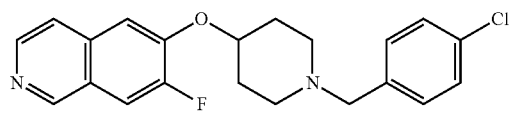 ClH | 0.97 | 371.19 |
| 302 | 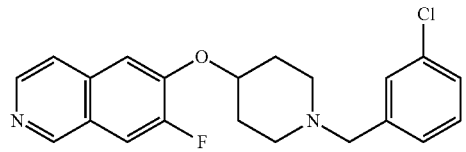 ClH | 0.95 | 371.19 |

-continued
| Example No | Formula | $T_R$ | Mass [MH$^+$] |
|---|---|---|---|
| 303 | 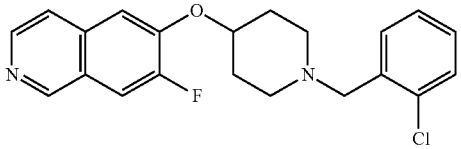 ClH | 0.88 | 371.19 |
| 304 | 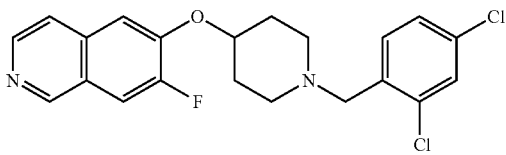 ClH | 1.02 | 405.15/ 407.15 |
| 305 | 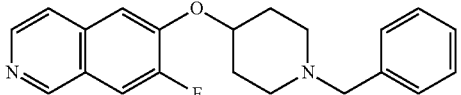 ClH | 0.83 | 337.24 |
| 306 | 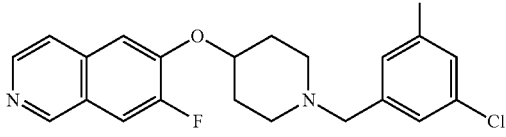 ClH | 1.07 | 405.19/ 407.19 |
| 307 | 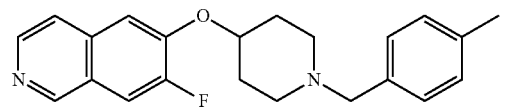 ClH | 0.94 | 351.28 |
| 308 | 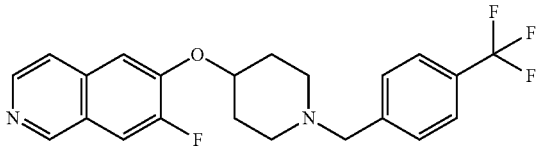 ClH | 1.05 | 405.24 |
| 309 | 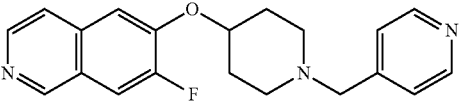 ClH | 0.23 | 338.23 |
| 310 | 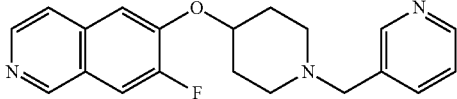 ClH | 0.49 | 338.23 |

-continued

| Example No | Formula | $T_R$ | Mass [MH$^+$] |
|---|---|---|---|
| 311 | 7-fluoro-6-[1-(pyridin-2-ylmethyl)piperidin-4-yloxy]isoquinoline · ClH | 0.67 | 338.23 |
| 312 | 7-fluoro-6-{1-[4-(methylsulfonyl)benzyl]piperidin-4-yloxy}isoquinoline · ClH | 0.70 | 415.25 |
| 313 | 7-fluoro-6-{1-[5-fluoro-2-(methylsulfonyl)benzyl]piperidin-4-yloxy}isoquinoline · ClH | 0.74 | 433.24 |
| 314 | 7-fluoro-6-[1-(naphthalen-2-ylmethyl)piperidin-4-yloxy]isoquinoline · ClH | 1.10 | 387.26 |
| 315 | 7-fluoro-6-[1-(naphthalen-1-ylmethyl)piperidin-4-yloxy]isoquinoline · ClH | 1.05 | 387.26 |
| 316 | 7-fluoro-6-{1-[(pyrrolidin-3-yl)methyl]piperidin-4-yloxy}isoquinoline · ClH | 0.12 | 330.24 |

-continued
| Example No | Formula | T_R | Mass [MH+] |
|---|---|---|---|
| 317 | Chiral 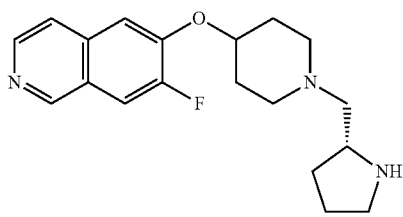 ClH | 0.28 | 330.27 |
| 318 | 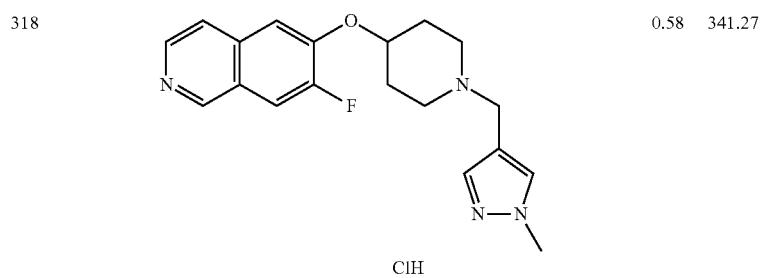 ClH | 0.58 | 341.27 |
| 319 | 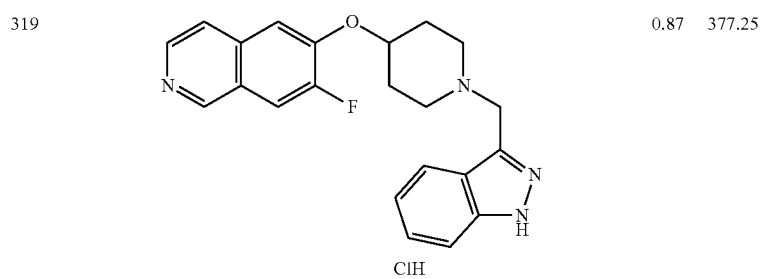 ClH | 0.87 | 377.25 |
| 320 | 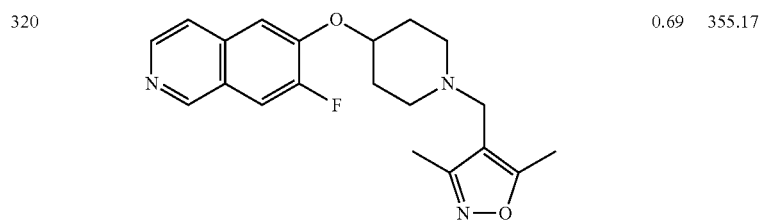 ClH | 0.69 | 355.17 |
| 321 | 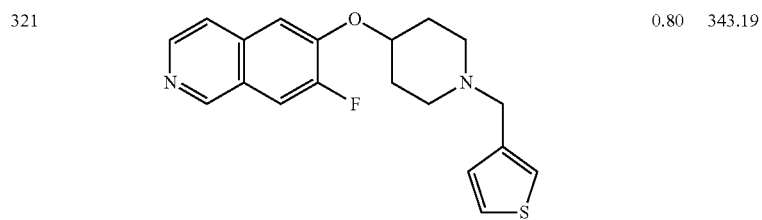 ClH | 0.80 | 343.19 |
| 322 | 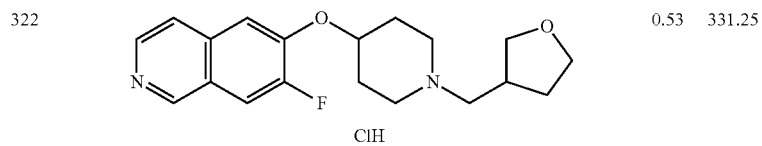 ClH | 0.53 | 331.25 |

-continued
| Example No | Formula | $T_R$ | Mass [MH$^+$] |
|---|---|---|---|
| 323 | 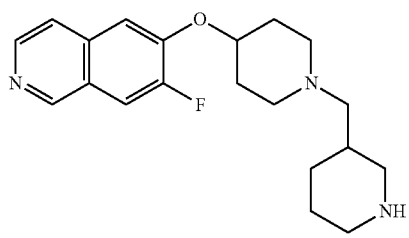 ClH | 0.18 | 344.30 |
| 324 | 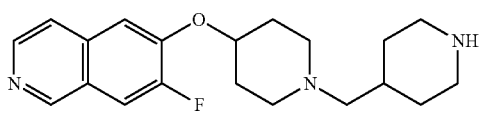 ClH | 0.14 | 344.29 |
| 325 | 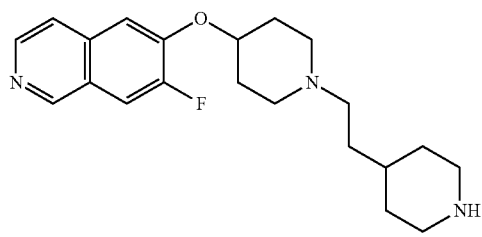 ClH | 0.14 | 358.29 |
| 326 | 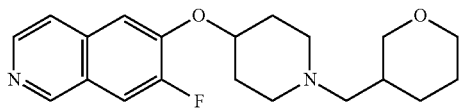 ClH | 0.62 | 345.24 |
| 327 | 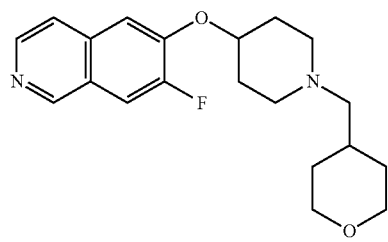 ClH | 0.60 | 345.27 |
| 328 | Chiral 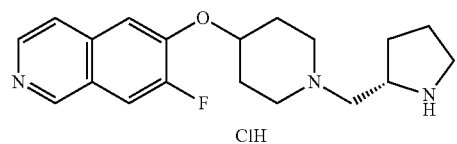 [SMILES: Fc1cc2cnccc2cc1OC1CCN(CC2CCOC2)CC1 ; Cl] ClH | 0.12 | 330.24 |

-continued
| Example No | Formula | $T_R$ | Mass [MH$^+$] |
|---|---|---|---|
| 329 | 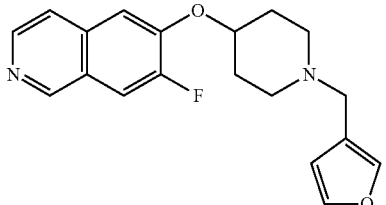 ClH | 0.67 | 327.24 |
| 330 | 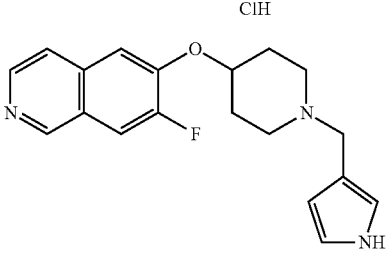 ClH | 0.18 | 326.23 |
| 331 | 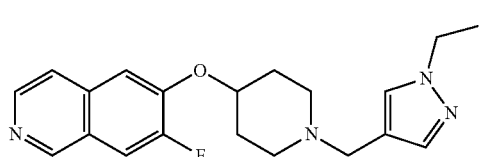 ClH | 0.23 | 335.26 |
| 332 | 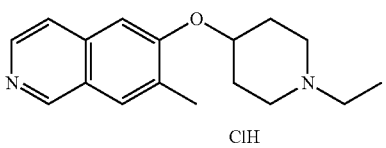 [SMILES: CCN1CCC(Oc2cc3ccncc3cc2C)CC1 ; Cl] ClH | 0.70 | 271.17 |
| 333 | 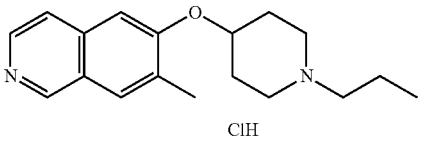 [SMILES: CCCN1CCC(Oc2cc3ccncc3cc2C)CC1 ; Cl] ClH | 0.80 | 285.21 |
| 334 | 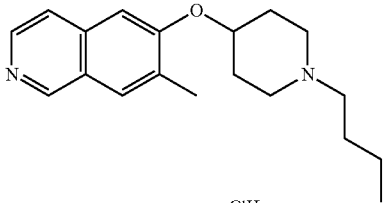 ClH | 0.87 | 299.19 |
| 335 | 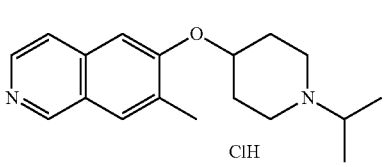 [SMILES: Cc1cc2cnccc2cc1OC1CCN(C(C)C)CC1 ; Cl] ClH | 0.78 | 285.22 |
| 336 | 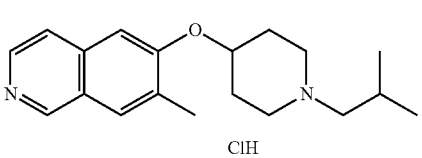 [SMILES: Cc1cc2cnccc2cc1OC1CCN(CC(C)C)CC1 ; Cl] ClH | 0.92 | 299.20 |

-continued
| Example No | Formula | $T_R$ | Mass [MH+] |
|---|---|---|---|
| 337 | 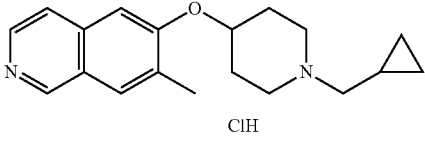 [SMILES: Cc1cc2cnccc2cc1OC1CCN(CC2CC2)CC1 ; Cl] ClH | 0.75 | 297.13 |
| 338 | 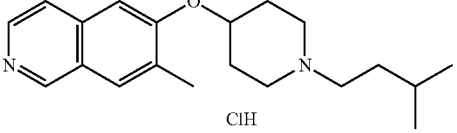 ClH | 1.01 | 313.16 |
| 339 | 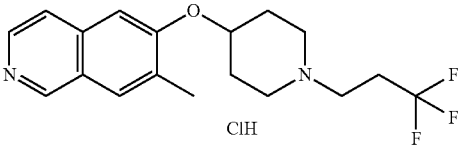 [SMILES: Cc1cc2cnccc2cc1OC1CCN(CCC(F)(F)F)CC1 ; Cl] ClH | 0.77 | 339.10 |
| 340 | 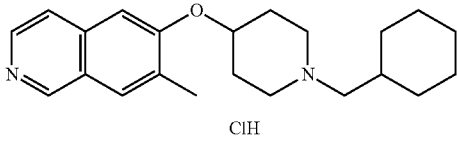 [SMILES: Cc1cc2cnccc2cc1OC1CCN(CC2CCCCC2)CC1 ; Cl] ClH | 0.98 | 339.29 |
| 341 | 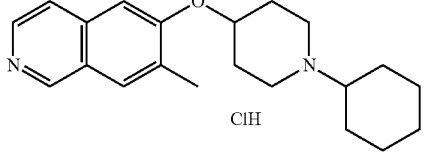 ClH | 0.91 | 325.23 |
| 342 | 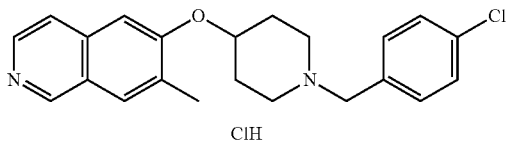 [SMILES: Cc1cc2cnccc2cc1OC1CCN(Cc2ccc(Cl)cc2)CC1 ; Cl] ClH | 1.07 | 367.15 |
| 343 | 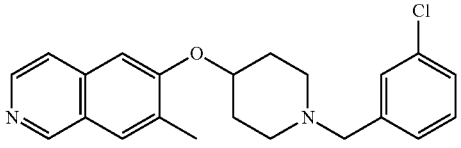 ClH | 1.01 | 367.15 |
| 344 | 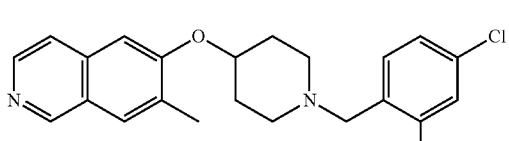 ClH | 1.07 | 401.12/ 403.14 |
| 345 | 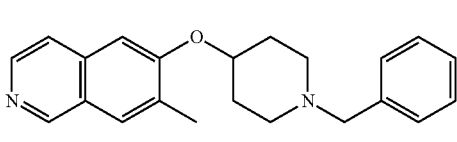 ClH | 0.99 | 333.19 |

-continued
| Example No | Formula | $T_R$ | Mass [MH⁺] |
|---|---|---|---|
| 346 | 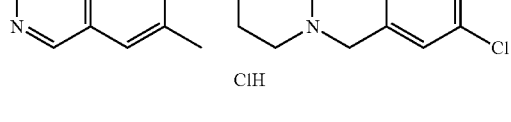 ClH | 1.13 | 401.12/ 403.14 |
| 347 | 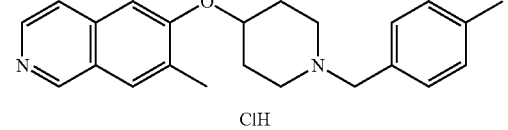 ClH | 1.00 | 347.24 |
| 348 | 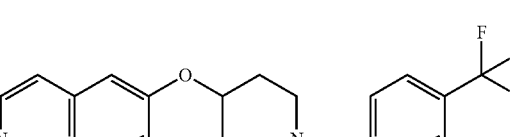 ClH | 1.09 | 401.22 |
| 349 | 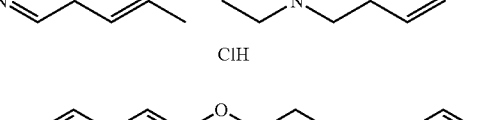 ClH | 0.63 | 334.23 |
| 350 | 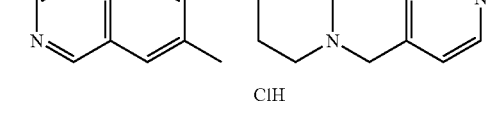 ClH | 0.69 | 334.23 |
| 351 | 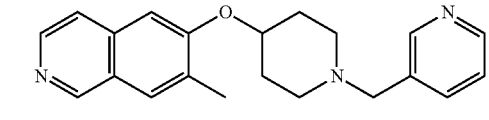 ClH | 0.90 | 334.24 |
| 352 | 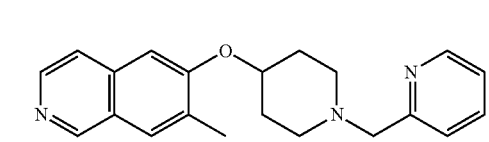 ClH | 0.83 | 411.22 |
| 353 | 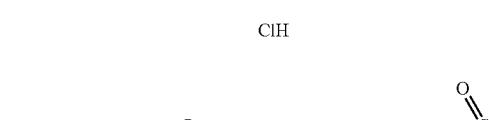 ClH | 0.88 | 429.20 |

-continued

| Example No | Formula | $T_R$ | Mass [MH$^+$] |
|---|---|---|---|
| 354 | (structure) ClH | 1.14 | 465.18 |
| 355 | (structure) ClH | 1.17 | 383.25 |
| 356 | (structure) ClH | 1.08 | 383.15 |
| 357 | (structure) ClH | 0.60 | 326.26 |
| 358 | (structure) Chiral ClH | 0.67 | 326.26 |
| 359 | (structure) ClH | 0.89 | 336.25 |

-continued

| Example No | Formula | $T_R$ | Mass [MH$^+$] |
|---|---|---|---|
| 360 | (7-methylisoquinolin-6-yl) 4-oxy-piperidine N-CH$_2$-(1-methyl-1H-pyrazol-4-yl), ClH | 0.74 | 337.24 |
| 361 | (7-methylisoquinolin-6-yl) 4-oxy-piperidine N-CH$_2$-(1H-indazol-3-yl), ClH | 0.91 | 373.23 |
| 362 | (7-methylisoquinolin-6-yl) 4-oxy-piperidine N-CH$_2$-(thiophen-3-yl), ClH | 0.97 | 338.15 |
| 363 | (7-methylisoquinolin-6-yl) 4-oxy-piperidine N-CH$_2$-(tetrahydrofuran-3-yl), ClH | 0.73 | 327.24 |
| 364 | (7-methylisoquinolin-6-yl) 4-oxy-piperidine N-CH$_2$-(piperidin-3-yl), ClH | 0.74 | 340.27 |
| 365 | (7-methylisoquinolin-6-yl) 4-oxy-piperidine N-CH$_2$-(piperidin-4-yl), ClH | 0.62 | 340.28 |

-continued
| Example No | Formula | $T_R$ | Mass [MH+] |
|---|---|---|---|
| 366 | 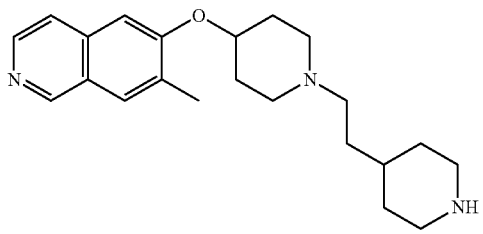 ClH | 0.66 | 354.29 |
| 367 | 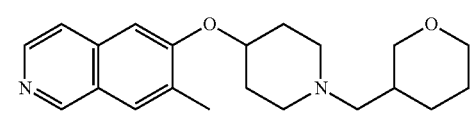 ClH | 0.79 | 341.26 |
| 368 | 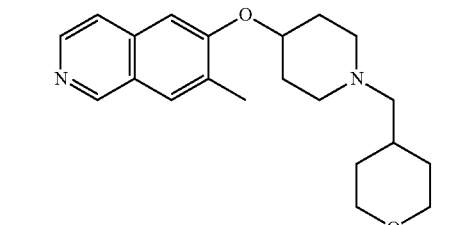 ClH | 0.77 | 341.25 |
| 369 | Chiral 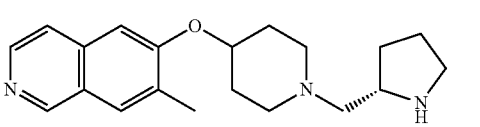 ClH | 0.76 | 326.26 |
| 370 | 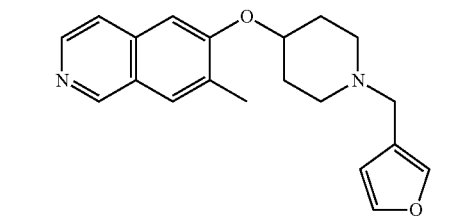 ClH | 0.81 | 323.20 |
| 371 | 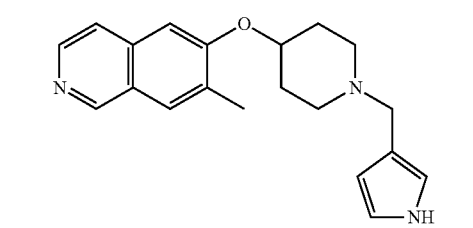 ClH | 0.84 | 322.22 |

| Example No | Formula | $T_R$ | Mass [MH$^+$] |
|---|---|---|---|
| 372 | 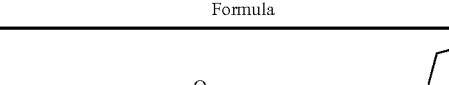 | 0.88 | 351.24 |

5,6,7-Trifluoro-isoquinoline (373)

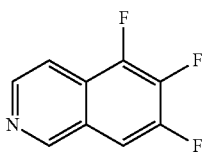 [SMILES: Fc1cc2cnccc2c(F)c1F]

5,6,7-Trifluoro-isoquinoline (373) is obtained by the same reaction sequence, used for the synthesis of 6-Fluoro-isoquinoline (23), starting from 3,4,5-Trifluorobenzaldehyde. Final purification by preparative HPLC gave the desired isoquinoline as trifluoroacetate. $R_t$=1.15 min (Method #2). Detected mass: 183.0.

4-(5,7-Difluoro-isoquinolin-6-yloxy)-piperidine-1-carboxylic acid tert-butyl ester (374)

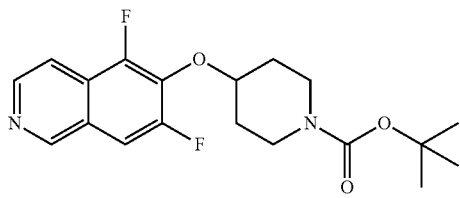 [SMILES: CC(C)(C)OC(=O)N1CCC(Oc2c(F)cc3cnccc3c2F)CC1]

The title compound was synthesized following the protocol described for 4-(Isoquinolin-6-yloxy)-piperidine-1-carbocyclic acid-tert-butylester (154). $R_t$=1.27 min (Method #TOP). Detected mass: 365.2 (M+H$^+$).

5,7-Difluoro-6-(piperidin-4-yloxy)-isoquinoline (375)

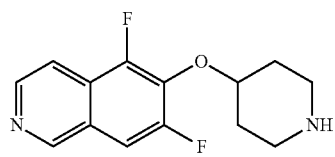 [SMILES: Fc1cc2cnccc2c(F)c1OC1CCNCC1]

4-(5,7-Difluoro-isoquinolin-6-yloxy)-piperidine-1-carboxylic acid tert-butyl ester (374) is deprotected in Methanol/2 N HCl by the general procedure described in AAV2 to yield the title compound as HCl-salt. $R_t$=0.43 min (Method #TOP). Detected mass: 265.1 (M+H$^+$).

5,7-Dichloro-6-fluoro-isoquinoline (376)

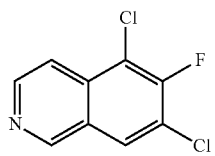 [SMILES: Fc1c(Cl)cc2cnccc2c1Cl]

5.0 g (27.5 mmol) 7-Chloro-6-fluoro-isoquinoline (150) were dissolved in 90 ml of conc. sulphuric acid. At room temperature 7.35 g (55.0 mmol) N-Chlorosuccinimide were added and the mixture was stirred at 50° C. After standing overnight at room temperature another 3 eq. N-Chlorosuccinimide were added and at the following again 5 eq. N-Chlorosuccinimide were added and the temperature was increased to 80° C. After no further conversion could be detected, the mixture was cooled to room temperature and poured on ice. The aqueous solution was brought to basic pH by adding solid NaOH. The precipitate was filtered off and washed three times with dichloromethane. After drying the organic filtrates with MgSO$_4$ and evaporation of the solvent 1.09 g of the desired isoquinoline could be isolated. $R_t$=1.26 min (Method #TOP). Detected mass: 216.0/218.0 (M+H$^+$).

4-(5,7-Dichloro-isoquinolin-6-yloxy)-piperidine-1-carboxylic acid tert-butyl ester (377)

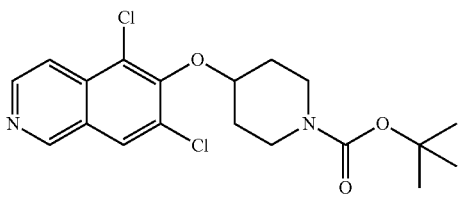

The title compound was synthesized following the protocol described for 4-(Isoquinolin-6-yloxy)-piperidine-1-carbocyclic acid-tert-butylester (154). After final purification by preparative HPLC and evaporation of the product fractions, the Boc-group is already partially cleaved. $R_t$=1.71 min (Method #2). Detected mass: 397.2/399.2 (M+H$^+$).

5,7-Dichloro-6-(piperidin-4-yloxy)-isoquinoline
(378)

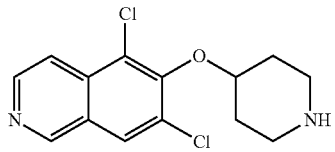

150 mg 4-(5,7-Dichloro-isoquinolin-6-yloxy)-piperidine-1-carboxylic acid tert-butyl ester (377, already partially deprotected) were dissolved in 10 ml of dichloromethane and 1 ml of trifluoroacetic acid is added at 0° C. The solution is stirred for 2 h at room temperature. For working up, 50 ml Dichloromethane were added and the solution was washed with saturated NaHCO$_3$-solution. The layers were separated and the aqueous phase was extracted once with Dichloromethane. The combined organic layers were again washed with saturated NaHCO3-solution, dried with MgSO4 and evaporated. The residue was purified by preparative HPLC. The product fractions were evaporated and the residue dissolved in 2 N HCl. After evaporation, the title compound was isolated as HCl-salt. $R_f$=0.90 min (Method #2). Detected mass: 297.1/299.1 (M+H$^+$).

Determination of Rho Kinase Inhibition

To measure Rho-kinase inhibition, IC$_{50}$ values were determined according to the following protocol:
Buffer: 25 mM Tris pH7.5; 0.02% BSA; 5% Glycerol; 0.008% Triton X100; 2% DMSO, 1 mM DTT; 1 mM MgCl$_2$; 0.5 µCi/well γ$^{33}$P ATP
Enzyme: ROCKII or ROKα) (Upstate, Catalog #14-451 Lot #24880U) 0.1 ng/µl
Final concentration of ATP in reaction mixture 40 µM
Biotinylated substrate, diluted to 0.25 µM with buffer described above (without ATP)
1. 10 µl Tris buffer (±Inhibitor)
2. Add 30 µl of enzyme solution
3. Start the reaction with 30 µL of mix substrate/ATP/ATP33
4. Incubate for 20 min at room temperature
5. Stop reaction with 30 µL of 50 mM EDTA
6. Transfer 50 µL of stopped solution to Streptavidin Flash Plate plus, Perkin Elmer, SMP 103A
7. Incubate for 30 min at RT
8. Wash 4 times with 300 µl of PBS/0.1% Tween 20
9. Radioactivity in the well was determined

| No. | IC$_{50}$ |
|---|---|
| 29 | +++ |
| 41 | ++++ |
| 44 | ++++ |
| 59 | ++++ |
| 67 | +++ |
| 72 | ++++ |
| 81 | ++++ |
| 111 | +++ |
| 100 | +++ |
| 120 | ++++ |
| 133 | ++++ |
| 134 | +++ |
| 138 | ++++ |
| 145 | +++ |
| 156 | ++++ |
| 228 | ++++ |
| 261 | ++++ |
| 265 | +++ |
| 266 | +++ |
| 269 | ++++ |
| 378 | ++++ |

The given activity is denoted as the negative logarithm of the IC$_{50}$ (pIC$_{50}$) as follows:
+: 3.0≤pIC$_{50}$<4.0
++ 4.0≤pIC$_{50}$<5.0
+++: 5.0≤pIC$_{50}$<6.0
++++: 6.0≤pIC$_{50}$

The invention claimed is:
1. A method of treating Alzheimer's disease in a patient comprising administering to the patient at least one compound of the formula (I):

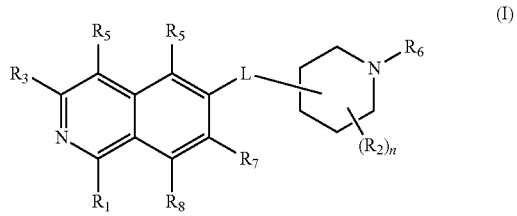

wherein
R$_1$ is
H;
R$_2$ is
H;
R$_3$ is
H, NH-phenyl or NH-benzodioxolyl;
R$_4$ is
H,
halogen,
(C$_1$-C$_6$)alkyl;
R$_5$ is
H,
halogen,
(C$_1$-C$_6$)alkyl,
cyclopropyl, phenyl, benzofuran,
(C$_1$-C$_6$)alkylene-phenyl;
R$_6$ is
H,
(C$_1$-C$_8$)alkyl,
(C$_1$-C$_6$)alkylene-(C$_{10}$)aryl,
(C$_1$-C$_6$)alkylene-CH[phenyl]$_2$, (C$_1$-C$_6$)alkylene-phenyl;
R$_7$ is
H,
halogen,
(C$_1$-C$_6$)alkyl,
phenyl;
R$_8$ is
H,
halogen,
or (C$_1$-C$_6$)alkyl;
n is 1, 2, 3 or 4; and
L is
O or
O—(C$_1$-C$_6$)alkylene;
wherein in residues R$_4$, R$_5$, R$_7$ and R$_8$ one alkyl or alkylene hydrogen atom can be optionally substituted by OH, OCH₃, COOH, COOCH₃, NH₂, NHCH₃, N(CH₃)₂, CONH₂, CONHCH₃ or CON(CH₃)₂, and in any residue one or more alkyl or alkylene hydrogen atoms can optionally be substituted by F;

and wherein phenyl or naphthyl groups are optionally substituted one or more times by $(C_1$-$C_4)$alkyl, O—$(C_1$-$C_4)$ alkyl, O-phenyl, C(O)O—$(C_1$-$C_6)$alkyl, C(O)OH, C(O)—$(C_1$-$C_4)$alkyl, halogen, NO₂, SO₂NH₂, CN, SO₂—$(C_1$-$C_4)$alkyl, NH—SO₂—$(C_1$-$C_4)$alkyl, NH₂, NH—C(O)—$(C_1$-$C_4)$alkyl, $(C_3$-$C_8)$cycloalkyl, $(C_1$-$C_4)$ alkyl-OH, C(O)N[$(C_1$-$C_4)$alkyl]₂, C(O)NH₂, N[$(C_1$-$C_4)$ alkyl]₂, $(C_2$-$C_4)$alkenylene-$(C_6$-$C_{10})$aryl, wherein the $(C_6$-$C_{10})$aryl may be further substituted with $(C_1$-$C_4)$ alkyl, $(C_1$-$C_4)$alkylene-O—$(C_1$-$C_6)$alkyl, O—$(C_1$-$C_6)$ alkyl-$(C_6$-$C_{10})$aryl, or may be vicinal substituted by a O—$(C_1$-$C_4)$alkylene-O group whereby a 5-8-membered ring is formed together with the carbon atoms the oxygen atoms are attached to, and wherein the benzofuran or benzodioxolyl groups are optionally substituted one or more times with $(C_1$-$C_4)$ alkyl, O—$(C_1$-$C_4)$alkyl, halogen or $(C_1$-$C_4)$alkylene-O—$(C_1$-$C_4)$alkyl, or a pharmaceutically acceptable salt and physiologically functional derivative thereof.

2. A method according to claim 1, wherein in formula (I), $R_3$ is H, or NH-phenyl.

3. A method according to claim 1, wherein in formula (I), $R_8$ is H, halogen or $(C_1$-$C_4)$alkyl.

4. A method according to claim 3, wherein in formula (I), $R_8$ is H, Cl, F, methyl or ethyl.

5. A method according to claim 1, wherein in formula (I), $R_4$ is H, halogen or $(C_1$-$C_4)$alkyl.

6. A method according to claim 5, wherein in formula (I), $R_4$ is H.

7. A method according to claim 1, wherein in formula (I), $R_5$ is H, halogen, $(C_1$-$C_6)$alkyl, phenyl, $(C_1$-$C_2)$alkylene-phenyl or benzofuran.

8. A method according to claim 1, wherein in formula (I), $R_7$ is H, halogen, $(C_1$-$C_4)$alkyl, or phenyl.

9. A method according to claim 1, wherein in formula (I), $R_7$ is H, fluoro, chloro, bromo, methyl, ethyl, or phenyl.

10. A method according to claim 1, wherein in formula (I), n is 1, 2 or 3.

11. A method according to claim 10, wherein in formula (I), n is 1.

12. A method according to claim 1, wherein in formula (I), $R_6$ is H, $(C_1$-$C_6)$alkyl, $(C_1$-$C_6)$alkylene-$(C_{10})$aryl or $(C_1$-$C_6)$ alkylene-phenyl.

13. A method according to claim 12, wherein in formula (I), $R_6$ is H, $(C_1$-$C_6)$alkyl, $(C_1$-$C_6)$alkylene-$(C_{10})$aryl or $(C_1$-$C_6)$alkylene-phenyl.

14. A method according to claim 1, wherein in formula (I), L is attached to the 3-position or to the 4-position of the piperidine ring.

15. A method according to claim 1, wherein in formula (I), L is attached to the 4-position of the piperidine ring.

16. A method according to claim 1, wherein in formula (I), L is O-methylene, O-ethylene or O.

17. A method according to claim 16, wherein in formula (I), L is O.

18. A method according to claim 1, wherein in formula (I),
$R_1$ is H;
$R_2$ is hydrogen;
$R_3$ is H, NH-phenyl or NH-benzodioxolyl;
$R_4$ is H, halogen or $(C_1$-$C_6)$alkyl;
$R_5$ is H, $(C_1$-$C_6)$alkyl, halogen, phenyl, $(C_1$-$C_6)$alkylene-phenyl or benzofuran;
$R_6$ is H, $(C_1$-$C_6)$alkyl, $(C_1$-$C_6)$alkylene-$(C_{10})$aryl or $(C_1$-$C_6)$alkylene-phenyl;
$R_7$ is H, halogen, $(C_1$-$C_6)$alkyl, or phenyl;
n is 1, 2 or 3, and
L is O,O-methylene or O-ethylene.

19. A method according to claim 1, wherein in formula (I),
$R_1$ is H;
$R_2$ is H;
$R_3$ is H, halogen, or NH-phenyl or NH-benzodioxolyl;
$R_4$ is H, halogen or $(C_1$-$C_4)$alkyl;
$R_5$ is H, $(C_1$-$C_6)$alkyl, halogen, phenyl, $(C_1$-$C_6)$alkylene-phenyl or benzofuran;
$R_6$ is H, $(C_1$-$C_6)$alkyl, $(C_1$-$C_6)$alkylene-phenyl or $(C_1$-$C_6)$ alkylene-$(C_{10})$aryl;
$R_7$ is H, halogen, $(C_1$-$C_6)$alkyl, or phenyl;
n is 1, 2or 3; and
L is O.

20. A method according to claim 1, wherein in formula (I),
$R_1$ is H;
$R_2$ is H;
$R_3$ is H or NH-phenyl;
$R_4$ is H, halogen or $(C_1$-$C_4)$alkyl;
$R_5$ is H, $(C_1$-$C_4)$alkyl, halogen, phenyl, or $(C_1$-$C_2)$alkylene-phenyl;
$R_6$ is H, $(C_1$-$C_6)$alkyl, $(C_1$-$C_6)$alkylene-phenyl or $(C_1$-$C_6)$ alkylene-$(C_{10})$aryl;
$R_7$ is H, halogen, $(C_1$-$C_4)$alkyl, or phenyl;
$R_8$ is H, halogen or $(C_1$-$C_4)$alkyl;
n is 1; and
L is O.

21. A method according to claim 1 comprising administering to a patient a pharmaceutical composition comprising a pharmaceutically effective amount of at least one compound of formula (I), or a pharmaceutically acceptable salt thereof, a physiologically functional derivative thereof and physiologically tolerated excipients and carriers.

22. A method according to claim 21 wherein the pharmaceutical composition further comprises additional additives or other active ingredients.

23. A method according to claim 1, wherein in formula (I), $R_3$ is

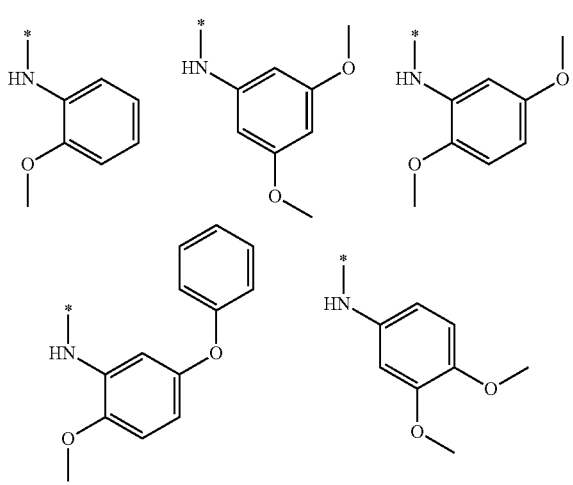

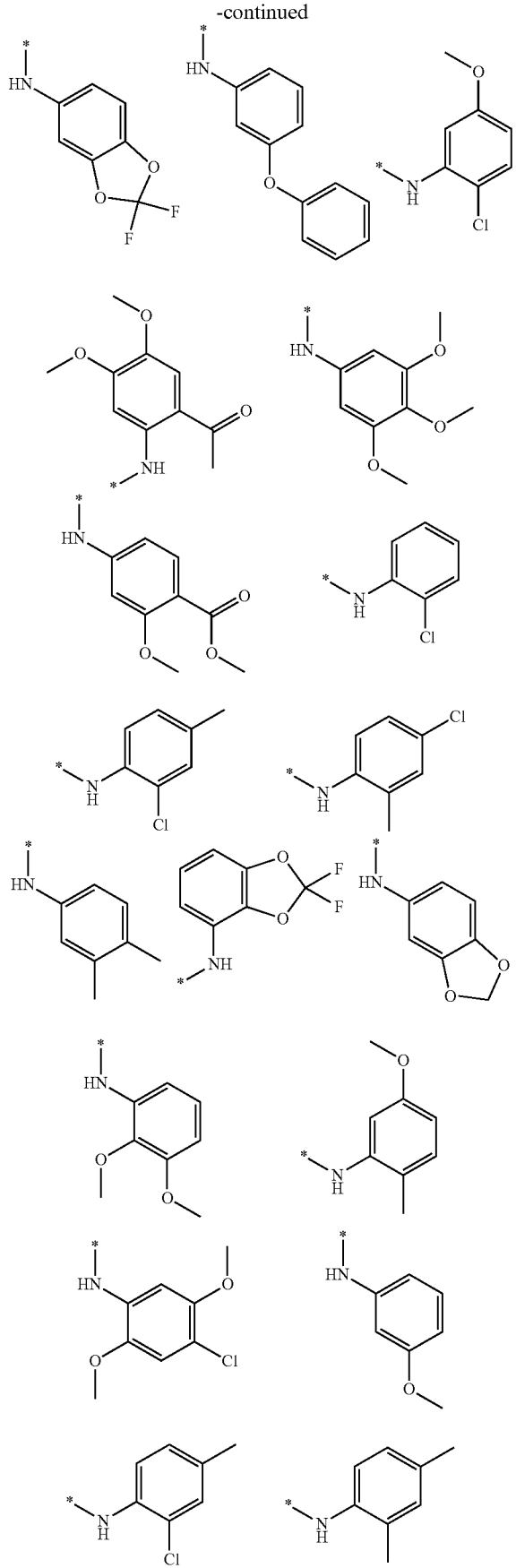
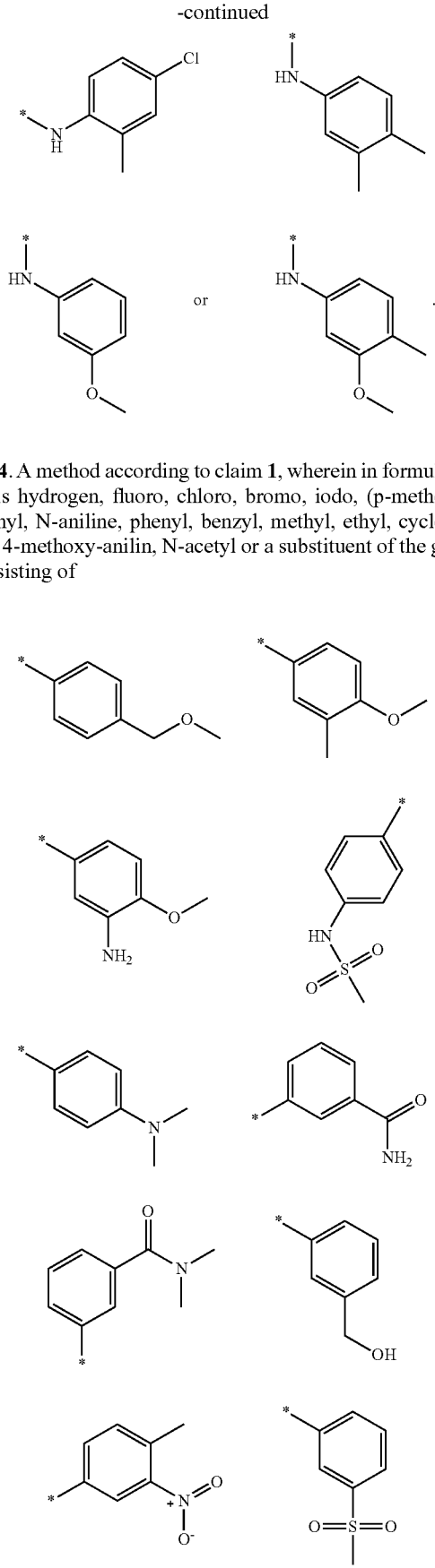
24. A method according to claim 1, wherein in formula (I), $R_5$ is hydrogen, fluoro, chloro, bromo, iodo, (p-methoxy)-phenyl, N-aniline, phenyl, benzyl, methyl, ethyl, cyclopropyl, 4-methoxy-anilin, N-acetyl or a substituent of the group consisting of -continued
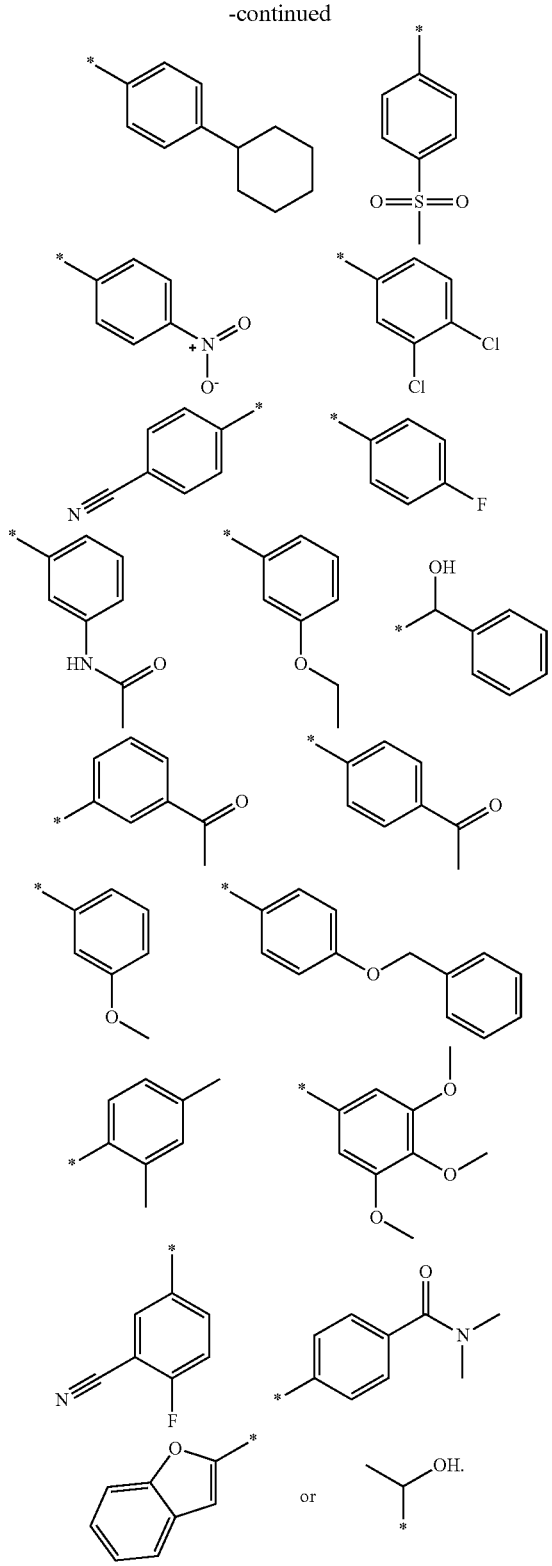
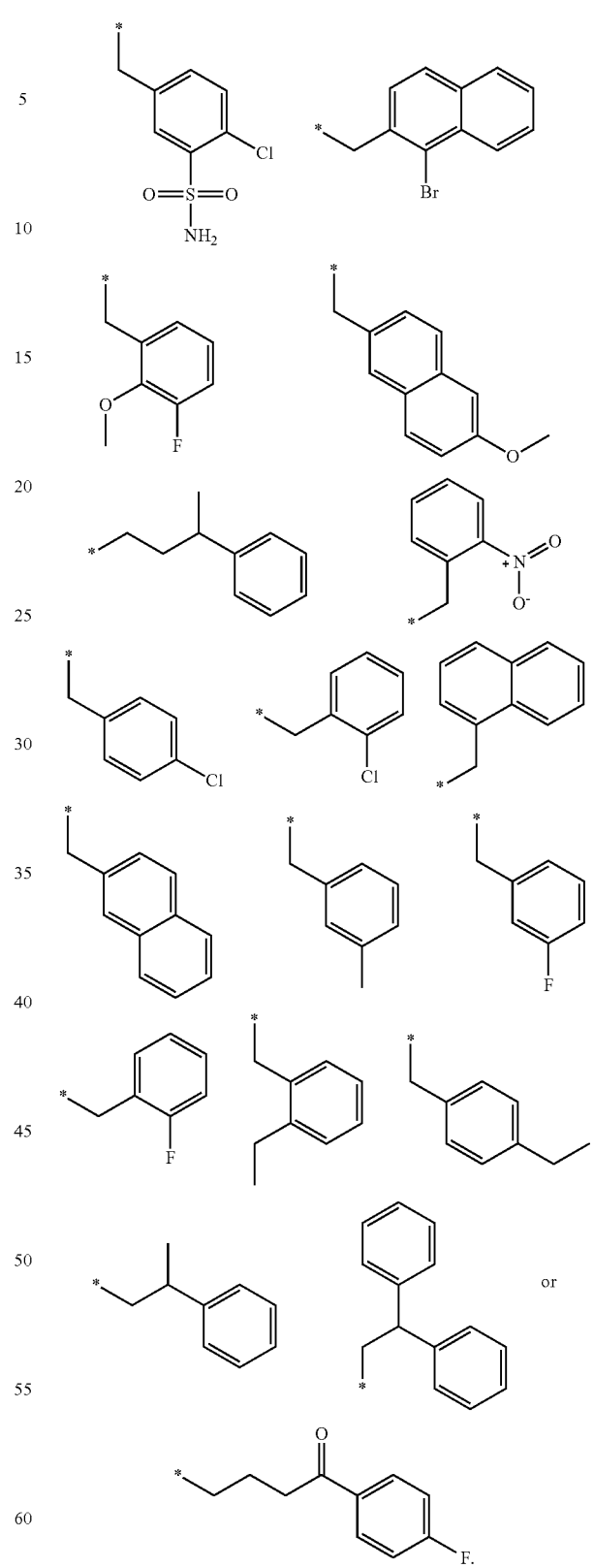
25. A method according to claim 1 wherein in formula (I), $R_6$ is H, methyl, ethyl, propyl, butyl, s-butyl, pentyl, 3-methyl-butyl, isopropyl, benzyl or a substituent of the group consisting of
* * * * *